(12) United States Patent
Coulter et al.

(10) Patent No.: US 10,434,138 B2
(45) Date of Patent: Oct. 8, 2019

(54) FORMULATIONS

(71) Applicant: Sublimity Therapeutics Limited, Dublin (IE)

(72) Inventors: Ivan Coulter, Dublin (IE); Vincenzo Aversa, Dublin (IE); Mónica Rosa, Dublin (IE); Bernard Francis McDonald, County Monaghan (IE)

(73) Assignee: Sublimity Therapeutics Limited, Dublin (IE)

( * ) Notice: Subject to any disclaimer, the term of this patent is extended or adjusted under 35 U.S.C. 154(b) by 0 days.

(21) Appl. No.: 14/536,510

(22) Filed: Nov. 7, 2014

(65) Prior Publication Data

US 2015/0132396 A1 May 14, 2015

(30) Foreign Application Priority Data

Nov. 8, 2013 (GB) .................... 1319791.8

(51) Int. Cl.
*A61K 38/13* (2006.01)
*A61K 9/00* (2006.01)
*A61K 9/16* (2006.01)
*A61K 9/48* (2006.01)
*A61K 9/50* (2006.01)
*A61K 31/196* (2006.01)
(Continued)

(52) U.S. Cl.
CPC ............ *A61K 38/13* (2013.01); *A61K 9/0053* (2013.01); *A61K 9/1658* (2013.01); *A61K 9/4858* (2013.01); *A61K 9/4866* (2013.01); *A61K 9/5026* (2013.01); *A61K 9/5036* (2013.01); *A61K 9/5047* (2013.01); *A61K 9/5073* (2013.01); *A61K 9/5089* (2013.01); *A61K 31/196* (2013.01); *A61K 31/502* (2013.01); *A61K 31/635* (2013.01); *A61K 47/10* (2013.01); *A61K 47/14* (2013.01); *A61K 47/20* (2013.01); *A61K 47/36* (2013.01); *A61K 47/42* (2013.01)

(58) Field of Classification Search
None
See application file for complete search history.

(56) References Cited

U.S. PATENT DOCUMENTS 3,971,852 A   7/1976  Brenner et al.
4,279,632 A   7/1981  Frosch et al.
(Continued)

FOREIGN PATENT DOCUMENTS

AU    1977031116    12/1976
AU     627220 B2     8/1992
(Continued)

OTHER PUBLICATIONS

Dow (Properties of solutions of METHOCEL Cellulose Ethers, pp. 8-9, published in Oct. 2013 (Year: 2013).*
(Continued)

*Primary Examiner* — Bethany P Barham
*Assistant Examiner* — Barbara S Frazier
(74) *Attorney, Agent, or Firm* — Klarquist Sparkman, LLP

(57) ABSTRACT

The present invention relates to a formulation comprising a pharmaceutically active ingredient and a coating. The invention also relates to the use of the formulation in the treatment and prevention of disorders of the gastrointestinal tract. Also disclosed are methods for preparing the formulations.

28 Claims, 6 Drawing Sheets

(51) Int. Cl.
*A61K 31/502* (2006.01)
*A61K 31/635* (2006.01)
*A61K 47/10* (2017.01)
*A61K 47/14* (2017.01)
*A61K 47/20* (2006.01)
*A61K 47/36* (2006.01)
*A61K 47/42* (2017.01)

(56) References Cited

U.S. PATENT DOCUMENTS

| | | | |
|---|---|---|---|
| 4,379,454 A | 4/1983 | Campbell et al. |
| 4,388,307 A | 6/1983 | Cavannak |
| 4,422,985 A | 12/1983 | Morishita et al. |
| 4,460,563 A | 7/1984 | Calanchi |
| 4,481,157 A | 11/1984 | Morishita et al. |
| 4,597,959 A | 7/1986 | Barr |
| 4,601,894 A | 7/1986 | Hanna et al. |
| 4,652,441 A | 3/1987 | Okada et al. |
| 4,656,161 A | 4/1987 | Herr |
| 4,695,466 A | 9/1987 | Morishita et al. |
| 4,748,023 A | 5/1988 | Tamás et al. |
| 4,749,574 A | 6/1988 | Ueda et al. |
| 4,751,241 A | 6/1988 | Motoyama et al. |
| 4,857,335 A | 8/1989 | Bohm |
| 4,891,223 A | 1/1990 | Ambegaonkar et al. |
| 5,091,184 A | 2/1992 | Khanna |
| 5,102,668 A | 4/1992 | Eichel et al. |
| 5,145,684 A | 9/1992 | Liversidge et al. |
| 5,330,835 A | 7/1994 | Kikuchi et al. |
| 5,342,625 A | 8/1994 | Hauer et al. |
| 5,350,741 A | 9/1994 | Takada |
| 5,356,896 A | 10/1994 | Kabadi et al. |
| 5,362,564 A | 11/1994 | Suzuki et al. |
| 5,385,737 A | 1/1995 | Shigeno et al. |
| 5,401,502 A | 3/1995 | Wunderlich et al. |
| 5,411,952 A | 5/1995 | Kaswan |
| 5,418,010 A | 5/1995 | Janda et al. |
| 5,478,508 A | 12/1995 | Suzuki et al. |
| 5,480,655 A | 1/1996 | Jizomoto et al. |
| 5,492,701 A | 2/1996 | Cervos et al. |
| 5,498,439 A | 3/1996 | Bonner |
| 5,500,224 A | 3/1996 | Vranckx et al. |
| 5,510,118 A | 4/1996 | Bosch et al. |
| 5,529,777 A | 6/1996 | Andrianov et al. |
| 5,529,783 A | 6/1996 | Burke et al. |
| 5,571,533 A | 11/1996 | Santus et al. |
| 5,589,455 A | 12/1996 | Woo |
| 5,645,856 A | 7/1997 | Lacy et al. |
| 5,650,232 A | 7/1997 | Glenn et al. |
| 5,665,386 A | 9/1997 | Benet et al. |
| 5,674,495 A | 10/1997 | Bowersock et al. |
| 5,795,590 A | 8/1998 | Kiefer et al. |
| 5,827,531 A | 10/1998 | Morrison et al. |
| 5,843,347 A | 12/1998 | Nguyen et al. |
| 5,851,275 A | 12/1998 | Amidon et al. |
| 5,871,774 A | 2/1999 | Lemelson |
| 5,882,680 A | 3/1999 | Suzuki et al. |
| 5,914,132 A | 6/1999 | Kelm et al. |
| 5,961,970 A | 10/1999 | Lowell et al. |
| 6,022,562 A | 2/2000 | Autant et al. |
| 6,113,936 A | 9/2000 | Takebayashi et al. |
| 6,146,663 A | 11/2000 | Bissery et al. |
| 6,174,466 B1 | 1/2001 | Kiefer et al. |
| 6,190,692 B1 | 2/2001 | Busetti et al. |
| 6,251,661 B1 | 6/2001 | Urabe et al. |
| 6,267,985 B1 | 7/2001 | Chen et al. |
| 6,284,271 B1 | 9/2001 | Lundberg et al. |
| 6,309,663 B1 | 10/2001 | Patel et al. |
| 6,361,298 B1 | 3/2002 | Kiefer et al. |
| 6,429,089 B1 | 8/2002 | Matsuki |
| 6,457,339 B2 | 10/2002 | Komura |
| 6,531,150 B1 | 3/2003 | Sunohara et al. |
| 6,585,997 B2 | 3/2003 | Moro et al. |
| 6,569,463 B2 | 5/2003 | Patel et al. |
| 6,761,903 B2 | 7/2004 | Chen et al. |
| 6,916,785 B2 | 7/2005 | Patel |
| 6,923,988 B2 | 8/2005 | Patel et al. |
| 6,972,132 B1 | 12/2005 | Kudo et al. |
| 7,097,857 B2 | 8/2006 | Tracy et al. |
| 7,267,813 B2 | 9/2007 | Watanabe et al. |
| 7,374,779 B2 | 5/2008 | Chen et al. |
| 7,727,551 B2 | 6/2010 | Massironi |
| 8,663,692 B1 | 3/2014 | Muller et al. |
| 9,278,070 B2* | 3/2016 | Coulter ............... A61K 9/107 |
| 2001/0003589 A1 | 6/2001 | Neuer et al. |
| 2001/0024658 A1 | 9/2001 | Chen et al. |
| 2002/0009457 A1 | 1/2002 | Bowersock et al. |
| 2002/0098242 A1 | 6/2002 | Darder |
| 2003/0045516 A1 | 3/2003 | Luly et al. |
| 2003/0055028 A1 | 3/2003 | Stergiopoulos et al. |
| 2003/0078194 A1 | 4/2003 | Cho et al. |
| 2003/0104048 A1 | 6/2003 | Patel et al. |
| 2003/0124061 A1 | 7/2003 | Roberts |
| 2003/0180352 A1 | 9/2003 | Patel et al. |
| 2003/0193102 A1 | 10/2003 | Yan |
| 2003/0232076 A1 | 12/2003 | Makino et al. |
| 2003/0235595 A1 | 12/2003 | Chen et al. |
| 2004/0028619 A1 | 2/2004 | Watanabe et al. |
| 2004/0029855 A1 | 2/2004 | Klaveness et al. |
| 2004/0062802 A1 | 4/2004 | Hermelin |
| 2004/0091535 A1* | 5/2004 | Vachon ............... A61K 9/145 |
| | | 424/471 |
| 2004/0126428 A1 | 7/2004 | Hughes et al. |
| 2004/0230183 A1 | 11/2004 | Breegi et al. |
| 2004/0258701 A1 | 12/2004 | Dominowski et al. |
| 2004/0258702 A1 | 12/2004 | Blonder et al. |
| 2005/0013860 A1 | 1/2005 | Venkatesh et al. |
| 2005/0037077 A1 | 2/2005 | Legrand et al. |
| 2005/0095288 A1 | 5/2005 | Honea |
| 2005/0249807 A1 | 11/2005 | Brown et al. |
| 2006/0018965 A1 | 1/2006 | Moodley et al. |
| 2006/0034937 A1 | 2/2006 | Patel |
| 2006/0135441 A1 | 6/2006 | Khodadoust et al. |
| 2006/0222701 A1 | 10/2006 | Kulkarni et al. |
| 2006/0246134 A1 | 11/2006 | Venkatesh |
| 2007/0154554 A1 | 7/2007 | Burgermeister et al. |
| 2007/0292523 A1 | 12/2007 | Moodley et al. |
| 2008/0020018 A1 | 1/2008 | Moodley et al. |
| 2008/0107694 A1 | 5/2008 | Trogden et al. |
| 2008/0113031 A1 | 5/2008 | Moodley et al. |
| 2008/0124279 A1 | 5/2008 | Andremont et al. |
| 2008/0311201 A1 | 12/2008 | Der-Yang et al. |
| 2008/0317769 A1 | 12/2008 | Kang et al. |
| 2008/0318912 A1 | 12/2008 | Fox et al. |
| 2010/0136105 A1 | 6/2010 | Chen et al. |
| 2010/0203120 A1 | 8/2010 | Coulter |
| 2010/0215737 A1 | 8/2010 | Coulter |
| 2010/0239665 A1 | 9/2010 | Coulter |
| 2010/0255087 A1 | 10/2010 | Coulter |
| 2010/0297221 A1 | 11/2010 | Coulter |
| 2011/0052645 A1 | 3/2011 | Coulter |
| 2012/0141531 A1 | 6/2012 | Coulter et al. |
| 2013/0243873 A1 | 9/2013 | Aversa et al. |
| 2014/0017313 A1 | 1/2014 | Coulter et al. |
| 2014/0234418 A1 | 8/2014 | Coulter et al. |
| 2015/0132374 A1* | 5/2015 | Coulter ............... A61K 9/4808 |
| | | 424/452 |
| 2015/0141585 A1 | 5/2015 | Choffat et al. |

FOREIGN PATENT DOCUMENTS

| | | |
|---|---|---|
| CA | 2170748 | 3/1995 |
| CA | 2 069 485 | 4/2000 |
| CA | 2376261 | 6/2000 |
| CA | 2 570 184 | 12/2005 |
| CN | 1557283 | 12/2004 |
| CN | 101797238 | 8/2010 |
| CN | 102885798 | 1/2013 |
| DE | 198 48 849 | 10/1998 |
| EP | 0 348 910 | 6/1989 |
| EP | 0 396 425 | 11/1990 |
| EP | 0 525 731 | 2/1993 |
| EP | 0 550 067 | 7/1993 |
| EP | 0 621 775 | 11/1994 |

(56) References Cited

FOREIGN PATENT DOCUMENTS

| | | |
|---|---|---|
| EP | 0 650 721 | 5/1995 |
| EP | 0694308 | 1/1996 |
| EP | 0 760 237 | 3/1997 |
| EP | 0 778 083 | 6/1997 |
| EP | 0 922 451 | 6/1999 |
| EP | 0 813 876 | 3/2002 |
| EP | 0 789 561 | 4/2004 |
| EP | 2 105 129 | 9/2009 |
| GB | 2391473 | 2/2004 |
| JP | A-58 013508 | 1/1983 |
| JP | A-58 077810 | 5/1983 |
| JP | 59-088420 | 5/1984 |
| JP | S61126016 A | 6/1986 |
| JP | A-61 151119 | 7/1986 |
| JP | H0549899 A | 3/1993 |
| JP | H06254382 A | 9/1994 |
| JP | 7247215 A | 9/1995 |
| JP | 2000-247911 | 9/2000 |
| JP | 2000-302654 | 10/2000 |
| JP | 2004-43332 A | 2/2004 |
| JP | 64 000015 | 8/2010 |
| WO | WO 91/06282 | 5/1991 |
| WO | WO 93/00063 | 1/1993 |
| WO | WO 94/15636 | 7/1994 |
| WO | WO 96/36322 | 11/1996 |
| WO | WO 97/02017 | 1/1997 |
| WO | WO 98/18610 | 5/1998 |
| WO | WO 98/40051 | 9/1998 |
| WO | WO 98/50018 | 11/1998 |
| WO | WO 98/50033 | 11/1998 |
| WO | WO 99/06024 | 2/1999 |
| WO | WO 99/13914 | 3/1999 |
| WO | WO 00/00179 | 1/2000 |
| WO | WO 2000/33862 | 6/2000 |
| WO | WO 2000/69420 | 11/2000 |
| WO | WO 2001/08666 | 2/2001 |
| WO | WO 2001/37808 | 5/2001 |
| WO | WO 2001/051008 | 7/2001 |
| WO | WO 2001/80831 | 11/2001 |
| WO | WO 2002/064162 | 8/2002 |
| WO | WO 2003/018134 | 3/2003 |
| WO | WO 2003/020243 | 3/2003 |
| WO | WO 2003/030878 | 4/2003 |
| WO | WO 2003/056938 | 7/2003 |
| WO | WO 2003/092741 | 11/2003 |
| WO | WO 2004/022220 | 3/2004 |
| WO | WO 2004/042024 | 5/2004 |
| WO | WO 2004/064997 | 8/2004 |
| WO | WO 2004/084870 | 10/2004 |
| WO | WO 2004/087204 A2 | 10/2004 |
| WO | WO 2004/108121 | 12/2004 |
| WO | WO 2005/020993 | 3/2005 |
| WO | WO 2005/020994 | 3/2005 |
| WO | WO 2005/030205 | 4/2005 |
| WO | WO 2005/048998 | 6/2005 |
| WO | WO 2005/072088 | 8/2005 |
| WO | WO 2005/074913 | 8/2005 |
| WO | WO 2005/100454 | 10/2005 |
| WO | WO 2005/107721 | 11/2005 |
| WO | WO 2006/018119 | 2/2006 |
| WO | WO 2006/026592 | 3/2006 |
| WO | WO 2006/035416 | 4/2006 |
| WO | WO 2006/110802 | 10/2006 |
| WO | WO 2007/007946 | 1/2007 |
| WO | WO 2007/012478 | 2/2007 |
| WO | WO 2007/014445 | 2/2007 |
| WO | WO 2007/018943 | 2/2007 |
| WO | WO 2007/090091 | 8/2007 |
| WO | WO 2007/095092 | 8/2007 |
| WO | WO 2009/002533 | 12/2008 |
| WO | WO 2009/014774 | 1/2009 |
| WO | WO 2010/005980 | 1/2010 |
| WO | WO 2012/074830 | 6/2012 |
| WO | WO 2012/129551 | 9/2012 |

OTHER PUBLICATIONS

Of Dow 2002 (Methocel cellulose ethers in aqueous systems for tablet coating, 2002, p. 1-29) (Year: 2002).*
LABRAFIL® M1944CS, http://www.gattefosse.com/en/applications/labrafil-m1944cs.html, accessed Dec. 10, 2015.
Mesh to Micron Conversion Chart, www.showmegold.org/news/Mesh.htm, accessed Dec. 17, 2015.
Non-Final Office Action issued in U.S. Appl. No. 14/536,503, dated Jan. 15, 2016, 55 pages.
Pelkonen et al., "In vitro prediction of gastrointestinal absorption and bioavailability: an experts' meeting report," *European Journal of Clinical Pharmacology*, 57(9): 621-629, Nov. 2001.
Strickley, "Solubilizing Excipients in Oral and Injectable Formulations," *Pharmaceutical Research*, 21(2): 201-230, Feb. 2004.
Fukata et al. "The effective therapy of cyclosporine a with drug delivery system in experimental colitis," *Journal of Drug Targeting*, 19(6): 458-467, 2011.
Mastronardi et al. "Short onset of ulcerative colitis predicts the response to cyclosporine (Neoral) as bridge therapy in steroid-refractory ulcerative colitis," Poster presentations: Clinical: Therapy and observations, pp. S157-S158, 2013.
Sharkey et al. "The use of Cyclosporin A in acute steroid-refractory ulcerative colitis: Long term outcomes," *Journal of Crohn's and Colitis*, 5: 91-94, 2011.
"Nimotop® (nimiodipine) Capsules for Oral Use," FDA approved label text, Bayer Health Care: 2005.
Akhlaghi et al. "Distribution of Cyclosporin in Organ Transplant Recipients," *Clin Pharmacokinet*, 41(9): 615-637, 2002.
Al-Meshal et al., "Oral administration of liposomes containing cyclosporine: a pharmacokinetic study," *International Journal of Pharmaceutics* 168:163-168, 1998.
Anderberg et al., "Sodium Caprate Elicits Dilatations in Human Intestinal Tight Junctions and Enhances Drug Absorption by the Paracellular Route," *Pharmaceutical Research* 10(6):857-864, 1993.
Barnes et al., "Theophylline: New Perspectives for an Old Drug," *AM J Respir Crit Care Med* 167:813-818, 2003.
Borel et al., "Carotenoids in biological emulsions: solubility, surface-to-core distribution, and release from lipid droplets," *Journal of Lipid Research* 37:250-261, 1996.
Bowersock et al. "Oral vaccination with alginate microsphere systems," *Journal of Controlled Release*, 39: 209-230, 1996.
Cannon, "Oral Solid Dosage Forms of Lipid-based Drug Delivery Systems," *AM Pharm Rev* 8(1):108-115, 2005.
Chourasia et al., "Pharmaceutical approaches to colon targeted drug delivery systems," *J. Pharm. Pharmaceut. Sci.* 6(1):33-66-2003.
Chowdary et al., "Controlled Nifedipine Release from Microcapsules of its Dispersions in PVP-MCC and HPC-MCC," *Drug Development and Industrial Pharmacy* 21(10):1183-1192, 1995.
Cummins et al. "The Hydroxylase Inhibitor Dimethyloxalyglycine is Protective in a Murine Model of Colitis," *Gastroenterology*, 134:156-165, 2008.
Davis, "Formulation strategies for absorption windows," *DDT*, 10(4): 249-257, 2005.
Dhara et al., "Stability of Sodium Dodecyl Sulfate Micelles in the Presence of a Range of Water-Soluble Polymers: A Pressure-Jump Study," *J. Phys. Chem. B.*, 105: 7133-7138; 2001.
Drewe et al., "The absorption site of cyclosporine in the human gastro-intestinal tract," *Br. J. clin. Pharmac.* 33:39-43, 1992.
Drug Bank, www.drugbank.ca/drugs/DB0024-4, 12 pages.
Feagan et al., "Low-Dose Cyclosporine for the Treatment of Crohn's Disease," *The New England Journal of Medicine*, 330(26):1846-1851, Jun. 30, 1994.
Florindo et al. "The enhancement of the immune response against S. equi antigens through the intranasal administration of poly-ε-caprolactone-based nanoparticles," *Biomaterials*, 30: 879-891, 2009.
French et al., "Evaluation of the Physiochemical Properties and Dissolution Characteristics of Mesalamine: Relevance to Controlled Intestinal Drug Delivery," *Pharmaceutical Research* 10(9):1285-1290, 1993.
Gao et al., "Physiochemical characterization and evaluation of a microemulsion system for oral delivery of yclosporine A," *International Journal of Pharmaceutics* 161:75-86, 1998.

(56) References Cited

OTHER PUBLICATIONS

Greener et al., "Interaction of Anionic Surfactants with Gelatin: Viscosity Effects," *Macromolecules*, 20: 2490-2498; 1987.
Gursoy et al., "Self-emulsifying drug delivery systems (SEDDS) for improved oral delivery of lipophilic drugs," *Biomedicine & Pharmacotherapy* 58:173-182, 2004.
Holmberg et al., *Surfactants and Polymers in Aqueous Solution.* John Wiley & Sons, Ltd. 2002.
Holmgren et al. "Mucosal immunity and vaccines," *Nature Medicine*, 11(4): 545-553, 2005.
Ikegawa et al., Inhibition of P-glycoprotein by flavonoid derivatives in Adriamycin-resistant human myelogenous leukemia (K562/ADM)cells, *Cancer Letters* 177:89-93, 2002.
Ismailos et al. "unusual solubility behavior of cyclosporine A in aqueous media," *J. Pharm. Pharmacol.* 43:287-289, 1991.
Kim et al., "Once-a-Day Oral Dosing Regimen of Cyclosporin A: Combined Therapy of Cyclosporin a Premicroemulsion Concentrates and Enteric Coated Solid-State Premicroemulsion Concentrates," *Pharmaceutical Research* 18(4):454-459, 2001.
Klausner et al. "Expandable gastroetentive dosage forms," *Journal of Controlled Release* 90:143-162, 2003.
Lawrance "Novel topical therapies for distal colitis," *World Journal of Gastrointestinal Pharmacology and Therapeutics* 1(5):87-93, 2010.
Lei et al. "Solid Self-Nanoemulsifying Cyclosporine a Pellets Prepared by Fluid-Bed Coating: Stability and Bioavailability Study," *Journal of Biomedical Nanotechnology*, 8: 515-521, 2012.
Liu et al., "Gelatin-Stabilised Microemulsion-Based Organogels Facilitates Percutaneous Penetration of Cyclosporin A In Vitro and Dermal Pharmacokinetics In Vivo," *Journal of Pharmaceutical Sciences* 96(11):3000-3009, Nov. 2007.
Loufrani, et al. "Vasodilator treatment with hydralazine increases blood flow in mdx mice resistance arteries without vascular wall remodeling or endothelium function improvement," *Journal of Hypertension* 23(10):1855-1860, 2005.
Madene et al., "Flavour encapsulation and controlled release—a review," *International Journal of Food Science and Technology* 41:1-21, 2006.
Malaekeh-Nikouei et al. "Preparation, Characterization, and Mucoadhesive Properties of Chitosan-Coated Microspheres Encapsulated with Cyclosporine A," *Drug Devleopment and Industrial Pharmacy*, 34:492-498, 2008.
Manakova et al., "Failure of FK506 (tacrolimus) to alleviate apomorphine-induced circling in rat Parkinson model in spite of some cytoprotective effects in SH-SY5Y dopaminergic cells," *Brain Research* 1038:83-91, 2005.
McGinity et al., "Aqueous Polymeric Coatings for Pharmaceuticals Dosage Forms," *Marcel Dekker, Inc.*, 1997.
McGinity et al., "Enteric Film Coating of Soft Gelatin Capsules," *Drug Development & Delivery* 3(6), Sep. 6, 2003.
Miller et al., "Controlled Trial of Nimodipine in Amyotrophic Lateral Sclerosis," *Neuromusc. Disord.*, 6(2):101-104, 1996.
Milojevic et al., "Amylose as a coating for drug delivery to the colon: Preparation and in vitro evaluation using 5-aminosalicylic acid pellets," *Journal of Controlled Release* 38:75-84, 1996.
Muller et al. "Competitive Adssorption of Gelatin and Sodium Dodecylbenzenesulfonate at Hydrophobic Surfaces," *Langmuir*, 14: 3107-3114; 1998.
Murthy et al., "Treatment of Dextran Sulfate Sodium-Induced Murine Colitis by Intracolonic Cyclosporin," *Digestive Diseases and Sciences* 38(9):1722-1734, Sep. 1993.
Newman, et al. "Use of Nonionic Block Copolymers in Vaccines and Therapeutics," *Critical Reviews™ in Therapeutic Drug Carrier Systems* 15(2):89-142, 1998.
Qiu et al., "Developing Solid Oral Dosage Forms: Pharmaceutical Theory & Practice," *Academic Press* p. 445 only, 2009.
Reich, "Formulation and physical properties of soft capsules," *Chapter 11, Pharmaceutical Capsules*, $2^{nd}$ edition, Edited by Fridrun Podczeck and Brian E Jones, p. 208, 2004.

Ribeiro et al., "Microencapsulation of lipophilic drugs in chitosan-coated alginate microspheres," *International Journal of Pharmaceutics* 187:115-123, 1999.
Riviere, et al. "Effects of Vasoactive Drugs on Transdermal Lidocaine Iontophoresis," *Journal of Pharmaceutical Sciences* 80(7):615-620, 1991.
Rodriguez et al., "Colonic budesonide delivery from ph-dependent microcapsules containing lipidic cores," *Acta Technologiae et Legis Medicamenti* 11(1):45-52, 2000.
Rutgeerts et al. "A Comparison of Budesonide with Prednisolone for Active Crohn's Disease," *The New England Journal of Medicine*, 331(13): 842-845, 1994.
Sandborn et al. "The Pharmacokinetics and Colonic Tissue Concentrations of Cyclosporine After IV, Oral, and Enema Administration," *J. Clin. Pharmacol.* 31:76-80, 1991.
Shioji, Yusaku "Manufacturing technology of solid formulation", CMC Publishing Co. Ltd., pp. 46-48 and 174-177, Jan. 27, 2003.
Strowig et al., Comparison of Insulin Monotherapy and Combination Therapy with Insulin and Metformin or Insulin and Troglitazone in Type 2 Diabetes, *Diabetes Care* 25(10):1691-1698, 2002.
Sweetman and Martindale, "Nimodipine," *Cardiovascular Drugs* p. 946, 2002.
van Deventer, "Small therapeutic molecules for the treatment of inflammatory bowel disease," *Gut* 50(Suppl III): iii47-iii53, 2002.
Watts, "Colonic Drug Delivery," *Drug Development and Industrial Pharmacy*, 23(9): 893-913, 1997.
Wesley et al., "Structure of Polymer/Surfactant Complexes Formed by Poly(2-(dimethylamino)ethyl metharylate) and Sodium Dodecyl Sulfate," *Langmuir* 18: 5704-5707; 2002.
Westerink et al. "ProJuvant™ (Pluronic F127®/chitosan) enhances the immune response to intranasally administered tetanus toxoid," *Vaccine* 20:711-723, 2002.
Xu et al. "Effects of anionic surfactants on grafting density of gelatin modified with PDMS-E," *Colloids and Surfaces B: Biointerfaces*, 114:310-315, 2014.
Xu et al. "Structure Evolution of Gelatin Particles Induced by pH and Ionic Strength," *Microscopy Research and Technique*, 76:272-281, 2013.
Yang et al., "Transport and uptake characteristics of a new derivative of berberine (CPU-86017) by human intestinal epithelial cell line: Caco-2," *Acta Pharmacol Sin* 24(12):1185-1191, 2003.
Yeh et al., "Effect of Medium-Chain Glycerides on Physiological Properties of Rabbit Intestinal Epithelium in Vitro," *Pharmaceutical Research* 11(8):1148-1154, 1994.
Zhang et al., "P-glycoprotein restricted transport of nimodipine across blood-brain barrier," *Acta Pharmacol Sin* 24(9):903-906, 2003.
Zuber et al., "Reversible cerebral angiopathy," *J. Neurol* 253:1585-1588, 2006.
Onoue et al., "Inhalable dry-emulsion formulation of cyclosporine A with improved anti-inflammatory effects in experimental asthma/COPD-model rats," *European Journal of Pharmaceutics and Biopharmaceutics*, vol. 80, pp. 54-60, Oct. 8, 2011.
Guzman et al., "Combined Use of Crystalline Salt Forms and Precipitation Inhibitors to Improve Oral Absorption of Celecoxib from Solid Oral Formulations," *Journal of Pharmaceutical Sciences*, 96(10): 2686-2702, Oct. 2007.
Takatsuka et al., "Intestinal Graft-Versus-Host Disease: Mechanisms and Management," *Drugs*, 63(1): 1-15, 2003.
Bacigalupo, "Management of acute graft-versus-host disease," *British Journal of Haematology*, vol. 137, 87-98, 2007.
Keck, "Cyclosporine Nanosuspensions: Optimised Size Characterisation & Oral Formulations," Dissertation submitted to der Freien Universitat Berlin, 2006.
Final Office Action issued by U.S. Patent and Trademark Office dated Dec. 21, 2016, for U.S. Appl. No. 14/536,503.
Non-Final Office Action issued by U.S. Patent and Trademark Office dated May 8, 2017, for U.S. Appl. No. 14/536,503.
Stack et al., "Short- and long-term outcome of patients treated with cyclosporin for severe acute ulcerative colitis," *Aliment. Pharmacol. Ther.*, vol. 12, pp. 973-978, Jun. 1, 1998.
Campbell et al., "Combination immunomodulatory therapy with cyclosporine and azathioprine in corticosteroid-resistant severe ulcer-

(56) References Cited

OTHER PUBLICATIONS ative colitis: the Edinburgh experience of outcome," *Digestive and Liver Disease*, vol. 35, pp. 546-551, 2003.
Cho et al., "Preparation and Evaluation of Solid-Self-Emulsifying Drug Delivery System Containing Paclitaxel for Lymphatic Delivery," *Journal of Nanomaterials*, vol. 2016, 15 pages, May 5, 2016.
Longet et al., "Thermostability of the coating, antigen and immunostimulator in an adjuvanted oral capsule vaccine formulation," *International Journal of Pharmaceutics*, 534(1-2): 60-70, Oct. 9, 2017.
Non-Final Office Action issued for U.S. Appl. No. 15/034,844 dated Aug. 23, 2017.
Rolfsen et al., "Oil-in-water biocompatible microemulsion as a carrier for the antitumor drug compound methyl dihydrojasmonate," *International Journal of Nanomedicine*, vol. 10, pp. 585-594, Jan. 12, 2015.
Aguirre et al., "In vitro and in vivo preclinical evaluation of a minisphere emulsion-based formulation (SmPill®) of salmon calcitonin," *European Journal of Pharmaceuticals*, vol. 79, pp. 102-111, Sep. 6, 2015.
Actis et al., "Oral microemulsion cyclosporin to reduce steroids rapidly in chronic active ulcerative colitis," *European Journal of Gastroenterology & Hepatology*, 11(8): 905-908, Aug. 1, 1999.
Dvorackova et al., "Coated capsules for drug targeting to proximal and distal part of human intestine," *Acta Poloniae Pharmaceutica*, 67(2): 191-199, Mar. 1, 2010.
Oehme et al., "Preparation and characterization of shellac-coated anthocyanin pectin beads as dietary colonic delivery system," *Mol. Nutr. Food Res.*, vol. 55, pp. S75-S85, May 2, 2011.

\* cited by examiner

FORMULATIONS

CROSS REFERENCE TO RELATED APPLICATION

This application claims the benefit of Great Britain Application No. 1319791.8, filed on Nov. 8, 2013, which application is incorporated herein by reference in its entirety.

BACKGROUND

This invention relates to a formulation comprising a pharmaceutically active ingredient and a coating. The invention also relates to the use of the formulation in the treatment and prevention of disorders of the gastrointestinal tract. Also disclosed are methods for preparing the formulations.

Formulating pharmaceutically active ingredients into a form suitable for administration to a patient is a developed area of science. It is also a key consideration for the efficacy of a drug. There are many examples of methods for formulating drugs and other active ingredients. The aim of these formulations are varied and can range from increasing systemic absorption, allowing for a new route of administration, improving bioavailability, reducing metabolism of the active, or avoiding undesirable routes of administration. WO 2008/122965 discloses oral cyclosporin minicapsule compositions with modified release properties which release cyclosporin in at least the colon. WO2010/133609 discloses compositions comprising a water-soluble polymer matrix in which are dispersed droplets of oil, the compositions comprising a modified release coating. The disclosed compositions also contain an active principle.

BRIEF SUMMARY OF THE DISCLOSURE

It has surprisingly been found that pharmaceutical formulations which have a coating which is or comprises a water-soluble cellulose ether have a higher total release of active from the formulation and/or a greater rate of release of the active compared to a formulation which does not have the coating. This coat constitutes the first coating. The first coating may also be referred to as a subcoat. The greater extent and/or rate of release of the active provides a formulation which has a novel in-vitro release profile (and consequently a novel in-vivo pharmacokinetic profile) compared to the same formulations without the coating. In vitro dissolution testing has also shown that formulations according to the invention reduce batch to batch variability in the in-vitro release profile. Accordingly, the formulations are expected to demonstrate a reduced inter and/or intra-patient variability compared to formulations lacking the coating.

The formulation may comprise a second coating to control or modulate release of the active ingredient, for example cyclosporin A, mesalazine and hydralazine, from the formulation. Advantageously the coating is a polymeric coating to provide delayed and/or sustained release of the active ingredient, for example cyclosporin A, mesalazine or hydralazine, from the formulation. Suitable such coatings are described in more detail below and include a coating which is or comprises a coating selected from a controlled release polymer, a sustained release polymer, an enteric polymer, a pH independent polymer, a pH dependent polymer and a polymer specifically susceptible to degradation by bacterial enzymes in the gastrointestinal tract, or a combination of two or more such polymers. In a particular embodiment the second coating is or comprises a pH-independent polymer, for example a coating which is or comprises ethyl cellulose. In a further specific embodiment the second coating is or comprises a pH-independent polymer, for example ethyl cellulose, and a water-soluble polysaccharide, for example pectin or chitosan, or a combination thereof, particularly pectin. The respective polymers of the first coating and the second coating are different. Often the second coating does not have any polymer found in the first coating; for example, if the first coating comprises (e.g. is) a hydroxypropylmethyl cellulose, then the second coating will not also comprise a hydroxypropylmethyl cellulose. In addition the situation is contemplated where the first coating is or comprises a water-soluble ether or ester of a cellulose ether, the major component(s) (e.g. more than 50%) of the second coating is or comprises a different polymer to that of the first coating. Accordingly, the first and second coatings suitably provide two layers of material as part of the composition. It is to be understood that when the second coating comprises a mixture of components, minor components of the outer second coating may be the same as the material of the sub-coating. By way of example, when the first coating is or comprises HPMC and the second coating comprises ethyl cellulose, the ethyl cellulose may optionally further comprise a minor amount (e.g. less than 50%, 40%, 30% or 20%) of the first coating material, HPMC in this example. In such embodiments the first coating and the second coating are considered to be different.

According to an embodiment of the invention, the active ingredient optionally is or comprises cyclosporin A, hydralazine or mesalazine, said coating which is or comprises a water-soluble cellulose ether is a first coating and the formulation further comprises a second coating outside the first coating; and wherein the second coating is or comprises a coating, suitably a polymeric coating, to control or modulate release of the active ingredient from the formulation. The polymeric coating may be as further described elsewhere in this specification.

In the invention the first coating suitably is or comprises a water-soluble cellulose ether. The water-soluble cellulose ether may be any cellulose ether or derivative of a cellulose ether, for example an ester of a cellulose ether, that is soluble in water. Therefore, the water-soluble cellulose ether may be selected from: an alkyl cellulose; a hydroxyalkyl cellulose; a hydroxyalkyl alkyl cellulose; and a carboxyalkyl cellulose. Suitably the first coating is or comprises one or more water-soluble cellulose ethers selected from: methyl cellulose, hydroxyethyl cellulose, hydroxypropyl cellulose and hydroxypropylmethyl cellulose, and combinations thereof. In particular embodiments the first coating is or comprises a water-soluble hydroxypropyl methylcellulose. The water-soluble cellulose ethers and water-soluble derivatives thereof (e.g. water-soluble esters of a cellulose ether) present in the first coating (sub-coat) suitably form at least 20%, 40%, 50%, 60%, 70%, 80%, 85% or 90% by weight of the dry weight of the first coating.

The formulation of the invention may comprise a core, a first coating outside the core, wherein the first coating is a water-soluble cellulose ether as described above and elsewhere herein; and a second coating outside the first coating; wherein the core comprises a hydrogel-forming polymer matrix and a pharmaceutically active ingredient, optionally a hydrophobic or hydrophilic active ingredient, for example cyclosporin A, hydralazine or mesalazine.

In accordance with the present invention there is provided a pharmaceutical formulation comprising a core and a coating, wherein the core comprises a hydrogel forming polymer matrix and a pharmaceutically active ingredient and the coating comprises or is a water soluble cellulose ether and the coating is present in an amount corresponding to a weight gain due to the coating of from 0.5% to 20% by weight of the core.

The coating of the present invention modifies the release of the active ingredient from the formulation. There would be an expectation that a coating on a formulation would slow the rate of release of the active ingredient within a formulation. One might reasonably expect this as coating the formulation with additional material would provide an additional barrier to a dissolution medium coming into contact with the active ingredient in the formulation. In contrast to this expected outcome, the present invention surprisingly provides a formulation with a coating comprising or being a water soluble cellulose ether that increases the rate of release of the active ingredient compared to a formulation without the coating. In addition the coating of the present invention has the beneficial effect of maintaining the active ingredient in solution, whereas a comparable formulation lacking the coating of the invention provides less of the active ingredient in solution as time progresses. Without wishing to be bound by theory, it is believed that the coating prevents precipitation of the active ingredient from solution, thereby maintaining a higher amount of the active in solution.

Throughout the present application active ingredient, active, and pharmaceutically active ingredient are used interchangeably and all refer to the same subject matter.

The formulation of the present invention may take any form known to the person skilled in the art. Preferably, the formulation is an oral formulation. The formulation may be in the form of a single minibead or a multiplicity of minibeads.

The formulation may comprise a coating present in an amount corresponding to a weight gain due to the coating selected from ranges of from: 0.5% to 15%; 1% to 15%; 1% to 12%; 1% to 10%; 1% to 8%; 1% to 6%; 1% to 4%, 2% to 10%; 2% to 8%; 2% to 6%; 2% to 7%; 2% to 4%; 4% to 8%; 4% to 7%, 4% to 6%, 5% to 7%; 7% to 20%; 7% to 16%; 9% to 20%; 9% to 16%; 10% to 15%; and 12% to 16%.

The formulation of the invention may comprise a coating with a thickness of 1 µm to 1 mm. Thus, the % weight gain due to the coating specified above may correspond to a thickness of 1 µm to 1 mm.

The invention also provides for a pharmaceutical formulation comprising a core and a coating, wherein the core comprises a hydrogel forming polymer matrix and a pharmaceutically active ingredient, wherein the coating comprises or is a water-soluble cellulose ether and the coating has a thickness of from 1 µm to 1 mm.

The coating may have a thickness selected from ranges of from: 1 µm to 500 µm; 10 µm to 250 µm; 10 µm to 100 µm; 10 µm to 50 µm; 10 µm to 20 µm; 50 µm to 100 µm; 100 µm to 250 µm; 100 µm to 500 µm; 50 µm to 500 µm; 50 µm to 250 µm; 100 µm to 1 mm; 500 µm to 1 mm. The coating having the thicknesses disclosed in this paragraph may be any of the coatings in the application. In particular the coating referred to in this paragraph may be the water-soluble cellulose ether coating.

Any of the pharmaceutical formulations of the invention may comprise a further, or second, coating. The second coating may be outside the first coating. The second coating may be or comprise a delayed release polymer. Where the formulations of the invention comprise a second coating the coating referred to above may be referred to as the first coating. Any disclosure given below in relation to a second coating is also applicable to the second coating referred to in this paragraph. In any embodiment and any aspect of the invention the first and second coating may be different.

The invention therefore, contemplates a pharmaceutical formulation comprising a core, a first coating and a second coating outside of the first coating, wherein the core comprises a pharmaceutically active ingredient, the first coating comprises or is a water soluble cellulose ether, and the second coating comprises or is a delayed release polymer, wherein the first coating is present in an amount corresponding to a weight gain due to the coating of from 0.5% to 20% by weight of the core. The core may optionally further comprise a hydrogel forming polymer.

In addition, the invention provides for a pharmaceutical formulation comprising a core, a first coating and a second coating outside of the first coating, wherein the core comprises a pharmaceutically active ingredient, the first coating comprises or is a water soluble cellulose ether, and the second coating comprises or is a delayed release polymer, and the first coating has a thickness of from 1 µm to 1 mm. The core may optionally further comprise a hydrogel forming polymer.

Included in the invention is a pharmaceutical formulation comprising a core and a coating, wherein the core comprises a pharmaceutically active ingredient and the coating comprises or is a water-soluble cellulose ether. The coating is present in an amount to provide a higher % in solution of the pharmaceutically active ingredient from the formulation than a formulation without the coating at 0.5 hours from the start of a dissolution test to measure the % in solution of the pharmaceutically active ingredient in a dissolution medium consisting of water, the dissolution test being carried out in accordance with USP <711> Dissolution using Apparatus II (paddle apparatus) operated with a paddle speed of 75 rpm and with the dissolution medium at a temperature of 37° C.±0.5° C. Alternatively, the higher % in solution of the active ingredient from the formulation may be at 20 mins, 40 mins 1 hour or 1.5 hours from the start of a dissolution test instead of at 0.5 hours. Additionally, the higher % in solution of the active ingredient from the formulation may be at time points selected from: 20 mins and 40 mins; 0.5 hours and 1 hour; 1 hour and 1.5 hours; or 0.5 hours, 1 hour and 1.5 hours. The % in solution of the active ingredient from the formulation may be higher for a period selected from one of those spanning from: 0 hours to 0.5 hours; 0 hours to 1 hour; 0 hours to 1.5 hours; or 0.5 hours to 1.5 hours. Preferably, the % in solution of the pharmaceutically active ingredient from the formulation of the invention is higher than a formulation without the coating for the period up to 1.5 hours from the start of the dissolution test.

In embodiments the higher % in solution of the pharmaceutically active ingredient is at 0.5 hours and a time point selected from: 20 mins, 40 mins, 1 hour 1.5 hours, and any combination thereof. In embodiments the higher % in solution of the pharmaceutically active ingredient may be for the period up to 1.5 hours from the start of the dissolution test.

The % in solution of the active of a formulation of the invention with the coating may be higher than a formulation without the coating at a specific time point by: 10 or more, 15 or more, 20 or more, 30 or more, 40 or more, or 45 or more at 0.5 hours; 10 or more, 15 or more, or 20 or more at 1 hour; and/or 3 or more, 5 or more, 8 or more, or 10 or more at 1.5 hours. The higher % in solution values described herein may be attained when a single time point is specified, more than one time point is specified or where a period has been specified.

For example, a formulation of the invention with the coating may give a % in solution that is 10 or more higher at 0.5 hours and 10 or more higher at 1 hour and 5 or more higher at 1.5 hours.

It is contemplated within this aspect of the invention that the coating may further be present in an amount corresponding to a % weight gain by weight of the core of: from 1% to 15%, from 1% to 12%, from 2% to 15%, from 2% to 12%, from 1% to 9%, from 2% to 8%, from 2% to 3%, from 2% to 5%, from 5% to 7%, from 4% to 6.5%, from 6% to 7%, or from 2% to 7%. Preferably, the coating may be present in an amount corresponding to a weight gain of from 1% to 9%, from 2% to 8%, from 4% to 6.5%, from 2% to 5% or from 2% to 7%, optionally from 4% to 6.5%, from 2% to 5% or from 2% to 7%. The % weight gain of the coating relative to the core may be combined with any of the specified higher % in solution values and any time point.

For example, the coating may be present in an amount to provide a higher % in solution of the pharmaceutically active ingredient at 0.5 hours, wherein the % in solution of the active may be higher by 30, optionally 35 and the coating may be present in an amount corresponding to a % weight gain by weight of the core of from 2% to 7%, optionally from 2% to 4%. Alternatively, the coating may be present in an amount to provide a higher % in solution of the pharmaceutically active ingredient at 0.5 hours, wherein the % in solution of the active may be higher by 40, optionally 45 and the coating may be present in an amount corresponding to a % weight gain by weight of the core of from 4% to 7%, optionally from 5% to 7%.

The invention also contemplates a formulation comprising a core and a coating, wherein the core comprises a pharmaceutically active ingredient and the coating comprises or is a water-soluble cellulose ether. The coating is present in an amount to provide a % in solution of more than 60% of the pharmaceutically active ingredient at 1 hour from the start of a dissolution test to measure the % in solution of the pharmaceutically active ingredient in a dissolution medium consisting of water, the dissolution test being carried out in accordance with USP <711> Dissolution using Apparatus II (paddle apparatus) operated with a paddle speed of 75 rpm and with the dissolution medium at a temperature of 37° C.±0.5° C. Alternatively, the % in solution of the active ingredient may be more than 65%, 70%, 75%. The % in solution may also be selected from a range from: 60% to 90%, 65% to 85%, 68% to 83%, 68% to 73%, 72% to 78%, 75% to 85%, or 77% to 83%, 68% to 78% preferably 68% to 83%.

In combination with or as an alternative to any of the amounts of % in solution disclosed in the preceding paragraph the coating may be present in an amount to additionally or alternatively provide a % in solution of: more than 35%, 38%, 48%, 50%, 60%, 65%, 70% or 75% at 0.5 hours from the start of the dissolution test; and/or more than 75% at 1.5 hours.

It is contemplated within this aspect of the invention that the coating may further be present in an amount corresponding to a % weight gain by weight of the core of: from 1% to 15%, from 1% to 12%, from 2% to 15%, from 2% to 12%, from 1% to 9%, from 2% to 8%, from 2% to 3%, from 2% to 5%, from 5% to 7%, from 4% to 6.5%, from 6% to 7%, or from 2% to 7%. Preferably, the coating may be present in an amount corresponding to a weight gain of from 1% to 9%, from 2% to 8%, from 4% to 6.5%, from 2% to 5% or from 2% to 7%, optionally from 4% to 6.5%, from 2% to 5% or from 2% to 7%. The % weight gain of the coating relative to the core may be combined with any of the specified % in solution values and any time point.

For example, the coating may be present in an amount to provide a % in solution of more than 70%, optionally more than 75% or from 70% to 90% or from 75% to 85%, of the pharmaceutically active ingredient at 1 hour, and the coating may be present in an amount corresponding to a % weight gain by weight of the core of from 2% to 7%, optionally from 2% to 4% or 5% to 6%. Alternatively, the coating may be present in an amount to provide a % in solution of more than 65%, optionally more than 68% or from 65% to 90% or from 68% to 78%, of the pharmaceutically active ingredient at 1 hour, and the coating may be present in an amount corresponding to a % weight gain by weight of the core of from 9% to 20%, optionally from 9% to 16% or 10% to 15%.

Also contemplated by the invention is a pharmaceutical formulation comprising a core and a coating, wherein the core comprises a pharmaceutically active ingredient, optionally a hydrophobic active ingredient, and the coating comprises or is a water-soluble cellulose ether. The coating is present in an amount to provide a % in solution of the pharmaceutically active ingredient of more than 75%, optionally 80%, at 12 hours from the start of a dissolution test in a dissolution medium consisting of water, the dissolution test being carried out in accordance with USP <711> Dissolution using Apparatus II (paddle apparatus) operated with a paddle speed of 75 rpm and with the dissolution medium at a temperature of 37° C.±0.5° C. In an alternative or in addition to the coating being present in an amount to provide a % in solution of the pharmaceutically active ingredient of more than 75% at 12 hours, the coating may be present in an amount to provide a % in solution of the pharmaceutically active ingredient of: more than 70%, (for example more than 75% or 80%) at 14 hours; more than 60% (for example more than 65%, 70% or 75%) at 16 hours; more than 50% (for example more than 55%, 60%, 65%, or 70%) at 18 hours; more than 40% (for example more than 45%, 50%, 55%, 60%, 65% or 70%) at 20 hours; more than 40% (for example more than 45%, 50%, 55%, 60%, 65% or 70%) at 22 hours; or 35% (for example more than 40%, 45%, 50%, 55%, 60%, or 65%) at 24 hours. In an embodiment the coating is present in an amount to provide a % in solution specified in this paragraph at one or more of the time points specified in this paragraph.

For example, in an embodiment the % in solution is more than 75% at 12 hours and more than 35%, optionally more than 50%, at 24 hours. Alternatively, the % in solution is more than 80% at 12 hours and more than 50% at 24 hours. The % in solution may be more than 75% at 12 hours and more than 70% at 14 hours. The % in solution may be more than 75% at 12 hours and more than 60% at 16 hours. The % in solution may be more than 75% at 12 hours and more than 50% at 18 hours. The % in solution may be more than 75% at 12 hours and more than 40% at 20 hours. The % in solution may be more than 75% at 12 hours and more than 40% at 22 hours. The % in solution may be more than 75% at 12 hours, more than 60% at 16 hours and more than 35% at 24 hours. The % in solution may be more than 75% at 12 hours, more than 70% at 14 hours, more than 60% at 16 hours, more than 50% at 18 hours, more than 40% at 20 hours, more than 40% at 22 hours, and more than 35% at 24 hours.

It is contemplated within this aspect of the invention that the coating may further be present in an amount corresponding to a % weight gain by weight of the core of: from 7% to 20%, from 8% to 20%, from 9% to 20%, from 8% to 17%, from 8% to 16%, from 9% to 16%, from 10% to 15%, from 12% to 17%, from 8% to 12%, or from 9% to 12%. Preferably, the coating may be present in an amount corresponding to a weight gain of from 9% to 16%, from 10% to 15%, from 12% to 17%, from 8% to 12%, or from 9% to 12%, optionally from 9% to 16%, or from 10% to 15%. The % weight gain of the coating relative to the core may be combined with any of the specified % in solution values and any time point.

For example, the coating may be present in an amount to provide a % in solution of more than 70%, optionally more than 75% or 80%, of the pharmaceutically active ingredient at 12 hours, and the coating may be present in an amount corresponding to a % weight gain by weight of the core of from 9% to 16%, from 10% to 15%, from 12% to 17%, from 8% to 12%, or from 9% to 12%, optionally from 9% to 16%, or from 10% to 15%. Alternatively, the coating may be present in an amount to provide a % in solution of more than 70%, optionally more than 75% or 80%, of the pharmaceutically active ingredient at 12 hours and more than 50%, optionally more than 50%, 55%, 65%, 70% or 75%, at 16 hours, and the coating may be present in an amount corresponding to a % weight gain by weight of the core of from 9% to 16%, from 10% to 15%, from 12% to 17%, from 8% to 12%, or from 9% to 12%, optionally from 9% to 16%, or from 10% to 15%. Further similar combinations of features are contemplated by the invention.

Also contemplated by the invention is a pharmaceutical formulation comprising a core and a coating, wherein the core comprises a pharmaceutically active ingredient, optionally a hydrophobic active ingredient, and the coating comprises or is a water-soluble cellulose ether. The coating is present in an amount to provide a higher % in solution of the pharmaceutically active ingredient from the formulation than a corresponding formulation without the coating at 12 hours from the start of a dissolution test in a dissolution medium consisting of water, the dissolution test being carried out in accordance with USP <711> Dissolution using Apparatus II (paddle apparatus) operated with a paddle speed of 75 rpm and with the dissolution medium at a temperature of 37° C.±0.5° C. In an alternative or in addition to the coating being present in an amount to provide a higher % in solution of the pharmaceutically active ingredient at 12 hours, the higher % in solution of the active ingredient from the formulation may be at 10, 11, 13, 14, 15, 16, 17, 18, 19, 20, 21, 22, 23, 24 hours or any combination of one or more thereof, from the start of a dissolution test.

A hydrophobic active ingredient is any active that is substantially insoluble in water. The active may have some solubility in water. Therefore, a hydrophobic active ingredient is one which is more readily soluble in a non-aqueous phase as opposed to water. In addition a hydrophobic active ingredient may be an active that falls within Class II or Class IV of the Biopharmaceutics Classification System, these classes containing highly permeable, low solubility drugs and low permeability, low solubility drugs respectively. Solubilities of components of the invention, e.g. active entities, functional components, etc., in a solvent (for example water) may be defined as follows, the solubility being measured at 25° C. and parts being by weight:

| Descriptive Team | Parts of Solvent for 1 part of solute |
|---|---|
| Very Soluble | Less than 1 |
| Freely Soluble | From 1 to 10 |
| Soluble | From 10 to 30 |
| Sparingly Soluble | From 30 to 100 |
| Slightly Soluble | From 100 to 1000 |
| Very Slightly Soluble | From 1000 to 10,000 |
| Practically Insoluble | More than 10,000 |

In embodiments the coating is present in an amount to provide a higher % in solution of the pharmaceutically active ingredient from the formulation than for a corresponding formulation without the coating at time points selected from the following combinations: 12 hours and 10 hours; 12 hours and 14 hours; 12 hours and 14 hours and 16 hours; 12 hours, 14 hours, 16 hours and 18 hours; and 12 hours, 14 hours, 16 hours, 18 hours and 20 hours.

In embodiments the coating is present in an amount to provide a higher % in solution of the pharmaceutically active ingredient from the formulation than for a corresponding formulation without the coating for a period selected from one of those spanning from: 8 hours to 16 hours, 10 to 16 hours; 10 to 18 hours; 10 to 24 hours; 12 to 18 hours; 12 to 22 hours; 12 to 24 hours; 4 to 24 hours; and 0 to 24 hours, preferably 12 to 24 hours.

In addition, the % in solution for a formulation with the coating may be higher than for a corresponding formulation without the coating at a specific time point by more than: 5 or 10 at 12 hours; 5, 10, or 15 at 14 hours; 5, 10, 15, 20, or 25 at 16 hours; 5, 10, 15, 20, 25, or 30 at 18 hours; 5, 10, 15, 20, 25, 30, or 35 at 20 hours; 5, 10, 15, 20, 25, 30, or 35 at 22 hours; and/or 5, 10, 15, 20, 25, 30, 35, or 40 at 24 hours. The higher values of % in solution described herein may be attained when a single time point is specified, more than one time point is specified or where a period is specified.

For example, the % in solution for a formulation with the coating may be higher than for a corresponding formulation without the coating by more than: 5 (optionally 10) at 12 hours; or 5 (optionally 10) at 12 hours and 10 (optionally 15) at 14 hours; or 5 (optionally 10) at 12 hours, 10 (optionally 15) at 14 hours, and 15 (optionally 20) at 16 hours; or 5 (optionally 10) at 12 hours, 10 (optionally 15) at 14 hours, 15 (optionally 20) at 16 hours, and 20 (optionally 25) at 18 hours; or 5 (optionally 10) at 12 hours, 10 (optionally 15) at 14 hours, 15 (optionally 20) at 16 hours, 20 (optionally 25) at 18 hours, and 25 (optionally 30) at 20 hours; or 5 (optionally 10) at 12 hours, 10 (optionally 15) at 14 hours, 15 (optionally 20) at 16 hours, 20 (optionally 25) at 18 hours, 25 (optionally 30) at 20 hours, and 20 (optionally 25) at 22 hours; or 5 (optionally 10) at 12 hours, 10 (optionally 15) at 14 hours, 15 (optionally 20) at 16 hours, 20 (optionally 25) at 18 hours, 25 (optionally 30) at 20 hours, 20 (optionally 25) at 22 hours, and 20 (optionally 30) at 24 hours. By way of illustration, the % in solution achieved by a formulation of the invention may be 50% at 12 hours and the % in solution achieved by a corresponding formulation without the coating may be 40% at 12 hours: in this case the % in solution for the formulation with the coating is higher than that for the formulation without the coating by 10.

It is contemplated within this aspect of the invention that the coating may further be present in an amount corresponding to a % weight gain by weight of the core of: from 5% to 20%, from 7% to 20%, from 8% to 20%, from 9% to 20%, from 8% to 17%, from 8% to 16%, from 5% to 16%, from 9% to 16%, from 10% to 15%, from 12% to 17%, from 8% to 12%, or from 9% to 12%. Preferably, the coating may be present in an amount corresponding to a weight gain of from 9% to 16%, from 10% to 15%, from 12% to 17%, from 8% to 12%, or from 9% to 12%, optionally from 9% to 16%, or from 10% to 15%. The % weight gain of the coating relative to the core may be combined with any of the specified % in solution values and any time point.

For example, the coating may be present in an amount to provide a higher % in solution of the pharmaceutically active ingredient at 12 hours (i.e. a higher % in solution than that achieved by a corresponding formulation without the coating), wherein the % in solution of the active may be higher by 5, optionally 10, and the coating may be present in an amount corresponding to a % weight gain by weight of the core of from 9% to 16%, from 10% to 15%, from 12% to 17%, from 8% to 12%, or from 9% to 12%, optionally from 9% to 16%, or from 10% to 15%. Alternatively, the coating may be present in an amount to provide a higher % in solution of the pharmaceutically active ingredient at 12 hours, wherein the % in solution of the active may be higher by 5, optionally 10, and by 5, optionally 10, 15, 20, or 25, at 16 hours and the coating may be present in an amount corresponding to a % weight gain by weight of the core of from 9% to 16%, from 10% to 15%, from 12% to 17%, from 8% to 12%, or from 9% to 12%, optionally from 9% to 16%, or from 10% to 15%.

The invention contemplates a pharmaceutical formulation comprising a core and a coating, wherein the core comprises a pharmaceutically active ingredient and the coating comprises or is a water-soluble cellulose ether. The coating is present in an amount to provide a decrease (compared to a corresponding formulation without the coating) in % in solution of the pharmaceutically active ingredient of 15 or less in a period from 10 hours to 16 hours from the start of a dissolution test in a dissolution medium consisting of water, the dissolution test being carried out in accordance with USP <711> Dissolution using Apparatus II (paddle apparatus) operated with a paddle speed of 75 rpm and with the dissolution medium at a temperature of 37° C.±0.5° C.

Alternatively, the period may be selected from a period from: 8 hours to 16 hours; 6 hours to 16 hours; 4 hours to 16 hours; 8 hours to 14 hours; 6 hours to 14 hours; 4 hours to 14 hours; 8 hours to 18 hours, 6 hours to 18 hours, or 4 hours to 16 hours. The decrease in % in solution may be 10 or less, 8 or less, 5 or less, or 3 or less. The decrease in % in solution may be any amount selected from 15 or less, 10 or less, or 5 or less at any time point specified.

For example, the decrease in % in solution may be 10 or less for the period of 8 to 16 hours. The decrease in % in solution may be 15 or less for the period of 4 to 18 hours. The decrease in % in solution may be 10 or less for the period of 4 to 18 hours. The decrease in % in solution may be 8 or less for the period of 4 to 18 hours. The decrease in % in solution may be 10 or less for the period of 4 to 16 hours. The decrease in % in solution may be 8 or less for the period of 4 to 16 hours. The decrease in % in solution may be 3 or less for the period of 6 to 12 hours. The decrease in % in solution may be 15 or less for the period of 6 to 16 hours. The decrease in % in solution may be 10 or less for the period of 6 to 16 hours. The decrease in % in solution may be 5 or less for the period of 6 to 16 hours.

It is contemplated within this aspect of the invention that the coating may further be present in an amount corresponding to a % weight gain by weight of the core of: from 5% to 20%, from 7% to 20%, from 8% to 20%, from 9% to 20%, from 8% to 17%, from 8% to 16%, from 9% to 16%, from 5% to 16%, from 10% to 15%, from 12% to 17%, from 8% to 12%, or from 9% to 12%. Preferably, the coating may be present in an amount corresponding to a weight gain of from 9% to 16%, from 10% to 15%, from 12% to 17%, from 8% to 12%, or from 9% to 12%, optionally from 9% to 16%, or from 10% to 15%. The % weight gain of the coating relative to the core may be combined with any of the specified % in solution values and any time point.

Throughout the disclosure of this application any change in the % in solution, for example where the % in solution is said to be higher by a certain value or the % in solution has decreased by a certain value, the value of the change has been given as a digit. This digit signifies the absolute amount that the % in solution has changed by; for example where the % in solution of the active of a formulation of the invention with the coating is said to be higher than a formulation without the coating by more than 10 means that where the % in solution of the formulation without the coating is 50% the % in solution of the formulation of the invention will be more than 60%.

Also contemplated by the invention is a pharmaceutical formulation comprising a core, a first coating and a second coating outside the first coating, wherein the core comprises a pharmaceutically active ingredient, the first coating comprises or is a water-soluble cellulose ether, further wherein the second coating comprises or is a delayed release polymer, wherein the first coating is present in an amount to provide a higher % release of the pharmaceutically active ingredient from the pharmaceutical formulation than a corresponding pharmaceutical formulation without the first coating at 12 hours from the start of a dissolution test.

Unless specified otherwise the dissolution medium used in the dissolution test of any aspect of the invention may be a dissolution medium representative of the in-vivo medium in which the formulation is to be used. Specifically, aspects of the invention where there is a first coating and a second coating. In such embodiments the dissolution test may be any dissolution test known to the person skilled in the art to represent the gastrointestinal tract. Preferably the dissolution test is carried out in accordance with USP <711> Dissolution using Apparatus II (paddle apparatus) operated with a paddle speed of 75 rpm and with the relevant dissolution medium at a temperature of 37° C.

In embodiments of the invention the dissolution test may be a two stage dissolution test and the two stage dissolution test may consist of a first stage having a dissolution medium of 750 ml 0.1N HCl into which the formulation is placed and a second stage commencing at 2 hours, wherein 250 ml 0.2M tribasic sodium phosphate containing 2% sodium dodecyl sulphate (SDS) is added to the dissolution medium and the pH adjusted to 6.8. This dissolution test may be particularly suitable for measuring release of hydrophobic actives, for example cyclosporin, from the formulation.

In other embodiments the dissolution test may consist of a dissolution medium consisting of 1000 ml of a 0.05M pH 7.5 phosphate buffer prepared by dissolving monobasic potassium phosphate and sodium hydroxide in water. This dissolution test may be particularly suitable for measuring release of hydrophilic actives, for example hydralazine and mesalamine, from the formulation. In particular the dissolution test may be the dissolution test described below: 0.05M pH 7.5 phosphate buffer prepared by dissolving 6.8 g of monobasic potassium phosphate and 1 g of sodium hydroxide in water to make 1000 mL of solution, and adjusting with 10N sodium hydroxide to a pH of 7.5±0.05; 900 mL are used in a USP Apparatus 2 with a paddle speed of 75 RPM and with the dissolution medium temperature at 37° C.±0.5° C.

In particular the two stage dissolution test was carried out in accordance with USP <711> Dissolution using Apparatus II (paddle apparatus) operated with a paddle speed of 75 rpm and with the dissolution medium at a temperature of $37°$ C.±$0.5°$ C. In the first stage of the test the dissolution medium is 750 ml of 0.1N HCl simulating the gastric environment. At the start of the test (t=0) the sample is placed in the dissolution medium. At 2 hours the second stage of the dissolution test is initiated. In the second stage 250 ml of 0.2M tribasic sodium phosphate containing 2% sodium dodecyl sulphate (SDS) is added to the dissolution medium and the pH adjusted to 6.8±0.05 using 2N NaOH or 2N HCl as required.

In any of the formulations comprising a first coating and second coating, the first coating may be present in an amount to provide a higher % release of the pharmaceutically active ingredient at any point in time after 3 hours from the start of the dissolution test. For example, the higher % release may be at 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours or 24 hours. The higher % release may be at one or more of the time points, preferably one or more consecutive time points.

For example, the higher % release may be at: 3 hours and 4 hours; 3 hours, 4 hours and 5 hours; 3 hours, 4 hours, 5 hours, 11 hours, 12 hours, and 13 hours; 11 hours 12 hours, and 13 hours; or 11 hours, 12 hours, 13 hours, 14 hours, 20 hours, 21 hours 22 hours and 24 hours.

The higher % release may be for a period selected from one or a combination of periods of from: 11 to 12 hours, 11 to 13 hours, 12 to 13 hours, 11 to 14 hours, 10 to 14 hours, 18 to 22 hours, 20 to 24 hours, 4 to 8 hours, 3 to 8 hours, 3 to 12 hours, 3 to 6 hours, 8 to 14 hours, 8 to 18 hours, 8 to 22 hours, 6 to 22 hours, 8 to 24 hours, 4 to 14 hours, 4 to 18 hours 4 to 22 hours, 4 to 24 hours, 3 to 20 hours, 3 to 22 hours or 3 to 24 hours.

In addition, the % in solution for a formulation with the coating may be higher than for a corresponding formulation without the coating at a specific time point by more than: 5, 10, 15, 20 or 25 at 12 hours; 5, 10, 15, or 20 at 14 hours; 5, 10, 15, or 20 at 16 hours; 5, 10, 15, or 20 at 18 hours; 5, 10 or 15 at 20 hours; 5 or 10 at 22 hours; 5 or 10 at 24 hours; 5, 10, 15, 20 or 25 at 10 hours; 5, 10, 15, or 20 at 8 hours; 5, 10, 15, or 20 at 6 hours; 5 or 10 at 4 hours. The higher values of % in solution described herein may be attained when a single time point is specified, more than one time point is specified or where a period is specified.

For example, the % in solution for a formulation with the coating may be higher than for a corresponding formulation without the coating by more than: 5 (optionally 10, 15, 20 or 25) at 12 hours; or 5 (optionally 10, 15, 20 or 25) at 12 hours and 5 (optionally 10, 15 or 20) at 14 hours; or 5 (optionally 10, 15, 20 or 25) at 10 hours and 5 (optionally 10, 15, 20 or 25) at 12 hours; or 5 (optionally 10, 15, or 20) at 8 hours 5 (optionally 10, 15, 20 or 25) at 10 hours and 5 (optionally 10, 15, 20 or 25) at 12 hours; or 5 (optionally 10, 15, or 20) at 6 hours, 5 (optionally 10, 15, or 20) at 8 hours or 5 (optionally 10, 15, 20 or 25) at 10 hours and 5 (optionally 10, 15, 20 or 25) at 12 hours; or 5 (optionally 10, 15, 20 or 25) at 12 hours, 5 (optionally 10, 15, or 20) at 14 hours, and 5 (optionally 10, 15, or 20) at 16 hours; or 5 (optionally 10, 15, 20 or 25) at 10 hours, 5 (optionally 10, 15, 20 or 25) at 12 hours, and 5 (optionally 10, 15, or 20) at 14 hours; or 5 (optionally 10, 15, 20 or 25) at 10 hours, 5 (optionally 10, 15, 20 or 25) at 12 hours, 5 (optionally 10, 15, or 20) at 14 hours and 5 (optionally 10, 15, or 20) at 16 hours; or 5 (optionally 10, 15, 20 or 25) at 12 hours, 5 (optionally 10, 15, or 20) at 14 hours, 5 (optionally 10, 15, or 20) at 16 hours, and 5 (optionally 10, 15, or 20) at 18 hours; or 5 (optionally 10, 15, 20 or 25) at 10 hours, 5 (optionally 10, 15, 20 or 25) at 12 hours, 5 (optionally 10, 15, or 20) at 14 hours, 5 (optionally 10, 15, or 20) at 16 hours, and 5 (optionally 10, 15, or 20) at 18 hours; or 5 (optionally 10, 15, or 20) at 8 hours or 5 (optionally 10, 15, 20 or 25) at 10 hours, 5 (optionally 10, 15, 20 or 25) at 12 hours, 5 (optionally 10, 15, or 20) at 14 hours, 5 (optionally 10, 15, or 20) at 16 hours, and 5 (optionally 10, 15, or 20) at 18 hours; or 5 (optionally 10, 15, or 20) at 6 hours, 5 (optionally 10, 15, or 20) at 8 hours, 5 (optionally 10, 15, 20 or 25) at 10 hours, 5 (optionally 10, 15, 20 or 25) at 12 hours, 5 (optionally 10, 15, or 20) at 14 hours, 5 (optionally 10, 15, or 20) at 16 hours, and 5 (optionally 10, 15, or 20) at 18 hours, and 5 (optionally 10 or 15) at 20 hours; or 5 (optionally 10, 15, 20 or 25) at 12 hours, 5 (optionally 10, 15, or 20) at 14 hours, 5 (optionally 10, 15, or 20) at 16 hours, and 5 (optionally 10, 15, or 20) at 18 hours, 5 (optionally 10 or 15) at 20 hours, and 5 (optionally 10) at 22 hours; or 5 (optionally 10, 15, 20 or 25) at 12 hours, 5 (optionally 10, 15, or 20) at 14 hours, 5 (optionally 10, 15, or 20) at 16 hours, and 5 (optionally 10, 15, or 20) at 18 hours, 5 (optionally 10 or 15) at 20 hours, 5 (optionally 10) at 22 hours, and 5 (optionally 10) at 24 hours; or 5 (optionally 10) at 12 hours, 10 (optionally 15) at 14 hours, 15 (optionally 20) at 16 hours, 20 (optionally 25) at 18 hours, 25 (optionally 30) at 20 hours, and 20 (optionally 25) at 22 hours; or 5 (optionally 10) at 12 hours, 10 (optionally 15) at 14 hours, 15 (optionally 20) at 16 hours, 20 (optionally 25) at 18 hours, 25 (optionally 30) at 20 hours, 20 (optionally 25) at 22 hours, and 20 (optionally 30) at 24 hours.

The invention also contemplates a pharmaceutical formulation comprising a core, a first coating and a second coating outside of the first coating, wherein the core comprises a pharmaceutically active ingredient, the first coating comprises or is a water-soluble cellulose ether, further wherein the second coating comprises or is a delayed release polymer, wherein the first coating is present in an amount to provide a % release of the pharmaceutically active ingredient of more than 50%, optionally more than 55% and 60% (for example more than 65%, 70%, 75%, 80%, 85% or 90%) at 12 hours from the start of a dissolution test, wherein the dissolution test is described above.

The first coating may be present in an amount to provide a % release of the pharmaceutically active ingredient at 12 hours of from: 70% to 95%, 75% to 95%, 70% to 90%, 75% to 90%, 70% to 85%, 70% to 80%, or 75% to 85%, preferably 75% to 95%, 80% to 95% or from 85% to 95%.

The first coating may further be present in an amount to provide a % release of the pharmaceutically active ingredient in an amount of more than 40%, (optionally more than 45% or more than 50%) at 6 hours or 4 hours from the start of the dissolution test. The % release of the pharmaceutically active ingredient may be in an amount of from 40% to 65% (optionally 45% to 65%) at 6 hours or 4 hours from the start of the dissolution test. Optionally, the first coating may be present in a weight gain of from 1% to 20% and the second coating may be present in a weight gain of from 4% to 25%, optionally from 4% to 15%, from 4% to 12%, from 15% to 25% from 4% to 6% or 8% to 13%. Where the % release is 20% or more (optionally 45% or more) at 4 hours the second coating is preferably present in a weight gain of at least 4%, preferably no more than 25% and optionally 4% to 6%. Where the % release is 40% or more (optionally 45% or more) at 6 hours the second coating is preferably present in a weight gain of at least 4%, preferably no more than 25% and optionally 8% to 13%.

The first coating may further or alternatively be present in an amount to provide a % release of the pharmaceutically active ingredient in an amount of more than 15% (for example more than 20%, 25%, 28% or 30%), optionally from 25% to 40% or from 25% to 35%, at 4 hours from the start of the dissolution test. Optionally, the first coating may be present in a weight gain of from 1% to 20% and the second coating may be present in a weight gain of from 4% to 15%, optionally from 4% to 6% or 8% to 13%.

The first coating may be present in an amount to provide a % release of the pharmaceutically active ingredient in an amount of more than 25%, optionally from 25% to 40% or 25% to 35%, at 6 hours. Optionally, the first coating may be present in a weight gain of from 1% to 20% and the second coating may be present in a weight gain of from 4% to 15%, optionally from 4% to 6% or 8% to 13%. Where the % release of the active ingredient is more than 25%, optionally from 25% to 40% or 25% to 35%, at 6 hours the active ingredient may be a hydrophilic active ingredient, for example mesalamine, optionally suspended in the disperse phase. The disperse phase is described in more detail below.

In embodiments the % release at 12 hours may be more than 80%, wherein the first coating may be present in a weight gain of from 1% to 20% and the second coating may be present in a weight gain of from 4% to 15%, optionally from 4% to 6% or 8% to 13%.

In embodiments the active ingredient is a hydrophobic active, for example cyclosporin A. In embodiments the active ingredient is a hydrophobic active, for example cyclosporin A and the % release is more than 70% (optionally 75% or 80%) at 12 hours. Optionally, the first coating may be present in an amount corresponding to a weight gain due to the coating of from 0.5% to 20% by weight of the core (optionally from 1% to 16%, from 4% to 16%, from 4% to 12%, or from 3% to 6%) and/or the second coating is present in an amount corresponding to a weight gain due to the second coating of from 2% to 20% by weight. (optionally 4% to 20%, 4% to 15%, 8% to 18%, or 8% to 12%).

In any aspect of the invention and any embodiment the core may comprise a hydrogel forming polymer matrix. The hydrogel forming polymer matrix may be as described below.

The core of a pharmaceutical formulation of any aspect or embodiment of the invention may be in the form of a solid colloid. The colloid comprises a continuous phase and a disperse phase. Suitable continuous phases and disperse phases which may be used to form the core are defined in more detail below and in the detailed description of the invention. The continuous phase may comprise or be the hydrogel forming polymer matrix. Hence, where the continuous phase is the hydrogel forming polymer matrix, the formulation of the invention may take the form of a solid unit of the hydrogel forming polymer comprising a disperse phase. The disperse phase may be droplets dispersed in the continuous phase, or the hydrogel forming polymer matrix. The disperse phase may comprise or be a hydrophobic phase.

The continuous phase of a solid colloid core is or comprises a hydrogel-forming polymer matrix. In embodiments the hydrogel-forming polymer matrix is or comprises a hydrocolloid, a non-hydrocolloid gum or chitosan. In a particular embodiment the hydrogel-forming polymer matrix is or comprises gelatin, agar, a polyethylene glycol, starch, casein, chitosan, soya bean protein, safflower protein, alginates, gellan gum, carrageenan, xanthan gum, phthalated gelatin, succinated gelatin, cellulosephthalate-acetate, oleoresin, polyvinylacetate, polymerisates of acrylic or methacrylic esters and polyvinylacetate-phthalate and any derivative of any of the foregoing; or a mixture of two or more such polymers. In a further embodiment the hydrogel-forming polymer matrix is or comprises a hydrocolloid selected from carrageenan, gelatin, agar and pectin, or a combination thereof optionally selected from gelatin and agar or a combination thereof. Particularly, the polymer of the hydrogel-forming polymer matrix is or comprises gelatin. In an embodiment, the hydrogel-forming polymer does not comprise a cellulose or a cellulose derivative, e.g. does not comprise a cellulose ether.

In this aspect of the invention the core may be in the form of a solid colloid the colloid comprising a continuous phase and a disperse phase and the pharmaceutically active ingredient may be in solution or suspended in the disperse phase. For example, the active ingredient may be a hydrophobic active ingredient in solution in the disperse phase or a hydrophilic active ingredient suspended in the disperse phase.

In embodiments of this aspect of the invention the active ingredient may be a hydrophobic active ingredient, for example cyclosporin, and the active ingredient may be in solution in the disperse phase. The first coating may be present in a weight gain of from 0.5% to 20% and the second coating may be present in a weight gain of from 8% to 12% and the first coating is present in an amount to provide a % release of 80% or more. Optionally, the water-soluble cellulose ether may be hydroxyl propyl methyl cellulose.

In a further aspect the invention contemplates a pharmaceutical formulation comprising a core, a first coating and a second coating outside of the first coating, wherein the core comprises a pharmaceutically active ingredient, the first coating comprises or is a water-soluble cellulose ether, further wherein the second coating comprises or is a delayed release polymer, wherein the first coating is present in an amount to provide a % release of the pharmaceutically active ingredient of more than 70%, (for example more than 75% or 80%) at 6 hours from the start of a dissolution test, wherein the dissolution test is as described above.

In embodiments the first coating is present in an amount to provide a % release of from 75% to 95% or from 80% to 90% of the pharmaceutically active ingredient at 6 hours.

The second coating may be present in an amount to provide a weight gain of 2% to 20%, 5% to 15%, 8% to 12%, 2% to 8%, 3% to 7%, or 4% to 6%.

The active ingredient may be a hydrophobic active ingredient, for example cyclosporin A. The active ingredient may be in solution in the disperse phase.

The invention also contemplates a pharmaceutical formulation comprising a core, a first coating and a second coating outside of the first coating, wherein the core comprises a pharmaceutically active ingredient, optionally a hydrophilic active ingredient, the first coating comprises or is a water-soluble cellulose ether, further wherein the second coating comprises or is a delayed release polymer, wherein the first coating is present in an amount to provide a % release of the pharmaceutically active ingredient of more than 30% (for example more than 35%, 40%, 45%, 50%, 55% or 60%) at 12 hours from the start of a dissolution test, wherein the dissolution test is as described above.

The first coating may be present in an amount to allow release of from 30% to 80%, optionally 30% to 70%, 35% to 70%, 40% to 70%, 40% to 50% or 60% to 70% of the active ingredient at 12 hours.

The first coating may be present in a weight gain selected from a range of from: 1% to 20%, 4% to 7%, 5% to 7%, 4% to 15%, 4% to 12% and 8% to 12%. The second coating may be present in a weight gain selected from a range of from: 8% to 12%.

The active ingredient may be in solution in the continuous phase of the formulation, where the formulation is in the form of a solid colloid comprising a continuous phase and a disperse phase. The active ingredient may be a hydrophilic active ingredient, for example mesalazine or hydralazine, which is in solution in the continuous phase. In embodiments the active ingredient is a hydrophilic active in solution in the continuous phase, the first coating is present in an amount to provide a % release of 35% to 50% and a weight gain of 4% to 7%, and the second coating is present in a weight gain of 8% to 12%. In alternative embodiments the active ingredient is a hydrophilic active in solution in the continuous phase, the first coating is present in an amount to provide a % release of 55% to 75% and a weight gain of 8% to 12%, and the second coating is present in a weight gain of 8% to 12%.

It is to be understood that the individual embodiments described above may be combined with one or more of the other embodiments described to provide further embodiments of the invention defined by for example a combination of one or more of the embodiments to the time points, time periods, % in solution, % released, values of the increase of higher % in solution, values of the increase of higher % released.

The first coating may be in contact with the core. The second coating may be on the first coating. In embodiments the first coating is in contact with the core and the second coating is on the first coating.

The second coating may be or may comprise a delayed release polymer and the delayed release polymer may be selected from an enteric polymer, a pH independent polymer, a pH dependent polymer and a polymer specifically susceptible to degradation by bacterial enzymes in the gastrointestinal tract, or a combination of two or more such polymers. Hence, the second coating may be any of the aforementioned delayed release polymers or any may be or possess the characteristics mentioned in relation to the delayed release polymer mentioned below.

In embodiments the delayed release polymer may be water-soluble or water-permeable in an aqueous medium with a pH greater than 6.5. The delayed release polymer may be or comprise a pH-independent polymer, for example ethyl cellulose.

In any aspect and any embodiment of the invention the water-soluble cellulose ether may be selected from any one or a combination of: methyl cellulose, hydroxyethyl cellulose, hydroxypropyl cellulose and hydroxypropyl methylcellulose. The water-soluble cellulose ether may preferably be hydroxylpropyl methylcellulose.

In embodiments the first coating may be or comprise hydroxypropyl methyl cellulose and the second coating may be or comprise ethyl cellulose.

It is contemplated within any aspect or embodiment where there is a first coating and a second coating that the first coating may be present in a % weight gain relative to the core of from 0.5% to 20%. In addition the first coating may be present in an amount corresponding to a weight gain due to the coating selected from ranges of from: 0.5% to 15%; 1% to 15%; 1% to 12%; 1% to 10%; 1% to 8%; 1% to 6%; 1% to 4%, 2% to 10%; 2% to 8%; 2% to 6%; 2% to 7%; 2% to 4%; 4% to 8%; 4% to 7%, 4% to 6%, 5% to 7%; 7% to 20%; 7% to 16%; 9% to 20%; 9% to 16%; 10% to 15%; and 12% to 16%.

It is contemplated within any aspect or embodiment where there is a first coating and a second coating that the second coating may be present in a % weight gain of from 2% to 40%. In addition the second coating may be present in an amount corresponding to a weight gain due to the coating selected from ranges of from: 4% to 30%, 4% to 7%, 7% to 40%, 7% to 30%, 8% to 25%, 8% to 20%, 2% to 25%, 2% to 20%, 4% to 25%, 4% to 20%, 4% to 15%, 4% to 13%, 7% to 15%, 7% to 13%, 8% to 12%, 9% to 12% and 20% to 25%.

Throughout the disclosure of this application the weight gain of the first coating is given as a % by weight of the core and the weight gain of the second coating is given as a % by weight of the formulation that is coated by the second coating, for example the core and the first coating.

In any aspect and embodiment of the invention the first coating may be present in a % weight gain relative to the core of from 0.5% to 20%, preferably 1% to 16% or 4% to 16%, and the second coating may be present in a % weight gain of 4% to 24%, 7% to 24%, 22% to 24%, 7% to 15%, or 8% to 12%, preferably 22% to 24%, 7% to 15%, or 8% to 12%.

The hydrogel forming polymer may be or comprise a hydrocolloid, a non-hydrocolloid gum or chitosan. The hydrogel forming polymer may be a reversible hydrocolloid, for example a thermoreversible hydrocolloid or a thermoreversible hydrogel forming polymer. Alternatively, the hydrogel forming polymer may be or comprise an irreversible hydrocolloid. The hydrogel forming polymer matrix may be or comprise gelatin, agar, a polyethylene glycol, starch, casein, chitosan, soya bean protein, safflower protein, alginates, gellan gum, carrageenan, xanthan gum, phthalated gelatin, succinated gelatin, cellulosephthalate-acetate, oleoresin, polyvinylacetate, polymerisates of acrylic or methacrylic esters and polyvinylacetate-phthalate and any derivative of any of the foregoing; or a mixture of one or more such a hydrogel forming polymers. The hydrogel forming polymer matrix may be or comprise a hydrocolloid selected from carrageenan, gelatin, agar and pectin, or a combination thereof optionally selected from gelatin and agar or a combination thereof, more optionally the polymer of the a hydrogel forming polymer matrix is or comprises gelatin. The hydrogel forming polymer matrix is or comprises a non-hydrocolloid gum optionally selected from a cross-linked salt of alginic acid. In preferred embodiments the hydrogel forming polymer is or comprises gelatin.

In embodiments the hydrogel forming polymer further comprising a plasticiser, optionally a plasticiser selected from glycerin, a polyol for example sorbitol, polyethylene glycol and triethyl citrate or a mixture thereof, particularly sorbitol.

The hydrogel forming polymer matrix may encapsulate the active ingredient. The active ingredient may be encapsulated as a suspension in the hydrogel forming polymer matrix or in solution. The active ingredient may be in solution or suspended in another component, for example a hydrophobic phase or the disperse phase discussed elsewhere, of the formulation that is also encapsulated by the hydrogel forming polymer matrix.

The core of the pharmaceutical formulation of the invention may be in the form of a solid colloid the colloid comprising a continuous phase and a disperse phase, wherein the continuous phase optionally comprises the hydrogel forming polymer matrix. Hence the pharmaceutical formulation of all aspects of the invention may comprise at least the following features a core and a first coating, wherein the core comprises an active ingredient and is in the form of a solid colloid comprising a continuous phase and a disperse phase, and the coating comprises or is a water soluble cellulose ether. The continuous phase may be formed of the hydrogel forming polymer matrix.

In embodiments the active ingredient is or is comprised in the disperse phase of the core. In embodiments, the active ingredient is comprised in the continuous phase of the core. In embodiments, a first active ingredient is or is comprised in the disperse phase of the core and a second active ingredient is comprised in the continuous phase of the core.

The disperse phase may be solid, semi-solid or liquid. In particular, the disperse phase may be liquid. In other particular instances the disperse phase may be semi-solid, for example it may be waxy.

The disperse phase may be a hydrophobic phase, for example a hydrophobic phase which is a solid, a semi-solid or a liquid. Suitably the disperse phase is or comprises a liquid lipid and optionally a solvent miscible therewith.

The active ingredient may be dissolved in the disperse phase. The active ingredient may be suspended in the disperse phase. The disperse phase may be as described elsewhere herein, for example it may be as described in the immediately preceding two paragraphs.

In a particular embodiment the disperse phase is or comprises a liquid lipid and a solvent, wherein the solvent is miscible with the liquid lipid and water, optionally wherein the solvent is selected from 2-(2-ethoxyethoxy) ethanol and a poly(ethylene glycol), particularly wherein the solvent is 2-(2-ethoxyethoxy)ethanol. In a further embodiment the disperse phase is or comprises an oil phase comprising a medium chain mono- di- or triglyceride (particularly a medium chain triglyceride), a polyethoxylated castor oil and 2-(ethoxyethoxy)ethanol. The disperse phase as described in this paragraph may contain a hydrophobic active ingredient, for example, cyclosporin A, or a hydrophobic active ingredient, for example mesalazine.

In embodiments the formulation further comprises one or more surfactants, suitable surfactants are described in more detail in the detailed description of the invention. In those embodiments where the formulation comprises a core in the form of a solid colloid, the colloid comprising a continuous phase and a disperse phase, wherein the continuous phase comprises the hydrogel-forming polymer matrix, surfactant may be present in the continuous phase, the disperse phase or both the continuous phase and the disperse phase. Accordingly in one embodiment the core further comprises a surfactant present in at least the continuous phase, the surfactant having an HLB value of greater than 10, for example greater than 20. In a further embodiment the disperse phase further comprises a surfactant with an HLB value in the range of from 1 to 10, for example from 1 to 5.

The core may have the characteristics of a core formed by mixing a disperse phase with a continuous phase to form a colloid, wherein the continuous phase is an aqueous phase comprising hydrogel forming polymer and the disperse phase is a hydrophobic phase, wherein the pharmaceutically active ingredient is in the continuous phase or the disperse phase, wherein the colloid is gelled to form the core.

The active ingredient may be a hydrophobic active ingredient or a hydrophilic active ingredient. The active ingredient may be present in the core in solution or in suspension and this is true for when the disperse phase or the continuous phase comprises the active ingredient. In embodiments where the active ingredient is a hydrophobic active ingredient it may be in solution in the disperse phase, for example where the disperse phase is or comprises a hydrophobic phase, a liquid lipid, an oil, a polyunsaturated fatty acid or a solvent, or suspended in the continuous phase. In embodiments where the active ingredient is a hydrophilic active ingredient it may be suspended in the disperse phase, for example where the disperse phase is or comprises a hydrophobic phase, a liquid lipid, an oil, a polyunsaturated fatty acid or a solvent, or in solution in the continuous phase.

The core of the formulation may comprise a hydrogel-forming polymer matrix and a pharmaceutically active ingredient and have the characteristics of a core obtained by a process comprising:
(i) dissolving a hydrogel-forming polymer in an aqueous liquid to form an aqueous solution;
(ii) dissolving or dispersing the active ingredient in a liquid to form a solution or dispersion (particularly a solution) of the active ingredient in the liquid;
(iii) mixing the aqueous solution (i) and the solution or dispersion (ii) to form a colloid;
(iv) ejecting the colloid through a nozzle to form droplets;
(v) causing or allowing the a hydrogel-forming polymer to gel or solidify to form a hydrogel-forming polymer matrix; and
(vi) drying the solid.

In a variant, the core of the formulation may comprise a hydrogel-forming polymer matrix and a pharmaceutically active ingredient and have the characteristics of a core obtained by a process comprising:
(i) dissolving in an aqueous liquid a hydrogel-forming polymer and the active ingredient to form an aqueous solution;
(ii) mixing the aqueous solution (i) and a second liquid to form a colloid;
(iii) ejecting the colloid through a nozzle to form droplets;
(iv) causing or allowing the a hydrogel-forming polymer to gel or solidify to form a hydrogel-forming polymer matrix; and
(v) drying the solid.

The active ingredient used in all methods described in this specification may be one described herein, for example it may be hydrophilic or it may be hydrophobic. It may be selected from the hydrophilic active ingredients described herein. It may be selected from the hydrophobic active ingredients described herein.

Suitably the aqueous phase pre-mix (i) further comprises an anionic surfactant, e.g. as described elsewhere herein, for example sodium dodecyl sulphate (SDS).

In one embodiment the core having the characteristics of a core obtained by the process above is a core comprising a hydrogel-forming polymer matrix and a non-aqueous phase dispersed in the hydrogel-forming polymer matrix, wherein the core is or comprises gelatin, SDS, sorbitol, polyethoxylated castor oil, caprylic/capric triglyceride, 2-(ethoxyethoxy)ethanol; wherein the aqueous solution (i) is or comprises gelatin, sorbitol and SDS; and the solution or dispersion (ii) is or comprises polyethoxylated castor oil, caprylic/capric triglyceride, 2-(ethoxyethoxy)ethanol and the active ingredient.

The core of the formulation may alternatively comprise a hydrogel-forming polymer matrix and a pharmaceutically active ingredient and have the characteristics of a core obtained by a process comprising:

(a) dissolving a hydrogel-forming polymer in an aqueous liquid to form an aqueous solution;

(b) before, during or after dissolving the hydrogel-forming polymer in the aqueous liquid, mixing the active ingredient in the aqueous liquid;

(c) then ejecting the aqueous liquid comprising the hydrogel-forming polymer and the active ingredient through a nozzle to form droplets;

(d) causing or allowing the a hydrogel-forming polymer to gel or solidify to form a hydrogel-forming polymer matrix; and (e) drying the solid.

In the method of the immediately preceding paragraph, the active ingredient may be dissolved in the aqueous liquid or, for example, it may be dispersed in the aqueous liquid in particulate form.

Cores having the characteristics of cores obtained by the above-described processes, for example cores obtained by the processes, are coated to provide a coating that comprises or is a water-soluble cellulose ether, optionally with a second coating to control or modify release, preferably a polymeric coating as described above and herein. The coated formulation may be obtained by applying to the core the coating, e.g. applying to the core first and second coatings as described. Before the coating is applied, the core may be made by a process having steps (i) to (vi), (i) to (v) or (a) to (e) described above. Suitable methods for applying the coating(s) are described below and include applying the coatings by spray coating a coating formulation onto the core. The processes having steps (i) to (vi), (i) to (v) or (a) to (e) themselves form aspects of the invention.

The active ingredient may be an immunosuppressant, a hydroxylase inhibitor, or an anti-inflammatory; optionally the active ingredient is cyclosporin A, hydralazine or mesalazine. Cyclosporin or mesalamine may conveniently be used for example in a process having steps (i) to (vi) described above. Hydralazine may conveniently be used for example in a process having steps (i) to (vi), (i) to (v) or (a) to (e) described above, in particular a process having steps (i) to (v) above.

The core may further comprise a surfactant, optionally wherein the surfactant is an anionic surfactant, optionally selected from alkyl sulphates, carboxylates or phospholipids, or a non-ionic surfactant, optionally selected from sorbitan-based surfactants, PEG-fatty acids, or glyceryl fatty acids, or poloxamers, or a combination thereof. Hence the pharmaceutical formulation of all aspects of the invention may comprise at least the following features, a core and a first coating, wherein the core comprises an active ingredient and a surfactant, and the coating comprises or is a water soluble cellulose ether.

In embodiments where the core is in the form of a solid colloid, the surfactant may be in the disperse phase or the continuous phase. The surfactant in the continuous phase may be an anionic surfactant, for example at least one surfactant selected from fatty acid salts and bile salts, particularly an alkyl sulphate, for example sodium dodecyl sulphate. The surfactant in the disperse phase may be a non-ionic surfactant.

In embodiments the core comprises both a non-ionic surfactant and an anionic surfactant. The non-ionic surfactant, for example sodium dodecyl sulphate, may be in the disperse phase and the anionic surfactant, for example polyethoxylated castor oil may be in the disperse phase.

In embodiments the core further comprises a combination of excipients selected from: a non-ionic surfactant and a solvent; an anionic surfactant and a solvent; an anionic surfactant, a non-ionic surfactant and a solvent; a non-ionic surfactant and an oil; an anionic surfactant and an oil; a non-ionic surfactant, an anionic surfactant and an oil; and a non-ionic surfactant, an anionic surfactant, a solvent and an oil. Preferably, the anionic surfactant is an alkyl sulphate, for example sodium dodecyl sulphate, the non-ionic surfactant polyethoxylated castor oil, the oil is a medium chain mono-, di- and/or tri-glyceride, for example caprylic/capric triglyceride, and the solvent is 2-(ethoxyethoxy)ethanol.

The pharmaceutical formulation may further comprise an excipient selected from: a surfactant, a solubiliser, a permeability enhancer, a disintegrant, a crystallisation inhibitor, a pH modifier, a stabiliser, or a combination thereof.

The core of a pharmaceutical formulation of the invention may comprise a disperse phase being or comprising:

a pharmaceutically active ingredient, for example cyclosporin, hydralazine or mesalamine;

a medium chain mono- di- or tri-glyceride, for example caprylic/capric triglyceride;

a non-ionic surfactant, for example a polyethoxylated castor oil; and a solvent, for example 2-(ethoxyethoxy)ethanol and may further comprise a continuous phase being or comprising:

an anionic surfactant, for example at least one surfactant selected from fatty acid salts and bile salts, particularly an alkyl sulphate, for example sodium dodecyl sulphate a hydrogel forming polymer matrix which is or comprises a hydrocolloid selected from carrageenan, gelatin, agar and pectin, or a combination thereof optionally selected from gelatin and agar or a combination thereof, more optionally the polymer of the a hydrogel forming polymer matrix is or comprises gelatin; and optionally a plasticiser, for example a plasticiser selected from glycerin, a polyol for example sorbitol, polyethylene glycol and triethyl citrate or a mixture thereof, particularly sorbitol.

In a variant of the formulation described in the immediately preceding paragraph, the disperse phase is free, or substantially free of active ingredient, the active ingredient being dissolved in the continuous phase.

In one embodiment the formulation comprises a core and a coating outside the core, wherein the core is in the form of a solid colloid, the colloid comprising a continuous phase and a disperse phase, wherein the disperse phase is or comprises:

a hydrophobic active, for example cyclosporin A;

a medium chain mono- di- and/or tri-glyceride, for example caprylic/capric triglyceride;

a polyethoxylated castor oil; and a co-solvent, for example 2-(ethoxyethoxy)ethanol;

and wherein the continuous phase is or comprises:
   a hydrogel-forming polymer matrix which is or comprises a hydrocolloid selected from carrageenan, gelatin, agar and pectin, or a combination thereof optionally selected from gelatin and agar or a combination thereof, more optionally the polymer of the water-soluble polymer matrix is or comprises gelatin;
   optionally a plasticiser, optionally a plasticiser selected from glycerin, a polyol for example sorbitol, polyethylene glycol and triethyl citrate or a mixture thereof, particularly sorbitol; and
      an anionic surfactant, for example at least one surfactant selected from fatty acid salts and bile salts, particularly an alkyl sulphate, for example sodium dodecyl sulphate; and wherein the coating on the core is any of the coatings described herein. Suitably the coating comprises a first coating and a second coating outside the first coating; and wherein
   the first coating is the coating which is or comprises a water-soluble cellulose ether as described above; and
   the second coating is or comprises a coating, suitably a polymeric coating, as defined above to control or modulate release of cyclosporin A from the formulation.

In embodiments comprising a first coating and a second coating, for example as mentioned in the immediately preceding paragraph, a particular first coating is or comprises hydroxypropylmethyl cellulose and a particular second coating outside the first coating is or comprises a pH independent polymer, for example ethyl cellulose; more particularly the second coating is or comprises ethyl cellulose and optionally a polysaccharide selected from water soluble and naturally occurring polysaccharides, for example pectin or another water-soluble naturally occurring polysaccharide. The second coating may therefore contain pectin or another said polysaccharide or it may be substantially free of pectin and other said polysaccharides. There are therefore disclosed second coatings which comprise ethylcellulose as a controlled release polymer and which further comprise pectin or another said polysaccharide as well as second coatings which comprise ethylcellulose as a controlled release polymer and which do not further comprise pectin or another said polysaccharide.

The core may comprise a hydrogel forming polymer comprising gelatin, optionally in an amount of 300 to 700 mg/g, the core further comprising medium chain mono, di and/or tri-glycerides, optionally in an amount of 20 to 200 mg/g, wherein the pharmaceutical formulation further comprises the following components:
   solvent, for example 2-(ethoxyethoxy)ethanol, optionally in an amount of 150 to 250 mg/g;
   non-ionic surfactant, for example a polyethoxylated castor oil, optionally in an amount of 80 to 200 mg/g; and
   anionic surfactant, for example sodium dodecyl sulphate, in an amount of 15 to 50 mg/g.

Where the core is a colloid, the active ingredient may be dissolved in the continuous phase of the colloid.

It is not a requirement of the invention that the core contain a disperse phase: the core may have a single phase which is for example a hydrogel-forming polymer matrix, the matrix having an active ingredient dissolved therein. For example, the active ingredient may be hydralazine.

The invention includes within its scope formulations wherein the core is a colloid having a disperse phase and the continuous phase (matrix phase) of the colloid further includes dispersed particles of a pharmaceutically active ingredient, for example microparticles or nanoparticles. The disperse phase and continuous phase may otherwise be as described elsewhere in this specification, The pharmaceutical formulation of the invention and/or the core may be in the form of a minibead. It may be that the core is a minibead and the first coating and, where applicable, the second coating in conjunction with the core are in the form of a minibead. However, it may be possible for the core to be a minibead and the formulation not to be a minibead. The formulation may additionally comprise a multiplicity of minibeads. Hence the invention contemplates a minibead with the features of the pharmaceutical formulations disclosed herein.

The formulation or the minibead may have a largest cross sectional dimension of a core of from about 0.01 mm to about 5 mm, for example from 1 mm to 5 mm, as in the case of from 1 mm to 3 mm or 1 mm to 2 mm. The minibead may be spheroidal. The spheroidal minibeads may have an aspect ratio of no more than 1.5, for example from 1.1 to 1.5.

In embodiments the pharmaceutical formulation does not comprise an antigen selected from inactivated and attenuated microorganisms.

The pharmaceutical formulation of the invention may be for oral administration. The formulation may be formulated into a unit dosage form for oral administration comprising from 0.1 mg to 1000 mg, optionally from 1 mg to 500 mg, for example 10 mg to 300 mg, or 25 to 250 mg suitably about 25 mg, 35 mg, about 75 mg, about 180 mg, about 210 mg or about 250 mg of pharmaceutically active ingredient. Suitably the formulation is in a multiple minibead unit dosage form selected from soft or hard gel capsules, gelatin capsules, HPMC capsules, compressed tablets or sachets. The minibeads may be as described elsewhere herein.

A further aspect of the invention provides a formulation described herein for use as a medicament. The active ingredient may be an immunosuppressant, for example cyclosporin A; the formulation may comprise at least one further active ingredient, for example at least one further immunosuppressant. In particular there is provided a formulation in which the active ingredient is an immunosuppressant for use in the treatment, e.g. prevention, of a condition of the GIT. The formulation may be for use in the treatment of an inflammatory bowel disease, irritable bowel syndrome, Crohn's disease, ulcerative colitis, celiac disease, graft-versus-host disease, gastrointestinal graft-versus-host disease, gastroenteritis, duodenitis, jejunitis, ileitis, peptic ulcer, Curling's ulcer, appendicitis, colitis, pseudomembranous colitis, diverticulosis, diverticulitis, pouchitis, endometriosis, colorectal carcinoma and adenocarcinoma.

In embodiments where the pharmaceutical formulation does not comprise a second coating, the formulation may be for use in the treatment of conditions that affect the small intestine. Such formulations may be able to treat conditions selected from celiac disease, GVHD or Crohn's disease.

The invention additionally provides a method for administering a pharmaceutically active ingredient to a subject, comprising orally administering to the subject a formulation described herein. The method may be performed in the treatment, e.g. prevention, of disease. The subject may be a mammal, in particular a human. Also provided is a method for treating a condition of the GI tract in a subject, preferably a human, in need thereof comprising orally administering to the mammal a therapeutically effective amount of a formulation described herein and wherein the pharmaceutically active ingredient is one that is potentially effective in the method. For example, the condition may be inflammatory and the active ingredient an immunosuppressant, for example cyclosporin A. Conditions of the GI tract which may be treated or prevented include the conditions disclosed herein.

A further aspect of the invention provides the use of a formulation described herein for use in the manufacture of a medicament for the treatment, e.g. prevention, of a condition of the GIT. Conditions of the GI tract include those disclosed herein.

The invention also contemplates a method of treating a condition selected from inflammatory bowel disease, irritable bowel disease, Crohn's disease, ulcerative colitis, celiac disease, graft vs host disease, gastrointestinal graft-versus-host disease, gastroenteritis, duodenitis, jejunitis, ileitis, peptic ulcer, Curling's ulcer, appendicitis, colitis, pseudomembranous colitis, diverticulosis, diverticulitis, endometriosis, colorectal carcinoma and adenocarcinoma, wherein the method comprises administering a pharmaceutical formulation of the invention.

In another aspect the invention provides a method of treating conditions that affect the small intestine, wherein the method comprises administering a pharmaceutical formulation of the invention which does not comprise a second coating. The conditions of the small intestine may be selected from celiac disease, GVHD or Crohn's disease.

In an aspect of the invention there is provided a process for making a pharmaceutical formulation, the process comprising the step of:

coating a core with a coating comprising HPMC wherein the weight gain due to the coating is from 0.5% to 20% of the weight of the pharmaceutical formulation. The core may comprise a pharmaceutically active ingredient and may be a core as described in this specification.

The process of the immediately preceding paragraph may further comprise producing the core, wherein producing the core comprises the steps of:

mixing a non-aqueous phase with an aqueous phase to form a solid colloid, wherein at least one of the aqueous phase or the non-aqueous phase comprise a pharmaceutically active ingredient, wherein
 (a) the non-aqueous phase comprises a surfactant; and
 (b) the aqueous phase comprises a hydrogel forming polymer; and
then causing or allowing the emulsion to solidify.

Included in the invention is a method of producing more than one batch of a multiplicity of solid unit dosage forms comprising a core, a first coating and a second coating outside the first coating, wherein the core comprises an active ingredient and a hydrogel forming polymer matrix, the first coating comprises or is a water-soluble cellulose ether, and the second coating comprises or is a delayed release polymer, further wherein the first coating is present in an amount to provide each of the more than one batches with a plot of % release of the active ingredient against time with a difference of less than 5 units of % release at any time point in the plot, wherein the method comprises, forming a batch of cores, coating the cores with the first coating in an amount to provide a weight gain due to the coating of from 0.5% and 20% and coating the core with the second coating to provide the one or more batches.

In embodiments the coating is present in an amount to provide a weight gain of from 8% to 12% or any other weight gain mentioned herein.

A method of minimising inter-batch variability in a dissolution profile of a multiplicity of solid unit dosage forms from two or more batches, the method comprising:

forming two or more batches of a multiplicity of solid unit dosage forms; and coating the solid unit dosage forms of each batch with a coating comprising hydroxylpropyl methyl cellulose, wherein the weight gain due to the coating is from 0.5% to 20%.

Where this specification mentions a plurality of batches, e.g. two or more batches, the number of batches may be at least 100, optionally at least 1000.

Another aspect of the invention is a method of avoiding systemic side effects of cyclosporin, the method comprising providing a composition comprising cyclosporin and a coating present in an amount corresponding to a weight gain of 0.5% to 20% of hydroxylpropyl methylcellulose. The method may be used in the treatment of a condition selected from inflammatory bowel disease, irritable bowel disease, Crohn's disease, ulcerative colitis, celiac disease, graft vs host disease, gastrointestinal graft-versus-host disease, gastroenteritis, duodenitis, jejunitis, ileitis, peptic ulcer, Curling's ulcer, appendicitis, colitis, pseudomembranous colitis, diverticulosis, diverticulitis, endometriosis, colorectal carcinoma and adenocarcinoma.

The coating of the invention increases the rate and/or extent of release of the active ingredient from the formulation compared to a corresponding formulation without the coating. The formulations of the invention are therefore expected to provide high concentrations of the active ingredient in-vivo following oral administration, which may improve the oral bioavailability of the active, thereby enhancing the therapeutic benefit of the active ingredient. Enhanced bioavailability may also enable a lower dose of the active to be administered and thereby reduce the size of a unit dosage form or reduce the number of unit dosage form administered to a patient (for example by reducing the number and/or size of capsules required). Accordingly the invention provides the use of formulation of the invention to increase the bioavailability of an active ingredient. The invention further provides a method for increasing the oral bioavailability of an active agent the method comprising administering to a patient a formulation of the invention.

Formulations of the invention which release the active in the stomach and/or upper GI tract (e.g. the small intestine) may be particularly beneficial for improving bioavailability. Accordingly, formulations of the invention which release high amounts of the active in the first 2 to 4 hours of the dissolution test described herein are preferred. Suitably such formulations may be the formulations described herein comprising a first coat (e.g. a water-soluble cellulose ether) and no second coating.

For certain active ingredients it may be desirable to limit or delay release of the active from the formulation until the formulation has passed through the stomach and upper GI tract. The formulations of the invention comprising a second coat may be particularly suitable for such applications. The second coat acts to delay release from the formulation, whilst the presence of the coating of the invention (e.g. HPMC) increases the amount of active released when the formulation releases the active in the lower GI tract. The period of delay to the release of the active as a result of the presence of the second coating can be tailored by appropriate selection of the nature or amount of second coating used. For a given second coating material a higher weight gain of coating will generally increase the time period between administration of the formulation and release of the active. The formulations of the invention can therefore be used to provide high levels of release of active agent at very specific parts of the GI tract to provide, for example, topical treatment to diseased tissue within the GI tract. Such delayed release formulations may be particularly beneficial when the active has undesirable side effects which may arise from systemic absorption higher in the GI tract.

Included in this description by reference are the subject matters of the appended claims. The description is therefore to be read together with the claims and features mentioned in the claims are applicable to the subject matters of the description. For example, a feature described in a process claim is applicable also to products mentioned in the description, where the feature is manifested in the product. For example, a feature mentioned in a product claim is applicable also to relevant process subject matters contained in this description. Similarly, a feature mentioned in the description in the context of a process is applicable also to products mentioned in the description, where the feature is manifested in the product. Also, a feature mentioned in the description in the context of a product is applicable also to relevant process subject matters contained in this description.

BRIEF DESCRIPTION OF THE DRAWINGS

Embodiments of the invention are further described hereinafter with reference to the accompanying drawings, in which.

DETAILED DESCRIPTION

Figure 1:
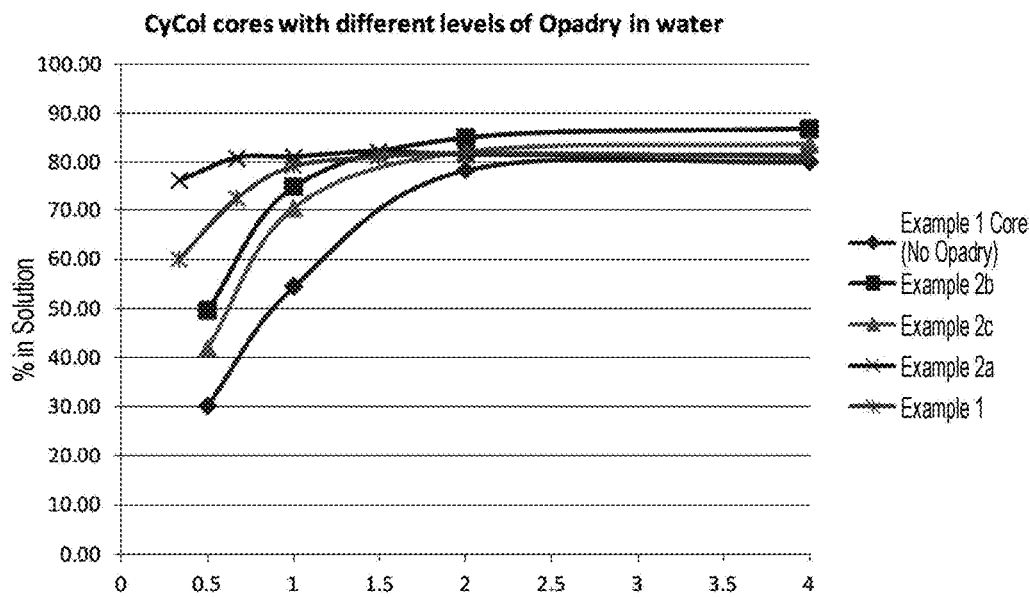
FIG. 1 is a graph plotting % of cyclosporin in solution against time over 4 hours and showing the release profiles of minibeads of Example 1 and Examples 2a-c with differing levels of a coating comprising hydroxypropyl methylcellulose compared to the release profile of a core of Example 1 which does not have a hydroxypropyl methylcellulose coating.

The term "treatment", and the therapies encompassed by this invention, include the following and combinations thereof: (1) reducing the risk of or inhibiting, e.g. delaying, initiation and/or progression of, a state, disorder or condition; (2) preventing, e.g. reducing the risk of, or delaying the appearance of clinical symptoms of a state, disorder or condition developing in a patient (e.g. human or animal) that may be afflicted with or predisposed to the state, disorder or condition but does not yet experience or display clinical or subclinical symptoms of the state, disorder or condition; (3) inhibiting the state, disorder or condition (e.g., arresting, reducing or delaying the development of the disease, or a relapse thereof in case of maintenance treatment, of at least one clinical or subclinical symptom thereof); and/or (4) relieving the condition (e.g. causing regression of the state, disorder or condition or at least one of its clinical or subclinical symptoms). Where the formulation of the invention is used in the treatment of a patient, treatment contemplates any one or more of: maintaining the health of the patient; restoring or improving the health of the patient; and delaying the progression of the disorder. The benefit to a patient to be treated may be either statistically significant or at least perceptible to the patient or to the physician. It will be understood that a medicament will not necessarily produce a clinical effect in every patient to whom it is administered, and this paragraph is to be understood accordingly. The formulations and methods described herein are of use for therapy and/or prophylaxis of disease.

The treatments may include maintenance therapy of patients who have suffered a disorder and whose condition has subsequently improved, e.g. because of treatment. Such patients may or may not suffer a symptomatic disorder. Maintenance therapy aims to arrest, reduce or delay (re-) occurrence or progression of a disorder.

"Effective amount" means an amount sufficient to achieve the desired treatment, e.g. result in the desired therapeutic or prophylactic response. The therapeutic or prophylactic response can be any response that a user (e.g., a clinician) will recognise as an effective response to the therapy. It is further within the skill of one of ordinary skill in the art to determine appropriate treatment duration, appropriate doses, and any potential combination treatments, based upon an evaluation of therapeutic or prophylactic response.

The terms "dry" and "dried" as applied to formulations of the disclosure may each include reference to formulations containing less than 5% free water by weight, e.g. less than 1% free water by weight. Primarily, however, "dry" and "dried" as applied to formulations of the disclosure mean that the hydrogel present in the initial solidified formulation has dried sufficiently to form a rigid formulation. Where a solid colloid is referred to this also refers to a dried colloid according to the definition herein.

Ingredients and excipients of the described formulations are suitable for the intended purpose. For example, pharmaceutical formulations comprise pharmaceutically acceptable ingredients.

If not otherwise stated, ingredients, components, excipients etc. of the formulation of the invention are suitable for one or more of the intended purposes discussed elsewhere herein.

For the avoidance of doubt, it is hereby stated that the information disclosed earlier in this specification under the heading "Background" is relevant to the invention and is to be read as part of the disclosure of the invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Dissolution Profile

Reference to "a two stage dissolution test using a USP Apparatus II with a paddle speed of 75 rpm and a dissolution medium temperature of 37° C.; wherein for the first 2 hours of the dissolution test the dissolution medium is 750 ml of 0.1 N HCl, and for the remainder of the dissolution test 250 ml of 0.2M tribasic sodium phosphate containing 2% SDS is added to the dissolution medium which is then adjusted to pH 6.8" is an in-vitro test carried out in accordance with the USP <711> Dissolution test using Apparatus II (paddle apparatus) operated with a paddle speed of 75 rpm and with the dissolution medium at a temperature of 37° C.±5° C. At the start of the test (t=0) the sample is placed in the dissolution acidic medium. After 2 hours an aliquot of the medium is taken for subsequent analysis and immediately (suitably within 5 minutes) the second stage of the dissolution test is initiated. In the second stage 250 ml of 0.2M tribasic sodium phosphate containing 2% sodium dodecyl sulphate (SDS) is added to the dissolution medium and the pH adjusted to 6.8±0.05 using 2N NaOH or 2N HCl as required. Samples of the dissolution medium are taken at time points during the second stage of the test, for example at 4, 6, 12 and 24 hours from the start of the test (i.e. from t=0 at the start of the first stage). The samples are analysed for the active dissolved in the medium. The "% released" is the amount of active (e.g. cyclosporin) in solution in the respective dissolution medium at a particular time point relative to the amount of active in the composition at the start of the test. The concentration of active in a sample may be measured using standard techniques, such as Reverse Phase HPLC as illustrated in the Examples. References to "a two stage dissolution test" refer to this test method.

Formulation

The formulation comprises a matrix and a pharmaceutically active ingredient. The matrix may be formed with a hydrogel-forming polymer, and may contain additional excipient(s) to the polymer. The active ingredient is contained within the matrix. The active ingredient may be in solution or in suspension, or in a combination thereof; however the invention is not limited to formulations comprising a solution or suspension of the active and it includes, for example, active ingredients encapsulated in liposomes or cyclodextrin. The matrix may contain inclusions in which the active ingredient is comprised; for example, the inclusions may comprise a hydrophobic medium in which the active ingredient is dissolved or suspended. An active ingredient may therefore be directly dissolved or suspended in the matrix, or it may be dissolved or suspended indirectly in the matrix by way of inclusions in which the active ingredient is dissolved or suspended.

The formulation, therefore, comprises a matrix-forming polymer, in particular a hydrogel-forming polymer. The matrix of the formulation may be or comprise a polymer matrix comprising a polymer selected from a water-permeable polymer, a water-swellable polymer and a biodegradable polymer. In particular, the matrix is or comprises a hydrogel-forming polymer described in more detail below.

Modified release of the active ingredient from the formulation may be achieved by virtue of the properties of the matrix material. For example the matrix may be a permeable or erodible polymer within which the active ingredient is contained, e.g. dissolved or suspended; following oral administration the matrix is gradually dissolved or eroded thereby releasing the active ingredient from the matrix. Erosion may be achieved by biodegradation of a biodegradable polymer matrix. Where the matrix is permeable, water permeates the matrix enabling the drug to diffuse from the matrix. A matrix formed with a hydrogel-forming polymer may therefore include a modified release polymer. As such modified release polymers may be mentioned cellulose derivatives, for example hydroxypropylmethyl cellulose, poly(lactic acid), poly(glycolic)acid, poly(lactic-co glycolic acid copolymers), polyethylene glycol block co-polymers, polyorthoesters, polyanhydrides, polyanhydride esters, polyanhydride imides, polyamides and polyphosphazines.

Water Soluble Cellulose Ether Coating

The invention provides pharmaceutical formulations that have a coating which is or comprises a water-soluble cellulose ether. The invention provides pharmaceutical formulations that have a polymer coating, wherein the polymer is or comprises a water-soluble cellulose ether. The water-soluble cellulose ether may be, for example selected from methyl cellulose, hydroxyethyl cellulose, hydroxylpropyl cellulose and hydroxypropylmethyl cellulose.

Suitably the material of the first coating (i.e. the sub-coating) is different to the second coating on the composition. For example, where the first coating is or comprises a water-soluble ester of a cellulose ether, the major component(s) (e.g. more than 50%) of the second coating is or comprises a different polymer to that of the first coating. Accordingly, the first and second coatings suitably provide two layers of material as part of the composition. It is to be understood that when the second coating comprises a mixture of components, minor components of the outer second coating may the same as the material of the first coating. By way of example, when the first coating is or comprises HPMC and the second coating comprises ethyl cellulose, the ethyl cellulose may optionally further comprise a minor amount (e.g. less than 50%, 40%, 30% or 20%) of the first coating material, HPMC in this example. In such embodiments the sub-coat and the second coating are considered to be different.

The water-soluble cellulose ether may be a water-soluble cellulose ether selected from an alkyl cellulose, for example methyl cellulose, ethyl methyl cellulose; a hydroxyalkyl cellulose, for example hydroxyethyl cellulose (available as Cellosize™ and Natrosol™), hydroxypropyl cellulose (available as Klucel™) or hydroxymethyl cellulose; a hydroxyalkyl alkyl cellulose, for example hydroxyethyl methyl cellulose (HEMC), hydroxypropyl methyl cellulose (available as Methocel™, Pharmacoat™, Benecel™) or ethyl hydroxyethyl cellulose (EHEC); and a carboxyalkyl cellulose, for example carboxymethyl cellulose (CMC). Suitably the water-soluble cellulose ether may, for example be selected from methyl cellulose, hydroxyethyl cellulose, hydroxylpropyl cellulose and hydroxypropylmethyl cellulose.

The water-soluble cellulose ether may be a low viscosity polymer which is suitable for application as a film or coating to the formulation. The viscosity of the polymer may be from about 2 to about 60 mPa·s, for example a viscosity of: about 2 to about 20 mPa·s; about to 2 to about 8 mPa·s; more suitably a viscosity of about 4 to about 10 mPa·s, for example about 4 to about 6 mPa·s. Alternatively, the viscosity of the polymer may fall outside any or all of the just-mentioned ranges, for example be above 20 mPa·s. Alternatively, the viscosity of the polymer may fall outside any or all of the just-mentioned ranges, for example be above 20 mPa·s. The viscosity of the polymer may be determined by measuring the viscosity of a 2% solution of the polymer in water at 20° C. using a Ubbelode viscometer using ASTM standard methods (D1347 and D2363).

The water soluble cellulose ether may be a water-soluble hydroxypropylmethyl cellulose (HPMC or hypromellose). HPMC is prepared by modifying cellulose to substitute hydroxy groups with methoxy and hydroxypropyl groups. Each anhydroglucose unit in the cellulose chain has three hydroxyl groups. The amount of substituent groups on the anhydroglucose units may be expressed as the degree of substitution. If all three hydroxyl groups on each unit are substituted, the degree of substitution is 3. The number of substituent groups on the ring determines the properties of the HPMC. The degree of substitution may also be expressed as the weight % of the methoxy and hydroxypropyl groups present. Suitably the HPMC has from about 19 to about 30% methoxy substitution and from about 7 to about 12% hydroxypropyl substitution. Particularly the HPMC has 25 to 30% methoxy substitution and 7 to 12% hydroxypropyl substitution. Suitably the HPMC is a low viscosity HPMC which is suitable for application as a film or coating to the formulation. The viscosity of the HPMC is suitably from about 2 to 60 mPa·s, for example about 2 to about 20 mPa·s, more suitably a viscosity of about 4 to about 10 mPa·s. The viscosity of the HPMC is determined by measuring the viscosity of a 2% solution of the HPMC in water at 20° C. using a Ubbelode viscometer using ASTM standard methods (D1347 and D2363). Such HPMC is available as for example Methocel™, for example Methocel™ E, including Methocel™ E5.

When the first coating is or comprises a water-soluble derivative of a cellulose ether, the derivative may, for example be a water-soluble ester of a cellulose ether. Water-soluble esters of cellulose ethers are well known and may comprise esters of a cellulose ether, formed with one or more suitable acylating agent(s). Acylation agents may be, for example suitable acids or acid anhydrides or acyl halides. Accordingly the ester of a cellulose ether may contain a single ester moiety or two or more ester moieties to give a mixed ester. Examples of water-soluble esters of cellulose ethers may be water-soluble phthalate, acetate, succinate, propionate or butyrate esters of a cellulose ether (for example HPMC). Suitably the water-soluble ester of a cellulose ether is a water-soluble phthalate, acetate-succinate, propionate, acetate-propionate or acetate-butyrate ester of a cellulose ether (for example HPMC).

In one embodiment the water-soluble ester of a cellulose ether may be or comprise a water-soluble ester of any of the water-soluble cellulose ethers described above in relation to the sub-coating.

Particular water-soluble esters of cellulose ethers are water-soluble esters of HPMC. Esters of HPMC which are soluble in water at a pH greater than 5.5 may be or comprise hydroxypropyl methylcellulose phthalate (HPMCP), or hydroxypropyl methylcellulose acetate succinate (HPMCAS) in which the presence of ionisable carboxyl groups causes the polymer to solubilize at high pH (>5.5 for the LF grade and >6.8 for the HF grade). These polymers are commercially available from Shin-Etsu Chemical Co. Ltd.

The cellulose ether-containing coating may comprise or be hypromellose, e.g. it may be made of a mixture of hypromellose, titanium dioxide and polyethylene glycol; the coating may comprise at least 20 wt % hypromellose and optionally at least 50% or at least 75 wt % hypromellose, e.g. at least 80 wt % or at least 85 wt % or 90 wt % hypromellose. The coating material used to form the coating may therefore comprise a dry weight percentage of hypromellose mentioned in the preceding sentence.

If it is desired for the coating to use a mixture of hypromellose, titanium dioxide and polyethylene glycol, commercial products corresponding to such mixtures are available including Opadry® White, a product commercialised by Colorcon. More generally, there may be mentioned various products commercialised under the trade name Opadry® and Opadry® II. Further non limiting examples include Opadry® YS-1-7706-G white, Opadry® Yellow 03B92357, Opadry® Blue 03B90842). These formulations are available as dry film coating formulations that can be diluted in water shortly before use. Opadry® and Opadry® II formulations comprise a cellulosic film forming polymer (e.g., HPMC and/or HPC), and may contain polydextrose, maltodextrin, a plasticizer (e.g., triacetin, polyethylene glycol), polysorbate 80, a colorant (e.g., titanium dioxide, one or more dyes or lakes), and/or other suitable film-forming polymers (e.g., acrylate-methacrylate copolymers). Suitable Opadry® or Opadry® II formulations may comprise a plasticizer and one or more of maltodextrin, and polydextrose (including but not limited to a) triacetin and polydextrose or maltodextrin or lactose, or b) polyethylene glycol and polydextrose or maltodextrin). Particularly preferred commercial products are Opadry® White (HPMC/HPC-based) and Opadry® II White (PVA/PEG-based).

The cellulose ether-containing coating may also be applied as a simple solution comprising water and the polymer of the first coating. For example when the polymer is an HPMC, for example such as Methocel, the first coating may be applied to the core as an aqueous solution or dispersion of the HPMC. Optionally the coating solution may include other solvents such as an alcohol. Alternatively the coating may be applied as a solution or dispersion in a volatile organic solvent.

Suitably the coating that contains a water soluble cellulose ether is present in an amount corresponding to a weight gain of the formulation due to the coating of from 0.5% to 40% (for example from 0.5% to 30%; from 0.5% to 20%; from 1% to 25%; from 1% to 15%; from 1% to 6%; from 1% to 4%; from 4% to 6%; from 6% to 10%; from 9% to 15%; or from 12% to 15%) by weight based upon the weight of the formulation prior to applying the coating.

In another embodiment the first coating that contains a water-soluble cellulose ether is present in an amount corresponding to a weight gain due to the first coating in a range selected from 9 to 30%, suitably 9% to 20%, or particularly 10% to 15% by weight based upon the weight of the formulation prior to applying the coating.

Suitably the coating that contains a water soluble cellulose ether provides a coating thickness on the formulation of from about 10 μm to about 1 mm, for example, from about 10 μm to about 500 μm, from about 50 μm to about 1 mm, or about from about 50 μm to about 500 μm. The thickness may therefore be from about 100 μm to about 1 mm, e.g. 100 μm to about 750 μm or about 100 μm to about 500 μm. The thickness may be from about 250 μm to about 1 mm, e g about 250 μm to about 750 μm or 250 μm to about 500 μm. The thickness may be from about 500 μm to about 1 mm, e g about 750 μm to about 1 mm or about 500 μm to about 750 μm. The thickness may therefore be from about 10 μm to about 100 μm, e.g. from about 10 μm to about 50 μm or about 50 μm to about 100 μm.

When the first coating comprises a water-soluble cellulose ether the cellulose ether(s) suitably forms at least 40%, 50%, 60%, 70%, 80%, 85% or 90% by weight of the dry weight of the first coating. Alternatively the water-soluble cellulose ether is the first coating.

It is preferred to dry the formulation of the invention before the first coating that contains a water-soluble cellulose ether is applied, as is described in more detail below in relation to the coating process.

It has been found that applying to a core comprising a pharmaceutically active ingredient a sub-coating, referred to elsewhere in the application as the subcoat (hence the subcoat and the first coating are equivalent), that contains a water soluble cellulose ether prior to applying a delayed release coating provides unexpected advantages. The presence of such a sub-coating has been found to enhance the dissolution properties of the delayed release formulations according to the invention. In particular the presence of such a sub-coating has been found to increase the rate of release of the active ingredient from the formulation and also to increase the amount of the active ingredient released in a set time period compared to formulations prepared without using such a sub-coating. These findings are unexpected, because it would have been expected that the presence of a sub-coating in addition to a delayed release outer coating would act to delay or inhibit release of drug from the formulation and, at a given time, for there to be less drug released, because there is a thicker coating present. However, as illustrated in the Examples, contrary to these expectations both the extent and rate of release of active ingredient are increased compared to formulations without such a sub-coating. Accordingly, delayed release formulation formulations according to the invention which comprise a sub-coat that comprises or is a water-soluble cellulose ether and a delayed release coating outside the sub-coat, provide a unique dissolution profile. The presence of such a sub-coating has also been found to reduce batch-to-batch variability, particularly when the core is in the form of a minibead. A sub-coating that comprises or is a water-soluble cellulose ether may therefore also reduce intra- and inter-patient variability as a result of a more consistent dissolution profile. The unique properties of sub-coated formulations according to the invention (particularly the dissolution profile) are expected to contribute to favourable pharmacokinetic properties of the formulations according to the invention.

Accordingly in an embodiment there is provided a formulation comprising a pharmaceutically active ingredient, wherein the formulation further comprises a first coating; and wherein the first coating is or comprises a water-soluble cellulose ether.

The formulation may have a second coating comprising or being a delayed release polymer.

Accordingly in an embodiment there is provided a formulation comprising a pharmaceutically active ingredient, wherein the formulation further comprises a first coating and a second coating outside the first coating; and wherein the first coating is or comprises a water-soluble cellulose ether; and the second coating is or comprises a delayed release coating, e.g. is or comprises a delayed release polymer.

An aspect of the invention resides in a multiple minibead composition comprising at least two populations of active ingredient-containing minibeads, wherein members of at least one minibead population are minibeads as described herein (i.e. formulations of the invention in minibead format). It will be understood that the two populations are different. Such a plural minibead population composition may comprise or consist of the following two populations:

a first population having a coating that is or comprises a water-soluble cellulose ether but having no outer coating, e.g. as described herein; and a second population having a first coating that is or comprises a water-soluble cellulose ether and a second coating that is or comprises a delayed release coating, for example as described herein e.g. a coating that is or comprises a delayed release polymer.

The respective minibeads of each population of a plural minibead composition may contain the same active ingredient(s) as the minibeads of some or all of the other populations, or they may contain different active ingredient(s) thereto, e.g. a different combination. Thus, all the minibeads of a multiple minibead population may contain the same active ingredient(s), for example they may all contain an active ingredient selected from immunosuppressants (e.g. cyclosporin), hydroxylase inhibitors (e.g. hydralazine) and anti-inflammatories (e.g. mesalazine). More generally, all the minibeads of a multiple minibead population may contain any identical active ingredient, for example selected from those described herein.

A multiple population composition may be for use in treating a disorder of the GI tract, for example as described herein. Such a formulation may be for use in treating a disorder affecting multiple regions of the GIT, e.g. the upper intestine and the lower intestine, and may comprise an active ingredient selected from immunosuppressants (e.g. cyclosporin), hydroxylase inhibitors (e.g. hydralazine) and anti-inflammatories (e.g. mesalazine).

The minibeads of a multiple population composition may by way of example be contained in a gel capsule or a sachet.

An example of an active ingredient of a formulation of the disclosure is cyclosporin A. Suitably in the embodiment of the preceding paragraph the first coating (sub-coating) is applied to a core comprising cyclosporin A. In a particular embodiment the core is or comprises a pharmaceutically active ingredient, for example cyclosporin A, in a polymeric matrix, particularly a water-soluble polymer matrix. Still more particularly the core comprises a hydrogel-forming polymer matrix and cyclosporin A. Such cores are described in more detail below. Cyclosporin A may be replaced in this example by hydralazine or mesalazine.

The second coating is outside the first coating and may be any of the delayed release coatings described herein. In particular, the second coating is or comprises a pH independent polymer modified release coating described above. For example the second coating may be or comprise an enteric coating or a pH independent coating. The second coating may comprise a mixture of polymers including a polymer degradable by bacterial or other enzymes. In a particular embodiment the second coating comprises ethyl cellulose and optionally a water-soluble polysaccharide, in particular one susceptible to degradation by colonic bacteria, suitably pectin. Accordingly the second coating may comprise the Surelease-pectin mixture described above.

Accordingly in one embodiment of the invention there is provided a formulation comprising a core, a first coating and a second coating outside the first coating; and wherein:

the core comprises a polymer matrix, in particular a hydrogel-forming polymer matrix, and a pharmaceutically active ingredient;

the first coating is or comprises a water-soluble cellulose ether, particularly hydroxypropylmethyl cellulose;

the second coating is or comprises a modified release coating or delayed release coating, particularly a pH independent modified release coating;

the first coating is present in an amount corresponding to a weight gain due to the first coating in a range selected from: (i) from 8% to 12%, for example about 10%; or (ii) from 4% to 6%, for example about 5% by weight based upon the weight of the formulation prior to applying the first coating; and wherein the second coating is present in an amount corresponding to a weight gain of the formulation due to the second coating selected from (a) from 10% to 12%, for example about 11% or about 11.5%; (b) from 16% to 18%, for example about 17% by weight based upon the weight of the formulation prior to applying the second coating.

The first and second coatings in the embodiment of the immediately preceding paragraph are suitably any of the first and second coatings described above or below. Accordingly it is intended that the coatings described in this section may be applied to any of the formulations described herein to provide a delayed release coating if required. The coatings are particularly useful to provide a modified release coating to the cores comprising a polymer matrix and pharmaceutically active ingredient described in this application.

The presence of a sub-coating as described in this specification, amongst other things, increases the amount of active ingredient released from the formulation during dissolution compared to formulations without such a sub-coating. Accordingly there is provided a delayed release formulation comprising a pharmaceutically active ingredient, wherein the formulation comprises a first coating (sub coating) and second coating as described herein; wherein the first coating is present in an amount to provide a % release of the active ingredient that is higher than a % release of the active ingredient from a corresponding formulation without the first coating throughout a time period from 8 hours to 18 hours, when measured in the dissolution test described herein. For example the sub-coated formulation provides a higher % release in the period between 10 hours and 16 hours, suitably between 10 hours and 14 hours and more particularly at about 10 hours, about 12, hours about 14 hours or about 16 hours in the dissolution test. A sub-coated formulation of the invention may, for example, provide 2% or higher, 5% or higher or 10% or higher more active ingredient release at a given time point during the dissolution test compared to the same formulation without the subcoating, for example 2 to 15% more active ingredient; the teaching of this paragraph applies in particular to cyclosporin A.

Polymer Matrix Core

The formulation of the invention comprises a core wherein the core comprises a pharmaceutically active ingredient and a continuous phase or matrix phase to provide mechanical strength. In embodiments the active ingredient phase is or comprises a disperse phase within the continuous phase or matrix. The continuous phase or matrix phase suitably comprises a water-soluble polymer matrix and in particular comprises a hydrogel-forming polymer matrix. The core may comprise a polymer matrix wherein the matrix-forming polymer is a hydrogel-forming polymer or a combination thereof.

The active ingredient may be present as a disperse phase within the hydrogel-forming polymer matrix (continuous phase or aqueous phase) of the core. The disperse phase may be hydrophobic, in which instance the active ingredient may be hydrophobic, but may alternatively be hydrophilic. For example the disperse phase may comprise a lipid and cyclosporin A or another hydrophobic active. The cores may be prepared by dispersing the active ingredient phase within the aqueous phase to form a colloid and then causing the formulation to solidify (gel), thereby immobilising the active ingredient within the hydrogel-forming polymer matrix.

The core may have the form of a solid colloid, the colloid comprising a continuous phase and a disperse phase, wherein the continuous phase is or comprises the hydrogel-forming polymer and the disperse phase is or comprises a pharmaceutically active ingredient, for example a plurality of pharmaceutically active ingredients. The disperse phase may comprise a vehicle containing the active ingredient, for example containing it as a solution or a suspension. The vehicle may be hydrophobic, and may comprise or be a solution of a hydrophobic active ingredient or a suspension of a hydrophilic active ingredient. The disperse phase may by way of example be liquid, semi-solid or solid.

The core may have the characteristics of a dried colloid in which the active ingredient is dispersed within the hydrogel-forming polymer matrix. Thus, the core may have the form of a dried colloid, the colloid comprising a continuous phase and a disperse phase, wherein the continuous phase is or comprises the hydrogel-forming polymer and the disperse phase is or comprises a pharmaceutically active ingredient, for example a plurality of pharmaceutically active ingredients. The disperse phase may comprise a vehicle containing the active ingredient, for example containing it as a solution or a suspension. The vehicle may be hydrophobic, and may comprise or be a solution of a hydrophobic active ingredient or a suspension of a hydrophilic active ingredient. The disperse phase may by way of example be liquid, semi-solid or solid. The dried colloid may be a dried emulsion, i.e. the core may have the characteristics of a dried colloid.

Such cores comprising a water-soluble polymer, particularly a hydrogel-forming polymer and a disperse phase comprising cyclosporin A are described in more detail below.

Delayed Release Coatings

The invention provides formulations having a coating that comprises, or is, a coating-forming polymer, wherein the coating-forming polymer is a hydrogel-forming polymer; the coating may be a first coating outside which is a second coating. The second coating may be a delayed release coating, although the invention does not require that the second coating be a delayed release coating. The second coating may comprise or be a delayed release polymer.

Thus according to one embodiment of the present invention, there is provided a pharmaceutical formulation comprising a core, a first coating and a second coating outside the first coating, wherein the core comprises a pharmaceutically active ingredient and the first coating comprises or is a water-soluble cellulose ether.

The first coating may be present in an amount described elsewhere in this specification.

The second coating may be present in an amount described elsewhere herein. Suitably the second coating provides a coating thickness on the formulation of from about 10 μm to about 1 mm, for example, from about 10 μm to about 500 μm, from about 50 μm to about 1 mm, or about from about 50 μm to about 500 μm. The thickness may therefore be from about 100 μm to about 1 mm, e.g. 100 μm to about 750 μm or about 100 μm to about 500 μm. The thickness may be from about 250 μm to about 1 mm, e g about 250 μm to about 750 μm or 250 μm to about 500 μm. The thickness may be from about 500 μm to about 1 mm, e g about 750 μm to about 1 mm or about 500 μm to about 750 μm. The thickness may therefore be from about 10 μm to about 100 μm, e.g. from about 10 μm to about 50 μm or about 50 μm to about 100 μm.

The core is preferably in the form of a minibead, for example as described hereafter in more detail, for example in the form of a solid colloid. The second coat may be a film or it may be a membrane. The second coat, e.g. film or membrane, may serve to delay release until after the stomach; the coat may therefore be an enteric coat. The delayed release coat may comprise one or more delayed release substances, preferably of a polymeric nature (e.g. methacrylates etc.; polysaccharides etc. as described in more detail below), or combination of more than one such substance, optionally including other excipients, for example, plasticizers. Preferred plasticizers, if they are used, include hydrophilic plasticizers for example triethyl citrate (TEC) which is particularly preferred when using the Eudragit® family of polymers as coatings as described below. Another preferred plasticiser, described in more detail below in relation to coating with ethyl cellulose, is dibutyl sebacate (DBS). Alternative or additional optionally included excipients are glidants. A glidant is a substance that is added to a powder or other medium to improve its flowability. A typical glidant is talc which is preferred when using the Eudragit® family of polymers as coatings.

The delayed release coating may be applied as described below and may vary as to thickness and density. The amount of coat is defined by the additional weight added to (gained by) the dry formulation (e.g. bead) to which it is applied. Weight gain is preferably in the range 0.1% to 50%, preferably from 1% to 15% of the dry weight of the bead, more preferably in the range 3% to 10% or in the range 5-12% or in the range 8-12%.

Polymeric coating material of a delayed release coating may comprise methacrylic acid co-polymers, ammonio methacrylate co-polymers, or mixtures thereof. Methacrylic acid co-polymers such as, for example, EUDRAGIT™ S and EUDRAGIT™ L (Evonik) are particularly suitable. These polymers are gastroresistant and enterosoluble polymers. Their polymer films are insoluble in pure water and diluted acids. They may dissolve at higher pHs, depending on their content of carboxylic acid. EUDRAGIT™ S and EUDRAGIT™ L can be used as single components in the polymer coating or in combination in any ratio. By using a combination of the polymers, the polymeric material can exhibit solubility at a variety of pH levels, e.g. between the pHs at which EUDRAGIT™ L and EUDRAGIT™ S are separately soluble. In particular, the coating may be an enteric coating comprising one or more co-polymers described in this paragraph. A particular coating material to be mentioned is Eudragit L 30 D-55.

The trade mark "EUDRAGIT" is used hereinafter to refer to methacrylic acid copolymers, in particular those sold under the trade mark EUDRAGIT by Evonik.

The delayed release coating, where present, can comprise a polymeric material comprising a major proportion (e.g., greater than 50% of the total polymeric coating content) of at least one pharmaceutically acceptable water-soluble polymer, and optionally a minor proportion (e.g., less than 50% of the total polymeric content) of at least one pharmaceutically acceptable water insoluble polymer. Alternatively, the membrane coating can comprise a polymeric material comprising a major proportion (e.g., greater than 50% of the total polymeric content) of at least one pharmaceutically acceptable water insoluble polymer, and optionally a minor proportion (e.g., less than 50% of the total polymeric content) of at least one pharmaceutically acceptable water-soluble polymer.

Ammonio methacrylate co-polymers such as, for example, EUDRAGIT™ RS and EUDRAGIT™ RL (Evonik) are suitable for use in the present invention. These polymers are insoluble in pure water, dilute acids, buffer solutions, and/or digestive fluids over the entire physiological pH range. The polymers swell in water and digestive fluids independently of pH. In the swollen state, they are then permeable to water and dissolved active agents. The permeability of the polymers depends on the ratio of ethylacrylate (EA), methyl methacrylate (MMA), and trimethylammonioethyl methacrylate chloride (TAMCl) groups in the polymer. For example, those polymers having EA:MMA:TAMCl ratios of 1:2:0.2 (EUDRAGIT™ RL) are more permeable than those with ratios of 1:2:0.1 (EUDRAGIT™ RS). Polymers of EUDRAGIT™ RL are insoluble polymers of high permeability. Polymers of EUDRAGIT™ RS are insoluble films of low permeability. A diffusion-controlled pH-independent polymer in this family is RS 30 D which is a copolymer of ethyl acrylate, methyl methacrylate and a low content of methacrylic acid ester with quaternary ammonium groups present as salts to make the polymer permeable. RS 30 D is available as an aqueous dispersion.

The amino methacrylate co-polymers can be combined in any desired ratio, and the ratio can be modified to modify the rate of drug release. For example, a ratio of EUDRAGIT™ RS:EUDRAGIT™ RL of 90:10 can be used. Alternatively, the ratio of EUDRAGIT™ RS:EUDRAGIT™ RL can be about 100:0 to about 80:20, or about 100:0 to about 90:10, or any ratio in between. In such formulations, the less permeable polymer EUDRAGIT™ RS generally comprises the majority of the polymeric material with the more soluble RL, when it dissolves, permitting gaps to be formed through which solutes can come into contact with the core allowing for the active to escape in a controlled manner.

The amino methacrylate co-polymers can be combined with the methacrylic acid co-polymers within the polymeric material in order to achieve the desired delay in the release of the drug and/or poration of the coating and/or exposure of the formulation within the coating to allow egress of drug and/or dissolution of the immobilization or water-soluble polymer matrix. Ratios of ammonio methacrylate co-polymer (e.g., EUDRAGIT™ RS) to methacrylic acid co-polymer in the range of about 99:1 to about 20:80 can be used. The two types of polymers can also be combined into the same polymeric material, or provided as separate coats that are applied to the beads.

Eudragit™ FS 30 D is an anionic aqueous-based acrylic polymeric dispersion consisting of methacrylic acid, methyl acrylate, and methyl methacrylate and is pH sensitive. This polymer contains fewer carboxyl groups and thus dissolves at a higher pH (>6.5). The advantage of such a system is that it can be easily manufactured on a large scale in a reasonable processing time using conventional powder layering and fluidized bed coating techniques. A further example is EUDRAGIT® L 30D-55 which is an aqueous dispersion of anionic polymers with methacrylic acid as a functional group. It is available as a 30% aqueous dispersion.

In addition to the EUDRAGIT™ polymers described above, a number of other such copolymers can be used to control drug release. These include methacrylate ester co-polymers such as, for example, the EUDRAGIT™ NE and EUDRAGIT™ NM ranges. Further information on the EUDRAGIT™ polymers can be found in "Chemistry and Application Properties of Polymethacrylate Coating Systems," in Aqueous Polymeric Coatings for Pharmaceutical Dosage Forms, ed. James McGinity, Marcel Dekker Inc., New York, pg. 109-114 the entirety of which is incorporated herein by reference.

Several derivatives of hydroxypropyl methylcellulose (HPMC) also exhibit pH dependent solubility and may be used in the invention for the delayed release coating. As examples of such derivatives may be mentioned HPMC esters, for example hydroxypropyl methylcellulose phthalate (HPMCP), which rapidly dissolves in the upper intestinal tract and hydroxypropyl methylcellulose acetate succinate (HPMCAS) in which the presence of ionisable carboxyl groups causes the polymer to solubilize at high pH (>5.5 for the LF grade and >6.8 for the HF grade). These polymers are commercially available from Shin-Etsu Chemical Co. Ltd. As with other polymers described herein as useful for delayed release coatings, HPMC and derivatives (e.g. esters) may be combined with other polymers e.g. EUDRAGIT RL-30 D.

Other polymers may be used to provide a coating in particular enteric, or pH-dependent, polymers. Such polymers can include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropylmethylcellulose phthalate, hydroxypropylmethylcellulose acetate succinate, starch acetate phthalate, amylose acetate phthalate, polyvinyl acetate phthalate, and polyvinyl butyrate phthalate.

pH Independent Polymer Delayed Release Coatings

In a particular embodiment the second coating, where present, is or comprises a polymeric coating which is pH-independent in its dissolution profile and/or in its ability to release the active ingredient incorporated in the formulations of the invention. A pH-independent polymer delayed release coating comprises a delayed release polymer, optionally a plurality of delayed release polymers, and one or more other optional components. The other components may serve to modulate the properties of the formulation. Examples have already been given (e.g., Eudragit RS and RL).

Another example of a pH-independent polymeric coating is a coating that comprises or is ethylcellulose; a pH-independent polymeric coating may have a delayed release polymer that is ethylcellulose, therefore. It will be understood that an ethylcellulose formulation for use in coating a dosage form may comprise, in addition to ethylcellulose and—in the case of a liquid formulation—a liquid vehicle, one or more other components. The other components may serve to modulate the properties of the formulation, e.g. stability or the physical properties of the coating such as the flexibility of the film coating. The ethylcellulose may be the sole delayed release polymer in such a formulation. The ethylcellulose may be in an amount of at least 50%, at least 60%, at least 70%, at least 80%, at least 90% or at least 95% by weight of the dry weight of a coating formulation for use in coating a dosage form. Accordingly, an ethylcellulose coating may include other components in addition to the ethylcellulose. The ethylcellulose may be in an amount of at least 50%, at least 60%, at least 70%, at least 80%, at least 90% or at least 95% by weight of the ethylcellulose coating. Consequently, ethylcellulose may be in an amount of at least 50%, at least 60%, at least 70%, at least 80%, at least 90% or at least 95% by weight of the dry weight of the second coating. Suitably the ethyl cellulose coating further comprises a plasticizer as described below to improve the flexibility of the film and to improve the film-forming properties of the coating formulation during application of the coating.

A particular ethylcellulose coating formulation which may be applied to the first coating is a dispersion of ethylcellulose in a sub-micron to micron particle size range, e.g. from about 0.1 to 10 µm in size, homogeneously suspended in water with the aid of an emulsification agent, e g ammonium oleate. The ethylcellulose dispersion may optionally and preferably contain a plasticizer. Suitably plasticisers include for example dibutyl sebacate (DBS), diethylphthalate, triethyl citrate, tributyl citrate, triacetin, or medium chain triglycerides. The amount of plasticizer present in the coating formulation will vary depending upon the desired properties coating. Typically the plasticizer comprises from 1 to 50%, for example about 8 to about 50% of the combined weight of the plasticizer and ethyl cellulose. Such ethylcellulose dispersions may, for example, be manufactured according to U.S. Pat. No. 4,502,888, which is incorporated herein by reference. One such ethylcellulose dispersion suitable for use in the present invention and available commercially is marketed under the trademark Surelease®, by Colorcon of West Point, Pa. USA. In this marketed product, the ethylcellulose particles are, e.g., blended with oleic acid and a plasticizer, then optionally extruded and melted. The molten plasticized ethylcellulose is then directly emulsified, for example in ammoniated water optionally in a high shear mixing device, e.g. under pressure. Ammonium oleate can be formed in situ, for instance to stabilize and form the dispersion of plasticized ethylcellulose particles. Additional purified water can then be added to achieve the final solids content. See also U.S. Pat. No. 4,123,403, which is incorporated herein by reference.

The trademark "Surelease®" is used hereinafter to refer to ethylcellulose coating materials, for example a dispersion of ethylcellulose in a sub-micron to micron particle size range, e.g. from about 0.1 to 10 µm in size, homogeneously suspended in water with the aid of an emulsification agent, e.g. ammonium oleate. In particular, the trademark "Surelease®" is used herein to refer to the product marketed by Colorcon under the Surelease® trademark.

Surelease® dispersion is an example of a combination of film-forming polymer, plasticizer and stabilizers which may be used as a second coating to adjust rates of active principle release with reproducible profiles that are relatively insensitive to pH. The principal means of drug release is by diffusion through the Surelease® dispersion membrane and is directly controlled by film thickness. Use of Surelease® is particularly preferred and it is possible to increase or decrease the quantity of Surelease® applied as coating in order to modify the dissolution of the coated formulation. Unless otherwise stipulated, use of the term "Surelease" may apply to Surelease® E-7-19020, E-7-19030, E-7-19040 or E-7-19050. An ethylcellulose coating formulation, for example Surelease® E-7-19020, may comprise ethylcellulose blended with oleic acid and dibutyl sebacate, then extruded and melted. The molten plasticized ethylcellulose is then directly emulsified in ammoniated water in a high shear mixing device under pressure. Ammonium oleate is formed in situ to stabilize and form the dispersion of plasticized ethylcellulose particles. Additional purified water is then added to achieve the final solids content. An ethylcellulose coating formulation, for example Surelease® E-7-19030, may additionally comprise colloidal anhydrous silica dispersed into the material. An ethylcellulose coating formulation, for example Surelease® E-7-19040, may comprise medium chain triglycerides instead of dibutyl sebacate, in particular in a formulation comprising colloidal anhydrous silica and oleic acid. An ethylcellulose coating formulation, for example Surelease® E-7-19050, may derive from blending ethylcellulose with oleic acid before melting and extrusion. The molten plasticized ethylcellulose is then directly emulsified in ammoniated water in a high shear mixing device under pressure. Ammonium oleate is formed in situ to stabilize and form the dispersion of plasticized ethylcellulose particles. However, formulations that comprise medium chain triglycerides, colloidal anhydrous silica and oleic acid are preferred. Surelease® E-7-19040 is particularly preferred.

The invention also contemplates using combinations of ethylcellulose, e.g. a Surelease® formulation, with other coating components, for example sodium alginate, e.g. sodium alginate available under the trade name Nutrateric™.

In addition to the EUDRAGIT™ and Surelease® polymers discussed above, where compatible, any combination of coating polymers disclosed herein may be blended to provide additional delayed-release profiles.

The delayed release coating can further comprise at least one soluble excipient to increase the permeability of the polymeric material. These soluble excipients can also be referred to or are pore formers. Suitably, the at least one soluble excipient or pore former is selected from among a soluble polymer, a surfactant, an alkali metal salt, an organic acid, a sugar, a polysaccharide, and a sugar alcohol. Such soluble excipients include, but are not limited to, polyvinyl pyrrolidone, polyvinyl alcohol (PVA), polyethylene glycol, a water-soluble hydroxypropyl methyl cellulose, sodium chloride, surfactants such as, for example, sodium lauryl sulfate and polysorbates, organic acids such as, for example, acetic acid, adipic acid, citric acid, fumaric acid, glutaric acid, malic acid, succinic acid, and tartaric acid, sugars such as, for example, dextrose, fructose, glucose, lactose, and sucrose, sugar alcohols such as, for example, lactitol, maltitol, mannitol, sorbitol, and xylitol, xanthan gum, dextrins, and maltodextrins; and a polysaccharide susceptible of degradation by a bacterial enzyme normally found in the colon, for example polysaccharides include chondroitin sulphate, pectin, dextran, guar gum and amylase, chitosan etc. and derivatives of any of the foregoing. In some embodiments, polyvinyl pyrrolidone, mannitol, and/or polyethylene glycol can be used as soluble excipients. The at least one soluble excipient can be used in an amount ranging from about 0.1% to about 15% by weight, based on the total dry weight of the polymer coating, for example from about 0.5% to about 10%, about 0.5% to about 5%, about 1% to about 3%, suitably about 2% based on the total dry weight of the polymer coating. The delayed release coating may be free from HPMC.

The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release formulations are known in the art and are described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566 all of which are incorporated herein by reference in their entirety.

The addition to Surelease® or other pH-independent polymer substance of a second polymer (e.g. a polysaccharide, especially a heteropolysaccharide) which is susceptible to degradation by colonic bacterial enzymes (and optionally or alternatively by pancreatic or other relevant enzymes), helps provide targeted release of the active ingredient to a site or sites within the GI tract where the second polymer is degraded. By varying the amount of second polymer added present in the coating the dissolution profile may be optimized to provide the required release of cyclosporin A from the formulation.

In a particular embodiments the delayed release coating provides for release of the active agent in at least the colon. Accordingly in one embodiment the coating comprises a combination of ethylcellulose (preferably a described above, and particularly formulated with an emulsification agent such as, for example, ammonium oleate and/or a plasticizer such as, for example, dibutyl sebacate or medium chain triglycerides) and a polysaccharide susceptible of degradation by a bacterial enzyme normally found in the colon. Such polysaccharides include chondroitin sulphate, pectin, dextran, guar gum and amylase, chitosan etc. and derivatives of any of the foregoing. Chitosan may be used in connection with obtaining a colon-specific release profile; additionally or alternatively, pectin may be so used.

The use of polysaccharides by themselves for delayed release coating purposes has been tried with limited success. Most of the non-starch polysaccharides suffer from the drawback of lacking good film forming properties. Also, they tend to swell in the GI tract and become porous, resulting in the early release of the drug. Even amorphous amylose, which is resistant to degradation by pancreatic alpha amylase but capable of degradation by colonic bacterial enzymes, has the disadvantage of swelling in aqueous media although this can be controlled by incorporating insoluble polymer, for example ethyl cellulose and/or acrylate, into the amylose film. Amylose however is not water-soluble and although water-insoluble polysaccharides are not excluded, use of a water-soluble polysaccharide (WSP) susceptible of bacterial enzymic degradation brings particularly advantageous results when used as a coating in accordance with this embodiment of the present invention. A particularly preferred polysaccharide in this embodiment of the present invention is pectin. Various kinds of pectin may be used including pectin of different grades available i.e. with differing degrees of methylation (DM), i.e. percentage of carbonyl groups esterified with methanol, for example pectins with a DM of more than 50%, known as High Methoxy (HM) Pectins or Low Methoxy (LM) pectins, or a pectin combination comprising an HM pectin and an LM pectin. It is also possible in this embodiment to use pectins having various degrees of acetylation (DAc). Taken together, the DM and DAc or the degree of substitution is known as Degree of Esterification (DE). pectins of various DE's may be used according to the invention. As an alternative to pectin, sodium alginate may be used as a polysaccharide according to an embodiment of the invention. However, other embodiments may conveniently include amylose and/or starch which contains amylose. Various grades of starch, containing different percentages of amylose may be used including for example Hylon V (National Starch Food Innovation) which has an amylose percentage of 56% or Hylon VII which has an amylose percentage of 70%. The remaining percentage is amylopectin. The polysaccharides pectin, amylose and sodium alginate are particularly preferred for achieving colon delivery of the active ingredient.

It has been found that water-soluble polysaccharide, suitably pectin, can act as a former of pores in the coating otherwise provided by ethylcellulose (preferably Surelease®). By "pores" is not meant shaft-like holes from the surface to the core of the formulation, rather areas of weakness or absence of coating occurring stochastically on and within the coating of the invention.

Pore formers have been described before in connection with Surelease® (see e.g. US 2005/0220878).

According to a particular embodiment of the invention the delayed release coating comprises ethylcellulose, e.g. Surelease®, and a water-soluble polysaccharide (WSP) wherein the proportion of ethylcellulose (in particular Surelease®) to WSP is ideally in the range 90:10 to 99:1, preferably, 95:5 to 99:1, more preferably 97:3 to 99:1, for example about 98:2 based upon the dry weight of the coating. Suitably in this embodiment the weight gain of the formulation due to application of the coating comprising ethylcellulose, e.g. Surelease®, and the WSP is in the range of from 1 to 30% (for example from: 3% to 25%; 5% to 15%; 8% to 14%; 10% to 12%; 12% to 18%; or 16% to 18%, suitably the weight gain is about 11%, about 11.5%, or about 17%). It is particularly preferred that the WSP in this embodiment is pectin. Particularly favoured weight gains using coatings comprising ethylcellulose, e.g. Surelease®, are those in the range 5-12% or in the range 8-12%.

Accordingly in an embodiment the second coating comprises ethyl cellulose and a water soluble polysaccharide (particularly pectin) wherein the water-soluble polysaccharide (WSP) is present in an amount of 0.1% to about 10% by weight, based on the dry weight of the second coating. Suitably the WSP is present in an amount of from about 0.5% to about 10%, for example about 0.5% to about 5%, about 1% to about 3%, suitably about 2% based on the total dry weight of the second coating. In this embodiment the WSP is preferably pectin. In this embodiment the second formulation suitably further comprises a plasticizer. Suitable plasticizers include these described above in relation to Surelease®. Suitably the weight gain of the formulation due to application of the second coating in this embodiment is in the range of from 1 to 30% (for example from: 3% to 25%; 5% to 15%; 8% to 14%; 10% to 12%; 12% to 18%; or 16% to 18%, suitably the weight gain is about 11%, about 11.5%, or about 17%).

In an embodiment the delayed release polymer is not a water-soluble cellulose ether. Where the second coating comprises or is a delayed release polymer the delayed release polymer may not be the same as the water-soluble cellulose ether of the first coating. Accordingly the second coating may not be the same as the first coating.

Continuous Phase Polymer Matrix (Aqueous Phase)

This section of the specification relating to the polymer matrix recites amounts of constituents in terms of percent by weight of the formulation. In the context of this section of the specification, what is meant is percent by weight of the dry weight of the core, i.e. excluding coating(s).

It will be recalled that the core may comprise a matrix or continuous phase and optionally, but not necessarily, also a disperse phase or discontinuous phase. Suitably the continuous phase of the core is or comprises a hydrogel-forming polymer. A hydrogel-forming polymer is a polymer capable of forming a hydrogel. A hydrogel may be described as a solid or semi-solid material, which exhibits no flow when at rest, comprising a network (matrix) of hydrophilic polymer chains that span the volume of an aqueous liquid medium.

The core may comprise a hydrogel-forming polymer selected from the group consisting of: gelatin; agar; agarose; pectin; carrageenan; chitosan; alginate; starch; xanthan gum; gum Arabic; guar gum; locust bean gum; polyurethane; polyether polyurethane; cellulose; cellulose ester, cellulose acetate, cellulose triacetate; cross-bonded polyvinyl alcohol; polymers and copolymers of acrylic acid, hydroxyalkyl acrylates, hydroxyethyl acrylate, diethylene glycol monoacrylate, 2-hydroxypropylacrylate, 3-hydroxypropyl acrylate; polymers and copolymers of methacrylic acid, hydroxyethyl methacrylate, diethyleneglycol monomethacrylate, 2-hydroxypropyl methacrylate, 3-hydroxypropyl methacrylate, dipropylene glycol monomethylacrylate; vinylpyrrolidone; acrylamide polymers and copolymers, N-methylacrylamide, N-propylacrylamide; methacrylamide polymers and copolymers, N-isopropylmethacrylamide, N-2-hydroxyethylmethacrylamide; and vinyl pyrrolidone; and combinations thereof. In specific embodiments binary or tertiary etc combinations of any of the above substances are foreseen.

In a further embodiment the hydrogel-forming polymer is selected from the group consisting of gelatin, agar, a polyethylene glycol, starch, casein, chitosan, soya bean protein, safflower protein, alginates, gellan gum, carrageenan, xanthan gum, phthalated gelatin, succinated gelatin, cellulosephthalate-acetate, oleoresin, polyvinylacetate, polymerisates of acrylic or methacrylic esters and polyvinylacetatephthalate and any derivative of any of the foregoing; or a mixture of one or more such a hydrogel-forming polymers The hydrogel-forming polymer may also be referred to as a hydrocolloid i.e. a colloid system wherein the colloid particles are disperse in water and the quantity of water available allows for the formation of a gel. In embodiments it is preferred to use reversible hydrocolloids preferably thermo-reversible hydrocolloids (e.g. agar, agarose, gelatin etc) as opposed to irreversible (single-state) hydrocolloids. Thermo-reversible hydrocolloids can exist in a gel and sol state, and alternate between states with the addition or elimination of heat. Gelatin, agar and agarose are thermoreversible, rehydratable colloids and are particularly preferred. Gelatin derivatives such as, for example, succinated or phthalated gelatins are also contemplated. Thermoreversible hydrocolloids which may be used according to the invention, whether individually or in combination, include those derived from natural sources such as, for example, carrageenan (extracted from seaweed), gelatin (extracted from bovine, porcine, fish or vegetal sources), agar (from seaweed), agarose (a polysaccharide obtained from agar) and pectin (extracted from citrus peel, apple and other fruits). A non-animal based hydrocolloid may be preferred for certain applications e.g. administration to vegetarians or to individuals not wishing to ingest animal products for religious or health reasons. In relation to the use of carrageenan, reference is made to US patent application 2006/0029660 A1 (Fonkwe et al), the entirety of which is incorporated herein by reference. The hydrogel-forming polymer may comprise or be a combination of gelatin with one or more other thermoreversible hydrocolloids, e.g. with one or more other of the thermoreversible hydrocolloids just listed. The hydrogel-forming polymer may comprise or be a combination of gelatin with agar; optionally, at least one further thermoreversible hydrocolloid may be included in the combination, for example one just listed.

Thermo-reversible colloids present a benefit over other hydrogel-forming polymers. Gelation or hardening of thermo-reversible colloids occurs by cooling the colloid, e.g. in a liquid cooling bath or by air flow. Gelation of other hydrogel-forming polymers, which is chemically driven, can lead to leakage of the formulation contents into the gelation medium as the hardening process can take time to occur. Leakage of the content of the formulation may lead to an inaccurate quantity of the active ingredient within the formulation. Thermo-reversible colloids are also known as thermo-reversible gels, and it is therefore preferred that the hydrogel former be a thermo-reversible gelling agent.

Another term which may be applied to hydrogel formers which are advantageous is "thermotropic": a thermotropic gelling agent (which the reader will infer is preferred as a hydrogel former used in the invention) is one caused to gel by a change in temperature and such gelling agents are able to gel more rapidly than those whose gelling is chemically induced, e.g. ionotropic gelling agents whose gelling is induced by ions, for example chitosan. In embodiments of the invention, therefore, the hydrogel former is a thermotropic gel-forming polymer or a combination of such polymers.

The manufacture of the formulation to prepare a core may require that the hydrogel-forming polymer be present as a solution, which is preferably an aqueous solution. The hydrogel-forming polymer represents between 5% and 50%, preferably between 10% and 30%, still more preferably between 15% and 20% by weight of the aqueous phase during manufacture as described herein. In addition the hydrogel-forming polymer may comprise 8 to 35%, (for example 15-25%, preferably 17-18%) hydro-gel forming polymer; 65%-85% (preferably 77-82%) of water plus, optionally, from 1-5% (preferably 1.5 to 3%) sorbitol. When present surfactant (e.g. anionic surfactant) in the aqueous phase pre-mix may be present in an amount of 0.1 to 5% (preferably 0.5 to 4%) wherein all parts are by weight of the aqueous phase.

In embodiments the formulation comprises at least 25%, suitably at least 40% by weight based upon the dry weight of the formulation of the hydrogel-forming polymer. For example the hydrogel-forming polymer is present form 25 to 70%, for example 40 to 70% suitably 45 to 60% of the formulation, wherein the % is by weight based upon the dry weight of the formulation.

In embodiments the hydrogel-forming polymer is a pharmaceutically acceptable polymer.

In certain embodiments the hydrogel-forming polymer is gelatin. In certain embodiments the hydrogel-forming polymer comprises gelatin. In certain embodiments the gelatin comprises at least 40%, for example 40 to 70% suitably 45 to 60% of the formulation, wherein the % is by weight based upon the dry weight of the formulation.

The hydrogel-forming polymer may optionally comprise a plasticiser for example sorbitol or glycerine, or a combination thereof. In particular one or more plasticisers may be combined with gelatin.

In embodiments in which the hydrogel-forming polymer comprises or is gelatin, reference is hereby made to "Bloom strength", a measure of the strength of a gel or gelatin developed in 1925 by O. T. Bloom. The test determines the weight (in grams) needed by a probe (normally with a diameter of 0.5 inch) to deflect the surface of the gel 4 mm without breaking it. The result is expressed in Bloom (grades) and usually ranges between 30 and 300 Bloom. To perform the Bloom test on gelatin, a 6.67% gelatin solution is kept for 17-18 hours at 10° C. prior to being tested.

When the hydrogel-forming polymer comprises or is gelatin the bloom strength of the gelatin may be in the range of 125 Bloom to 300 Bloom, 200 Bloom to 300 Bloom and preferably 250 Bloom to 300 Bloom. It should be appreciated that higher bloom strength gelatin can be replaced by lower bloom strength gelatin at higher concentrations.

According to the invention, in embodiments in which the hydrogel-forming polymer matrix comprises or is gelatin, the gelatin may be sourced by a variety of means. For example, it can be obtained by the partial hydrolysis of collagenous material, such as the skin, white connective tissues, or bones of animals. Type A gelatin is derived mainly from porcine skins by acid processing, and exhibits an isoelectric point between pH 7 and pH 9, while Type B gelatin is derived from alkaline processing of bones and animal (bovine) skins and exhibits an isoelectric point between pH 4.7 and pH 5.2. Type A gelatin is somewhat preferred. Gelatin for use in the invention may also be derived from the skin of cold water fish. Blends of Type A and Type B gelatins can be used in the invention to obtain a gelatin with the requisite viscosity and bloom strength characteristics for bead manufacture.

Lower temperature gelatin (or gelatin derivatives or mixtures of gelatins with melting point reducers) or other polymer matrices able to be solidified at lower temperatures (e.g. sodium alginate) may also be used. It is therefore believed that polymer which comprises or is low temperature gelatin is a preferred matrix polymer.

According to the invention, in embodiments in which the polymer comprises or is gelatin, the starting gelatin material is preferably modified before manufacture to produce "soft gelatin" by the addition of a plasticizer or softener to the gelatin to adjust the hardness of the formulation of the invention. The addition of plasticizer achieves enhanced softness and flexibility as may be desirable to optimise dissolution and/or further processing such as, for example, coating. Useful plasticizers of the present invention for combination with gelatin or another hydrogel-forming polymer include glycerine (1,2,3-propanetriol), D-sorbitol (D-glucitol), sorbitol BP (a non-crystallizing sorbitol solution) or an aqueous solution of D-sorbitol, sorbitans (e.g. Andidriborb 85/70), mannitol, maltitol, gum arabic, triethyl citrate, tri-n-butyl citrate, dibutylsebacate. Other or similar low molecular weight polyols are also contemplated for example ethylene glycol and propylene glycol. Polyethylene glycol and polypropylene glycol may also be used although these are less preferred. Glycerine and D-sorbitol may be obtained from the Sigma Chemical Company, St. Louis, Mo. USA or Roquette, France. Some active agents and excipients included for other functions may act as plasticisers.

Softeners or plasticisers, if utilized, can be ideally incorporated in a proportion rising to 30%, preferably up to 20% and more preferably up to 10% by dry weight of the formulation of the invention, even more preferably between 3 and 8%, and most preferably between 4% and 6%.

Although not essential, the hydrogel-forming polymer matrix may also optionally contain a disintegrant where it is particularly desired to enhance the rate of disintegration of the formulation of the invention. Examples of disintegrants which may be included are alginic acid, croscarmellose sodium, crospovidone, low-substituted hydroxypropyl cellulose and sodium starch glycolate.

A crystallisation inhibitor (e.g. approximately 1% by dry weight of the formulation) may also be included in the formulation of the invention. An example is hydroxy propyl/methyl cellulose (HPC or HPMC, hypromellose etc) which may play other roles such as, for example, emulsifier.

In another embodiment, the hydrogel-forming polymer matrix is chitosan which can exist in the form of biogels with or without additives as described e.g. in U.S. Pat. No. 4,659,700 (Johnson & Johnson); by Kumar Majeti N.V. Ravi in Reactive and Functional Polymers, 46, 1, 2000; and by Paul et al. in ST.P. Pharma Science, 10, 5, 2000 the entirety of all 3 of which is incorporated herein by reference. Chitosan derivatives e.g. thiolated entities are also contemplated.

The hydrogel-forming polymer matrix may be a non-hydrocolloid gum. Examples are the cross-linked salts of alginic acid. For example, aqueous solutions of sodium alginate gums extracted from the walls of brown algae have the well known property of gelling when exposed to di- and trivalent cations. A typical divalent cation is calcium, often in the form of aqueous calcium chloride solution. It is preferred in this embodiment that the cross-linking or gelling have arisen through reaction with such a multivalent cation, particularly calcium.

The hydrogel-forming polymer matrix may have a low water content, therefore the formulation may have a low water content. As described below, during manufacture of a core the disperse phase, optionally comprising an active ingredient, is mixed with an aqueous solution of the hydrogel-forming polymer and the formulation is gelled, for example to provide cores which are minibeads. Suitably the cores are dried following formation to reduce the water content present in the core.

In certain embodiments the formulation does not comprise compounds containing a disulphide bond. In embodiments the hydrogel-forming polymer does not comprise compounds containing a disulphide bond.

The hydrogel-forming polymer matrix forming the continuous phase of the core (aqueous phase) may further comprise a surfactant. Surfactants which may be used in the formulation are described in the section "surfactants" below.

Surfactant which may be present in the continuous aqueous phase of the core include, for example a surfactant selected from the group consisting of: cationic; amphoteric (zwitterionic); anionic surfactants, for example perfluorooctanoate (PFOA or PFO), perfluoro-octanesulfonate (PFOS), sodium dodecyl sulfate (SDS), ammonium lauryl sulfate, and other alkyl sulfate salts, sodium laureth sulfate, also known as sodium lauryl ether sulfate (SLES) and alkyl benzene sulphonate; and non-ionic surfactants for example perfluorocarbons, polyoxyethyleneglycol dodecyl ether (e.g. Brij such as, for example, Brij 35), Myrj (e.g. Myrj 49, 52 or 59), Tween 20 or 80 (also known as Polysorbate) (Brij, Myrj and Tween products are available commercially from Croda), poloxamers which are nonionic triblock copolymers composed of a central hydrophobic chain of polyoxypropylene (poly(propylene oxide)) flanked by two hydrophilic chains of polyoxyethylene (poly(ethylene oxide)), or a combination of the foregoing. In particular, the surfactant may be selected from, or comprise, anionic surfactants and combinations thereof, the anionic surfactants optionally being those mentioned in this paragraph. A particular class of surfactant comprises sulfate salts. A preferred anionic surfactant in the aqueous phase is SDS. Mixtures of anionic surfactants may be used. Mixtures of further surfactants are also contemplated, e.g. mixtures comprising perfluorocarbons.

In embodiments of the invention, the core comprises a hydrophilic surfactant which, without being bound by theory, is believed at least partially to partition the aqueous phase (polymer matrix).

Such surfactants intended for such inclusion in the aqueous phase of the core are preferably readily diffusing or diffusible surfactants to facilitate manufacturing and processing of the formulation of the invention.

The surfactant may have an HLB of at least 10 and optionally of at least 15, e.g. at least 20, or at least 30 and optionally of 38-42, e.g. 40. Such surfactants can be of any particular type (ionic, non-ionic, zwitterionic) and may comprise as a proportion of dry weight of the formulation from 0.1% to 6%, e.g. 0.1% to 5%. 0.1% to 4% or 0.1% to 3%, more preferably in a proportion of at least 1% and in particular between 1.0 and 4.5 or 5%, ideally within or just outside the 2-4% range, for example from 2 to 3% or approximately 2% or approximately 4%.

Unless otherwise stated or required, all percentages and ratios are by weight.

In one embodiment the anionic surfactant may be an anionic surfactant selected from alkyl sulphates, carboxylates or phospholipids, or combinations thereof.

The physical form of the surfactant at the point of introduction into the aqueous phase during preparation of the core plays a role in the ease of manufacture of the core. As such, although liquid surfactants can be employed, it is preferred to utilize a surfactant which is in solid form (e.g. crystalline, granules or powder) at room temperature, particularly when the aqueous phase comprises gelatin.

In general, mixtures of surfactants can be utilised e.g. to achieve optimum long term stability of the formulation of the invention with shorter chain surfactants in general facilitating shorter term stability (an aid to processing) and longer chain surfactants facilitating longer term stability (an aid to shelf life). In some embodiments, shorter chain surfactants have up to $C_{10}$ alkyl (e.g. $C_6$-$C_{10}$ alkyl) as the hydrophobic portion of the surfactant whilst longer chain surfactants have $C_{10}$ or higher alkyl (e.g. $C_{10}$-$C_{22}$ alkyl) as the hydrophobic portion of the surfactant. It is envisaged that $C_{10}$ alkyl surfactants may facilitate processing or facilitate prolongation of shelf life, or both, depending on the identity of the other excipients and of the active principle(s). Higher alkyl may in particular implementations of the invention be $C_{11}$-$C_{22}$ or $C_{12}$-$C_{22}$ alkyl, and in some embodiments has a length of no greater than $C_{18}$.

The matrix phase may comprise pharmaceutically active agent in solution in the matrix phase. Such active agents in solution in the matrix phase are therefore not present as a separate phase but are part of the continuous matrix phase. Active agents suitable to be in solution in the matrix phase are those which are soluble in the aqueous premix which, during manufacture, is used to form the matrix phase. Additionally or alternatively, a pharmaceutically active agent may be comprised in a disperse phase.

Disperse Phase

The polymer matrix of the core described above (for example a hydrogel-forming polymer) may comprise a disperse phase. Suitably the disperse phase, where present, may comprise a pharmaceutically active agent, in particular a hydrophobic active agent. The invention also includes formulations in which the disperse phase comprises a hydrophilic pharmaceutically active agent. In embodiments, therefore, the disperse phase comprises cyclosporin A or another hydrophobic active. In such embodiments the hydrophobic active is preferably soluble in the disperse phase, i.e. the disperse phase comprises a vehicle in which the active is dissolved. Embodiments wherein the hydrophobic active is soluble in the disperse phase are preferred, because such formulations release the cyclosporin in a solubilised form, which may enhance the therapeutic effect of the drug at the site of release, for example by enhancing absorption into the colonic mucosa.

In embodiments a pharmaceutically active agent is or is comprised in the disperse phase.

The disperse phase may comprise a water immiscible phase (also referred to herein as an oil phase). The water immiscible phase may be solid, semi-solid or liquid at ambient temperature (e.g. 25° C.), and therefore the oil phase may for example be waxy at ambient temperature. The oil phase may be or may comprise a liquid lipid and optionally a solvent miscible therewith. A pharmaceutically active ingredient may be present in the oil phase. Suitably the active ingredient is soluble in the oil phase.

The disperse phase may comprise a combination of oils. The liquid lipid may be a short-, medium- or long-chain triglyceride formulation, or a combination thereof. A medium chain triglyceride(s) (MCT) comprises one or more triglycerides of at least one fatty acid selected from $C_6$, $C_7$, $C_8$, $C_9$, $C_{10}$, $C_{11}$ and $C_{12}$ fatty acids. It will be understood that commercially available triglyceride, in particular MCT, formulations useful in the invention are mixtures derived from natural products and usually or always contain minor amounts of compounds which are not MCTs; the term "medium chain triglyceride formulation" is therefore to be interpreted to include such formulations. A short chain triglyceride(s) comprises one or more triglycerides of at least one short chain fatty acid selected from $C_2$-$C_5$ fatty acids. A long chain triglyceride(s) comprises one or more triglycerides of at least one long chain fatty acid having at least 13 carbon atoms.

The liquid lipid may comprise or be triglycerides and/or diglycerides. Such glycerides may be selected from medium chain glycerides or short chain triglycerides or a combination thereof.

The liquid lipid may be a caprylic/capric triglyceride, i.e. a caprylic/capric triglyceride formulation (which it will be understood may contain minor amounts of compounds which are not caprylic/capric triglycerides).

Said solvent which is optionally included in an oil phase may be miscible with both the liquid lipid and with water. Examples of suitable solvents are 2-(2-ethoxyethoxy)ethanol available commercially under trade names Carbitol™, Carbitol cellosolve, Transcutol™, Dioxitol™, Poly-solv DE™, and Dowanal DE™; or the purer Transcutol™ HP (99.9). Transcutol P or HP, which are available commercially from Gattefosse, are preferred. Another possible co-solvent is poly(ethylene glycol). PEGs of molecular weight 190-210 (e.g. PEG 200) or 380-420 (e.g. PEG 400) are preferred in this embodiment. Suitable PEGs can be obtained commercially under the name "Carbowax" manufactured by Union Carbide Corporation although many alternative manufacturers or suppliers are possible.

The disperse phase may represent from 10-85% by dry weight of the core.

As discussed above the disperse phase may be an oil phase comprising any pharmaceutically suitable oil, e.g. a liquid lipid. The oil phase may be present as oil drops. In terms of dry weight of the core, the oil phase may comprise a proportion from 10% to 85%, e.g. 15% to 50%, for example 20% to 30% or from 35% to 45%. The term "oil" means any substance that is wholly or partially liquid at ambient temperature or close-to-ambient temperature e.g. between 10° C. and 40° C. or between 15° C. and 35° C., and which is hydrophobic but soluble in at least one organic solvent. Oils include vegetable oils (e.g. neem oil) and petrochemical oils.

Oils which may be included in the oil phase include poly-unsaturated fatty acids such as, for example, omega-3 oils for example eicosapentanoic acid (EPA), docosohexaenoic acid (DHA), alpha-linoleic acid (ALA), conjugated linoleic acid (CLA). Preferably ultrapure EPA, DHA or ALA or CLA are used e.g. purity up to or above 98%. Omega oils may be sourced e.g. from any appropriate plant e.g. sacha inchi. Such oils may be used singly e.g. EPA or DHA or ALA or CLA or in any combination. Combinations of such components including binary, tertiary etc combinations in any ratio are also contemplated e.g. a binary mixture of EPA and DHA in a ratio of 1:5 available commercially under the trade name Epax 6000. The oil part of the oil phase may comprise or be an oil mentioned in this paragraph.

Oils which may be included in the oil phase are particularly natural triglyceride-based oils which include olive oil, sesame oil, coconut oil, palm kernel oil, neem oil. The oil may be or may comprise saturated coconut and palm kernel oil-derived caprylic and capric fatty acids and glycerin e.g. as supplied under the trade name Miglyol® a range of which are available and from which one or more components of the oil phase of the invention may be selected including Miglyol® 810, 812 (caprylic/capric triglyceride); Miglyol® 818: (caprylic/capric/linoleic triglyceride); Miglyol® 829: (caprylic/capric/succinic triglyceride; Miglyol® 840: (propylene glycol dicaprylate/dicaprate). Note that Miglyol® 810/812 are MCT formulations which differ only in $C_8/C_{10}$-ratio and because of its low $C_{10}$-content, the viscosity and cloud point of Miglyol® 810 are lower. The Miglyol® range is available commercially from Sasol Industries. As noted above, oils which may be included in the oil phase need not necessarily be liquid or fully liquid at room temperature. Waxy-type oils are also possible: these are liquid at manufacturing temperatures but solid or semi-solid at normal ambient temperatures. The oil part of the oil phase may comprise or be an oil mentioned in this paragraph.

Alternative or additional oils which may be included in the oil phase according to the invention are other medium chain triglyceride formulations such as for example Labrafac™ Lipophile manufactured by Gattefosse in particular product number WL1349. Miglyol® 810, 812 are also medium chain triglyceride formulations.

Accordingly the oil phase may be or comprise medium chain mono-di- or tri-glycerides.

The medium chain glyceride(s) (eg mono- di- or triglyceride(s)) mentioned herein are those which comprise one or more triglycerides of at least one fatty acid selected from fatty acids having 6, 7, 8, 9, 10, 11 or 12 carbon atoms, e.g. $C_8$-$C_{10}$ fatty acids.

Other possible (alternative or additional) oils include linoleoyl macrogolglycerides (polyoxylglycerides) such as, for example, Labrafil (e.g. product number M2125CS by Gattefosse) and caprylocaproyl macrogolglycerides such as, for example, Labrasol by Gattefosse.

The oil phase may further comprise one or more surfactants as described below under the section "surfactants". For example the oil phase may comprise one or more non-ionic or amphoteric surfactants. Particularly the oil phase may comprise one or more non-ionic surfactants listed under "surfactants" below. The presence of a surfactant in the oil phase may also provide enhanced solubilisation of an active ingredient contained in it (i.e. act as a solubiliser) and/or may provide enhanced emulsification when the disperse phase is mixed with the aqueous polymer phase during preparation of the core (i.e act as an emulsifier).

Surfactant in the oil phase may for example be or comprise polyethoxylated castor oils (polyethylene glycol ethers) which can be prepared by reacting ethylene oxide with castor oil. Commercial preparations may also be used as a surfactant/solubilizer e.g. those commercial preparations which contain minor components such as, for example, polyethyelene glycol esters of ricinoleic acid, polyethyelene glycols and polyethyelene glycol ethers of glycerol. A preferred example is Kolliphor® EL, previously known as Cremophor EL. Another surfactant which may be present in the oil phase is for example a phospholipid.

In embodiments the surfactant in the oil phase may be or comprise a non-ionic surfactant selected from sorbitan-based surfactants, PEG-fatty acids, glyceryl fatty acids, or poloxamers.

Within embodiments, the HLB of the oil may be in the range 0-10 (optionally 1-8, e.g. 1-6 and sometimes 1-5).

In another embodiment the oil phase comprises an oil with an HLB in the range 0-10 (preferably 1-5) and a surfactant (suitably a non-ionic surfactant) with an HLB in the range 10-20 and optionally 11-20 (preferably 11-15) range 0-10 (preferably 1-5).

In another embodiment the oil phase comprises an oil and a surfactant (suitably a non-ionic surfactant) wherein the oil and the surfactant both have an HLB in the range 0-10. For example the oil has an HLB of 1-5, for example 1 to 4 or 1-2 and the surfactant has an HLB 2-8, for example 3-7, 2-6, or 3-4).

Suitable oils with a low HLB (HLB less than 10) include medium chain triglycerides, linoleoyl macrogolglycerides (polyoxylglycerides), caprylocaproyl macrogolglycerides and caprylic/capric triglyceride. In terms of commercial products, particularly preferred oils in the lower HLB range are Labrafac™ Lipophile (e.g. 1349 WL), Labrafil, Labrasol, Captex 355 and Miglyol® 810.

One example of a surfactant with high HLB which may be used in a low HLB oil includes polyethoxylated castor oils (polyethylene glycol ethers), for example the commercial product Kolliphor® EL.

In an embodiment the oil phase comprises of a surfactant of high HLB and an oil of low HLB in a ratio of 1-4:1 by weight, e.g. 1.2-3.0:1 by weight, preferably 1.5-2.5:1 by weight and most preferably 1.8-2.2:1 by weight (high HLB: low HLB) advantageously stabilizes the emulsion before and after immobilization of the oil droplets in the aqueous phase. In this context "stabilize" means in particular that the embodiment improves dissolution and/or dispersion of the formulation in vitro. In this embodiment "high" HLB is generally intended above 10, preferably from 10-14, more preferably between 12 and 13. By "low" HLB is generally intended below 10, preferably in the range 1 to 4, more preferably 1 to 2.

It is to be understood that the oil phase in the embodiments above may further comprise or more solvents, for example 2-(2-ethoxyethoxy)ethanol or low molecular weight PEG as mentioned above.

A particular oil phase comprises an oil (low HLB), a high HLB non-ionic surfactant and a co-solvent. For example the following three commercial products: Transcutol P (as co-solvent), Myglyol 810 (as oil) and Kolliphor® EL (surfactant). Miglyol® has a low HLB and Kolliphor® EL has a high HLB. An oil phase may therefore comprise or consist of a combination of the following and optionally a pharmaceutically active ingredient: 2-ethoxyethanol, an MCT and particularly a caprylic/capric triglyceride formulation, and a polyethoxylated castor oil.

A hydrophobic active ingredient is preferably soluble in the oil phase. As discussed below in relation to preparation of the core, the hydrophobic active ingredient is suitably dissolved in the oil phase and the oil phase in mixed with an aqueous phase comprising the hydrogel-forming polymer.

The disperse phase (oil phase) may be or comprise a glyceride formulation, optionally wherein the disperse phase is or comprises a fatty acid monoglyceride, diglyceride or triglyceride or a combination thereof, or the disperse phase is or comprises a caprylic/capric triglyceride formulation.

The disperse phase of the colloidal core may comprise self-assembly structures, for example micelles, vesicles, liposomes or nanoparticles, or at least the structures which result from drying aqueous colloids of such types (have the characteristics of structures which result from drying aqueous colloids of such types). The invention in particular includes formulations in which the disperse phase is micellar, i.e. formed of micelles and/or promicelles. The term "promicelle" refers to a part of a formulation which will form a micelle upon contact with water, e.g. gastrointestinal contents.

The following discussion for convenience refers to micelles but is applicable in general to other self-assembly structures. A micelle-forming surfactant is present as micelles dispersed within the hydrogel-forming polymer in a "wet" (not yet dried) composition made as an intermediate in the manufacturing process described herein. It is believed also to be present as micelles in the dried composition but observability of micelles or micelle-like structures in the dried composition is not a requirement of the invention. It is mentioned at this point that the presence of a surfactant in micelle form does not require that the entire surfactant content of a composition is in micelle form as it is considered more probable that a portion of the surfactant will be outside the micelles. Thus in the "wet" composition, whether the hydrogel-forming polymer is in the gel state or the sol (liquid) state may comprise the micelle-forming surfactant at a concentration above the critical micelle concentration.

The diameter of the dispersed micelles may be between 0.5 nm and 200 nm, 1 nm and 50 nm, or 5 nm and 25 nm. The size of the micelles may be determined by dynamic light scattering or diffusion NMR techniques known within the art. Although the size of the micelles is given as a diameter this does not imply that the micelles must be purely spherical species only that they may possess some approximately circular dimension.

The surfactant may be a non-ionic surfactant. The surfactant may be a polyoxyethylated surfactant. The surfactant has a hydrophilic head which may be a hydrophilic chain, for example a polyoxyethylene chain or a polyhydroxylated chain.

The surfactant of course has a hydrophobic part and in particular a hydrophobic chain. The hydrophobic chain may be a hydrocarbon chain, for example having at least 6 carbon atoms and optionally at least 10 carbon atoms, and particularly of at least 12 carbon atoms; some hydrocarbon chains have no more than 22 carbon atoms, for example $C_{10}$-$C_{20}$, $C_{12}$-$C_{20}$ or $C_{15}$-$C_{20}$ hydrocarbon chains. It may be an alkyl chain, e.g. having a number of carbon atoms just mentioned. It may be an alkenyl chain comprising one or more carbon-carbon double bonds, e.g. having a number of carbon atoms just mentioned. The surfactant may comprise a hydrocarbon chain, e.g. alkyl chain or alkenyl chain that is substituted provided that it maintains a hydrophobic characteristic. There may for example be one or two substituents, for example a single substituent, e.g. selected from halogen (e.g. F or Cl), hydroxy, thiol oxo, nitro, cyano; hydroxy or thiol substituents may be esterified by for example a fatty acid. One class of surfactants comprise a hydrocarbon monosubstituted by hydroxy; optionally, at least a portion of the hydroxy groups of an aliquot of surfactant, e.g. of the surfactant in a bead, may be esterified by a fatty acid or mono-hydroxy fatty acid as disclosed herein or etherified by a fatty alcohol for example having at least 6 carbon atoms and optionally at least 10 carbon atoms, and particularly of at least 12 carbon atoms; some hydrocarbon chains have no more than 22 carbon atoms, for example $C_{10}$-$C_{20}$, $C_{12}$-$C_{20}$ or $C_{15}$-$C_{20}$ fatty alcohols.

The hydrophobic chain may be part of an esterified fatty acid $R^1$—COOH or of an etherified or esterified fatty ether $R^1$—COH where $R^1$ is the hydrophobic chain, e.g. as mentioned in the preceding paragraph. The ester-forming or, as the case may be, ether-forming group will typically comprise a hydrophilic chain.

As mentioned, the surfactant may have a hydrophilic chain and may be a non-ionic surfactant, and may satisfy both requirements. The hydrophilic chain may be a poly(ethyleneglycol), also known as poly(oxyethylene) or macrogol. The hydrophilic chain may be of the formula —(O—CH$_2$—CH$_2$)$_n$—OR where n is 5 or 6 to 50 and R is H or alkyl, e.g. ethyl or methyl. The invention includes implementations in which n is from 6 to 40, e.g. from 6 to 35. In some embodiments, n is from 6 to 25 and optionally is from 8 to 25 or from 8 to 15. In other embodiments, n is from 8 to 50 or from 8 to 40, e.g. from 10 to 50, 10 to 40 or 10 to 35. In a particular embodiment, n is 15. For all hydrophilic chains of the formula —(O—CH$_2$—CH$_2$)$_n$—OR, in one class of embodiments R is H.

The hydrophilic chain may be a polyhydroxylated chain (for example a $C_5$-$C_{20}$ e.g. $C_5$-$C_{10}$ chain), e.g. having a hydroxy group on the carbon atoms of the chain, for example a glucamide.

The micelle-forming surfactant may comprise a combination of a hydrophobic chain as described above and a hydrophilic chain as described above. It may therefore be, or comprise, a macrogol ester of a fatty acid as described herein or a macrogol ether of a fatty alcohol as described herein.

Micelle-forming surfactants comprising a hydrophobic chain and a hydrophilic chain can be selected from the group consisting of: macrogol esters; macrogol ethers; diblock copolymers; triblock copolymers; and amphiphilic polymers. In certain embodiments of the invention any combinations of the group are included within the invention.

Examples of macrogol esters which are suitable for use in the present invention are macrogol esters of fatty acids having at least 6 carbon atoms and optionally at least 10 carbon atoms, and particularly of at least 12 carbon atoms; some fatty acids have no more than 22 carbon atoms, for example $C_{10}$-$C_{20}$, $C_{12}$-$C_{20}$ or $C_{15}$-$C_{20}$ fatty acids. The fatty acids may be saturated or unsaturated but are in particular saturated. To be mentioned are macrogol 25 cetostearyl ether (Cremophor® A25); macrogol 6 cetostearyl ether (Cremophor® A6); macrogol glycerol ricinoleate 35 (Cremophor® EL); macrogol-glycerol hydroxystearate 40 (Cremophor® RH 40); macrogol-15-hydroxystearate (Solutol® HS 15). Examples of macrogol ethers which are suitable for use in the present invention are macrogol ethers of fatty alcohols having at least 6 carbon atoms and optionally at least 10 carbon atoms, and particularly of at least 12 carbon atoms; some fatty alcohols have no more than 22 carbon atoms, for example $C_{10}$-$C_{20}$, $C_{12}$-$C_{20}$ or $C_{15}$-$C_{20}$ fatty alcohols. The fatty alcohols may be saturate or unsaturated but are in one embodiment saturated.

Examples of amphiphilic polymers which are suitable for use in the present invention are: alkyl glucamides; fatty alcohol poly(ethoxyl)ates also known as polyethoxylated alkyl ethers; poly(ethoxyl)ated fatty acid esters (Myrj or Solutol); fatty amide polyethoxylate; fatty amine ethoxylate; alkylphenol ethoxylate; polyethoxylated sorbitan esters (polysorbates); polyethoxylated glycerides; or poly-glycerol esters.

Examples of copolymers, which are suitable for use in the present invention are: pluronics (poloxamers); polyvinylpyrollidone-polyvinylacetate (Plasdone S630); aminoalkyl methacrylate copolymer (Eudragit EPO); methacrylic acid-methyl methacrylate copolymer (Eudragit S100, L100); polycaprolactone-PEG; polycaprolactone-methoxy-PEG; poly(aspartic acid)-PEG; poly(benzyl-L-glutamate)-PEG; poly(D,L-lactide)methoxy-PEG; poly(benzyl-L-aspartate-PEG; or poly(L-lysine)-PEG In a preferred embodiment the micelle-forming surfactant cis a macrogol ester, more preferably a macrogol ester that conforms to the European Pharmacopoeia monograph number 2052 macrogol-15-hydroxystearate, such as Kolliphor® HS 15 marketed by BASF.

Kolliphor® HS 15 consists of polyglycol mono- and di-esters of 12-hydroxystearic acid and about 30% of free polyethylene glycol. The main components of the ester part have the following chemical structures:

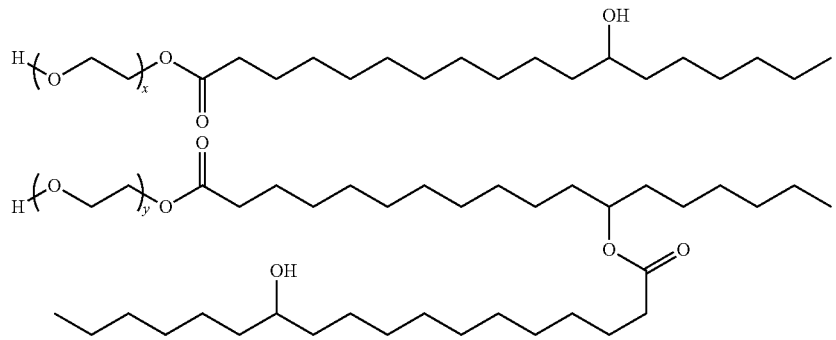

where x and y are integers and a small part of the 12-hydroxy group can be etherified with polyethylene glycol.

Suitable surfactants comprise those which during manufacture combine with the aqueous phase (including hydrogel-forming polymer) in an amount above their CMC to form a clear liquid. Kolliphor® HS 15 is such a surfactant.

In certain embodiments the weight ratio of the micelle-forming surfactant to the antigen is from 10:1 to 100:1, optionally from 50:1 to 100:1. In some embodiments, the ratio is from 80:1 to 90:1. In particular embodiments, the ratio is from 50:1 to 60:1.

In particular embodiments, the compositions of the invention comprise a combination of micelle-forming compounds. Such a combination of micelle-forming compounds may consist of two or more surfactants as mentioned in the preceding section of this specification. Alternatively, a surfactant may be combined with one or more other compounds at least potentially able to form micelles with the surfactant, optionally selected from cationic lipids and glycolipids, amongst others. As an additional option, a composition may comprise a plurality of surfactants as mentioned in the preceding section of this specification and one or more other compounds at least potentially able to form micelles with the surfactant, optionally selected from cationic lipids and glycolipids, amongst others.

The invention therefore includes compositions as described herein which comprise:

two or more micelle-forming surfactants, e.g. two or more surfactants having a hydrophobic chain and a hydrophilic chain;

a compound, e.g. a single compound or two or more compounds, selected from cationic lipids and glycolipids;

two or more micelle-forming surfactants and a compound, e.g. a single compound or two or more compounds, selected from cationic lipids and glycolipids.

A disperse phase which is or comprises a surfactant may enhance the absorption of an active ingredient, for example cyclosporin A, into the tissue of the GIT, for example by forming self-assembly structures, such as micelles, which are associated with the active ingredient and thus present the drug to the mucosa tissue of the GI tract in a form which enhances uptake/absorption in the tissue.

The oil phase may also include one or more volatile or non-volatile solvents, which may be the same or different from the solvent or co-solvent previously mentioned. Such solvents may for example remain in the formulation of the invention following processing e.g. initial dissolution of the components present in the core, and have no particular function in the core formulation. Alternatively, such solvents if present may function to maintain the cyclosporin a dissolved state (in solution) within the oil phase or to facilitate dispersion, egress etc. In other embodiments, the solvent may have partly or fully evaporated during processing and therefore be present in only minor quantities if at all. In a related embodiment, the solvent, particularly when a solvent which is both oil and water-soluble is used, may be partly or completely present in the aqueous phase of the core. An example of such a solvent is ethanol. Another example is transcutol which is already mentioned as a co-solvent.

Accordingly, the core may comprise a hydrogel-forming polymer matrix which forms a continuous phase and a disperse phase comprising an active ingredient, particularly a hydrophobic active ingredient, a high HLB non-ionic surfactant compound, a low HLB oil, and optionally a co-solvent. Optionally, the active ingredient may be a hydrophobic active ingredient.

In a particular embodiment the core is in the form of a solid colloid, the colloid comprising a continuous phase and a disperse phase, wherein the continuous phase comprises the hydrogel-forming polymer; wherein
the disperse phase is or comprises:
a pharmaceutically active ingredient, for example cyclosporin A or another hydrophobic active ingredient;
a medium chain mono-, di- and/or tri-glyceride, for example a medium chain triglyceride, particularly caprylic/capric triglyceride;
a polyethoxylated castor oil; and
a co-solvent (for example 2-(ethoxyethoxy)ethanol);
and wherein the continuous phase is or comprises:
a hydrogel-forming polymer matrix which is or comprises a hydrocolloid selected from carrageenan, gelatin, agar and pectin, or a combination thereof optionally selected from gelatin and agar or a combination thereof, more particularly the polymer of the a hydrogel-forming polymer matrix is or comprises gelatin;
a plasticiser, optionally a plasticiser selected from glycerin, a polyol for example sorbitol, polyethylene glycol and triethyl citrate or a mixture thereof, particularly sorbitol; and
an anionic surfactant, for example at least one surfactant selected from fatty acid salts, alkyl sulphates and bile salts, particularly an alkyl sulphate, for example sodium dodecyl sulphate.

In a further specific embodiment the core comprises a hydrogel-forming polymer matrix comprising gelatin in an amount of 300 to 700 mg/g, the core further comprising an active ingredient, medium chain mono-, di- and/or tri-glycerides (for example medium chain triglyceride, particularly caprylic/capric triglyceride) in an amount of 20 to 200 mg/g, and the core further comprises the following components:
co-solvent (for example 2-(ethoxyethoxy)ethanol) in an amount of 150 to 250 mg/g;

non-ionic surfactant in an amount of 80 to 200 mg/g; and
anionic surfactant in an amount of 15 to 50 mg/g,
wherein weights are based upon the dry weight of the core.

Suitably in the embodiment of the immediately preceding paragraph the active ingredient is cyclosporin and the cyclosporin A may be present in an amount of 60 to 180 mg/g, for example of 60 to 150 mg/g, 80 to 120 mg/g or particularly 80 to 100 mg/g. The non-ionic and anionic surfactants are as defined herein, for example an anionic surfactant selected from alkyl sulphates, carboxylates or phospholipids (particularly SDS); or a non-ionic surfactant selected from sorbitan-based surfactants, PEG-fatty acids, or glyceryl fatty acids or poloxamers. A particular non-ionic surfactant is a polyethoxylated castor oil (for example Cremophore EL).

The cores described above comprising hydrogel-forming polymer matrix and a pharmaceutically active ingredient, particularly cyclosporin A, are coated as described herein to provide a formulation according to the invention. A particular coating for these embodiments is a coating comprising
a first coating (sub-coating) which is or comprises a water-soluble cellulose ether, particularly hydroxypropylmethyl cellulose;
a second coating outside the first coating which is or comprises a modified release coating, particularly a pH independent modified release coating, more especially a coating comprising ethyl cellulose (e.g. Surelease®) still more particularly a coating comprising ethyl cellulose and a water-soluble polysaccharide such as pectin (e.g. a Surelease®-pectin coating as described herein); and wherein
the first coating is present in an amount corresponding to a weight gain due to the first coating in a range selected from: (i) from 8% to 12%, for example about 10%; or (ii) from 4% to 6%, for example about 5% by weight based upon the weight of the formulation prior to applying the first coating; and wherein
the second coating is present in an amount corresponding to a weight gain of the formulation due to the second coating selected from (a) from 10% to 12%, for example about 11% or about 11.5%; or (b) from 16% to 18%, for example about 17% by weight based upon the weight of the formulation prior to applying the second coating.

The disperse phase may comprise particles of an active ingredient dispersed in the matrix. The particles may be microparticles (e.g. 1-999 μm size) or nanoparticles (e.g. 1-999 nm size.) In particular, therefore, the disperse phase may comprise a particulate hydrophobic drug dispersed within the matrix.

Surfactant

The formulation may contain one or more surfactants, for example surfactants may be present in the core (including in the hydrogel-forming polymer matrix, and in the disperse phase or both). Surfactants may also be present in one or more of the coatings applied to the core.

Suitable surfactants can be anionic, cationic, zwitterionic, or non-ionic. In the description and claims of this specification, the term "surfactant" is employed as a contraction for "surface active agent". For the purposes of this description and claims, it is assumed that there are four major classifications of surfactants; therefore the surfactant may be: anionic, cationic, non-ionic, and amphoteric (zwitterionic). The non-ionic surfactant remains whole, has no charge in aqueous solutions, and does not dissociate into positive and negative ions. Anionic surfactants are water-soluble, have a negative charge and dissociate into positive and negative ions when placed in water. The negative charge lowers the surface tension of water and acts as the surface-active agent.

Cationic surfactants have a positive charge, and also dissociate into positive and negative ions when placed in water. In this case, the positive ions lower the surface tension of the water and act as the surfactant. The amphoteric (zwitterionic) surfactant assumes a positive charge in acidic solutions and performs as a cationic surfactant, or it assumes a negative charge in an alkaline solution and acts as an anionic surfactant.

The surfactant(s) may be selected from: anionic surfactants and combinations thereof; from non-ionic surfactants and combinations thereof; and from combination of an anionic surfactant (e.g. a single such surfactant or a plurality thereof) and a non-ionic surfactant (e.g. a single such surfactant or a plurality thereof).

Surfactants can also be classified according to their hydrophilic-lipophilic balance (HLB) which is a measure of the degree to which the surfactant is hydrophilic or lipophilic, determined by calculating values for the different regions of the molecule, as described (originally for non-ionic surfactants) by Griffin in 1949 and 1954 and later by Davies. The methods apply a formula to the molecular weight of the whole molecule and of the hydrophilic and lipophilic portions to give an arbitrary (semi-empirical) scale up to 40 although the usual range is between 0 and 20. An HLB value of 0 corresponds to a completely hydrophobic molecule, and a value of 20 would correspond to a molecule made up completely of hydrophilic components. The HLB value can be used to predict the surfactant properties of a molecule:

| HLB Value | Expected properties |
| --- | --- |
| 0 to 3 | antifoaming agent |
| from 4 to 6 | W/O emulsifier |
| from 7 to 9 | wetting agent |
| from 8 to 18 | an O/W emulsifier |
| from 13 to 15 | typical of detergents |
| 10 to 18 | solubiliser or hydrotrope |

Although HLB numbers are assigned to surfactants other than the non-ionic, for which the system was invented, HLB numbers for anionic, cationic, non-ionic, and amphoteric (zwitterionic) surfactants can have less significance and often represent a relative or comparative number and not the result of a mathematical calculation. This is why it is possible to have surfactants above the "maximum" of 20. HLB numbers can however be useful to describe the HLB requirement of a desired application for a given emulsion system in order to achieve good performance.

Non-Ionic Surfactants

The surfactant may be or comprise at least one surfactant selected from the following non-ionic surfactants.

PEG-fatty acid monoester surfactants, PEG-fatty acid diester surfactants, PEG-fatty acid monoester and diester surfactant mixtures, PEG glycerol fatty acid esters, transesterified products of oils and alcohols, lower alcohol fatty acid esters, polyglycerised fatty acids, propylene glycol fatty acid esters, mono and diglyceride surfactants, sterol and sterol derivative surfactants, PEG-sorbitan fatty acid esters, sorbitan fatty acid esters, polyethylene glycol alkyl ethers, sugar ester surfactants, polyethylene glycol alkyl phenol surfactants, POE-POP block copolymers, fatty acid salts, bile salts, phospholipids, phosphoric acid esters, carboxylates, acyl lactylates, sulphates and sulfonates, and cationic surfactants.

A PEG-fatty acid mono ester surfactant for example PEG 4-100 monolaurate, PEG 4-100 monooleate, PEG 4-100 monostearate, PEG-laurate, PEG-oleate, PEG stearate, and PEG ricinoleate. A PEG-fatty acid diester surfactant for example PEG dilaurate; PEG dioleate, PEG distearate, PEG dipalmitate. A mixture of PEG-fatty acid mono- and diesters.

A PEG glycerol fatty acid ester for example PEG glyceryl laurate, PEG glyceryl stearate, PEG glyceryl oleate.

PEG-sorbitan fatty acid esters for example PEG sorbitan laurate, PEG sorbitan monolaurate, PEG sorbitan monopalmitate, PEG sorbitan monostearate, PEG sorbitan tristearate, PEG sorbitan tetrastearate, PEG sorbitan monooleate, PEG sorbitan oleate, PEG sorbitan trioleate, PEG sorbitan tetraoleate, PEG sorbitan monoisostearate, PEG sorbitol hexaoleate, PEG sorbitol hexastearate.

Propylene glycol fatty acid esters for example propylene glycol monocaprylate, propylene glycol monolaurate, propylene glycol oleate, propylene glycol myristate, propylene glycol monostearate, propylene glycol hydroxy stearate, propylene glycol ricinoleate, propylene glycol isostearate, propylene glycol monooleate, propylene glycol dicaprylate/dicaprate, propylene glycol dioctanoate, propylene glycon caprylate/caprate, propylene glycol dilaurate, propylene glycol distearate, propylene glycol dicaprylate, propylene glycol dicaprate.

A sorbitan fatty acid ester for example sorbitan monolaurate, sorbitan monopalmitate, sorbitan monooleate, sorbitan monostearate, sorbitan trioleate, sorbitan sesquioleate, sorbitan tristearate, sorbitan monoisostearate, sorbitan sesquistearate.

Lower alcohol fatty acid esters for example ethyl oleate, isopropyl myristate, isopropyl palmitate, ethyl linoleate, isopropyl linoleate.

Polyoxyethylene-polyoxypropylene block copolymers for example poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407.

Polyglycerised fatty acids for example polyglyceryl stearate, polyglyceryl oleate, polyglyceryl isostearate, polyglyceryl laurate, polyglyceryl ricinoleate, polyglyceryl linoleate, polyglyceryl pentaoleate, polyglyceryl dioleate, polyglyceryl distearate, polyglyceryl trioleate, polyglyceryl septaoleate, polyglyceryl tetraoleate, polyglyceryl decaisostearate, polyglyceryl decaoleate, polyglyceryl monooleate, dioleate, polyglyceryl polyricinoleate.

PEG alkyl ethers for example PEG oleyl ether, PEG lauryl ether, PEG cetyl ether, PEG stearyl ether.

PEG alkyl phenols for example PEG nonyl phenol, PEG octyl phenol ether.

Transesterification products of alcohol or polyalcohol with natural or hydrogenated oils for example PEG castor oil, PEG hydrogenated castor oil, PEG corn oil, PEG almond oil, PEG apricot kernel oil, PEG olive oil, PEG-6 peanut oil, PEG hydrogenated palm kernel oil, PEG palm kernel oil, PEG triolein, PEG corn glycerides, PEG almond glycerides, PEG trioleate, PEG caprylic/capric triglyceride, lauroyl macrogol glyceride, stearoyl macrogol glyceride, mono, di, tri, tetra esters of vegetable oils and sorbitol, pentaerythrityl tetraisostearate, pentaerythrityl distearate, pentaerythrityl tetraoleate, pentaerythrityl tetrastearate, pentaerythrityl tetracaprylate/tetracaprate, pentaerythrityl tetraoctanoate.

Oil-soluble vitamins for example vitamins A, D, E, K, and isomers, analogues, and derivatives thereof. The derivatives include, for example, organic acid esters of these oil-soluble vitamin substances, for example the esters of vitamin E or vitamin A with succinic acid. Derivatives of these vitamins include tocopheryl PEG-1000 succinate (Vitamin E TPGS) and other tocopheryl PEG succinate derivatives with various molecular weights of the PEG moiety, for example PEG 100-8000.

Sterols or sterol derivatives (e.g. esterified or etherified sterols as for example PEGylated sterols) for example cholesterol, sitosterol, lanosterol, PEG cholesterol ether, PEG cholestanol, phytosterol, PEG phytosterol.

Sugar esters for example sucrose distearate, sucrose distearate/monostearate, sucrose dipalmitate, sucrose monostearate, sucrose monopalmitate, sucrose monolaurate, alkyl glucoside, alkyl maltoside, alkyl maltotrioside, alkyl glycosides, derivatives and other sugar types: glucamides.

Carboxylates (in particular carboxylate esters) for example ether carboxylates, succinylated monoglycerides, sodium stearyl fumarate, stearoyl propylene glycol hydrogen succinated, mono/diacetylated tartaric acid esters of mono- and diglycerides, citric acid esters of mono-, diglycerides, glyceryl-lacto esters of fatty acids; acyl lactylates: lactylic esters of fatty acids, calcium/sodium stearoyl-2-lactylate calcium/sodium stearoyl lactylate, alginate salts, propylene glycol alginate.

A fatty acid monoglyceride, diglyceride or triglyceride or a combination thereof.

Anionic Surfactants

Anionic surfactants may be selected from following anionic surfactants.

Fatty acid salts and bile salts for example sodium caproate, sodium caprylate, sodium caprate, sodium laurate, sodium myristate, sodium myristoleate, sodium palmitate, sodium palmitoleate, sodium oleate, sodium ricinoleate, sodium linoleate, sodium linolenate, sodium stearate, sodium lauryl sulfate, sodium tetradecyl sulfate, sodium lauryl sarcosinate, sodium dioctyl sulfosuccinate; sodium cholate, sodium taurocholate, sodium glycocholate, sodium deoxycholate, sodium taurodeoxycholate, sodium glycodeoxycholate, sodium ursodeoxycholate, sodium chenodeoxycholate, sodium taurochenodeoxycholate, sodium glyco chenodeoxycholate, sodium cholylsarcosinate, sodium N-methyl taurocholate Phospholipids for example egg/soy lecithin, cardiolipin, sphingomyelin, phosphatidylcholine, phosphatidyl ethanolamine, phosphatidic acid, phosphatidyl glycerol, phosphatidyl serine.

Phosphoric acid esters having the general formula RO—PO$_3^-$M$^+$ where the R group is an ester forming group, e.g. an alkyl, alkenyl or aryl group optionally substituted by a PEG moiety through which the alkyl, alkenyl or aryl group is coupled to the phosphate moiety. R may be a residue of a long chain (e.g. >C9) alcohol or a phenol. Specific examples include diethanolammonium polyoxyethylene-10 oleyl ether phosphate, esterification products of fatty alcohols or fatty alcohol ethoxylates with phosphoric acid or anhydride.

Sulfates and sulfonates (in particular esters thereof) for example ethoxylated alkyl sulfates, alkyl benzene sulfones, α-olefin sulfonates, acyl isethionates, acyl taurates, alkyl glyceryl ether sulfonates, octyl sulfosuccinate disodium, disodium undecylenamideo-MEA-sulfosuccinate, alkyl phosphates and alkyl ether phosphates.

Cationic Surfactants

Cationic surfactants may be selected from the following cationic surfactants.

Hexadecyl triammonium bromide, dodecyl ammonium chloride, alkyl benzyldimethylammonium salts, diisobutyl phenoxyethoxydimethyl benzylammonium salts, alkylpyridinium salts; betains (trialkylglycine): lauryl betaine (N-lauryl,N,N-dimethylglycine); ethoxylated amines: polyoxyethylene-15 coconut amine, alkyl-amines/diamines/quaternary amines and alkyl ester.

Emulsifiers

The surfactant may act as an emulsifier such surfactants include non-ionic emulsifiers, for example selected from: a mixture of triceteareth-4 phosphate, ethylene glycol palmitostearate and diethylene glycol palmitostearate (for example sold under the trade mark SEDFOS™ 75); sorbitan esters, e.g. sorbitan monooleate, sorbitan monolaurate, sorbitan monopalmitate, sorbitan monostearate (for example products sold under the trade mark Span®), PEG-8 beeswax e.g. sold under the trade mark Apifil®; a mixture of cetyl alcohol, ceteth-20 and steareth-20 (for example Emulcire™ 61 WL 2659); a mixture of glyceryl monostearate EP/NF and PEG-75 palmitostearate (for example Gelto™ 64); a mixture of PEG-6 stearate and PEG-32 stearate (for example Tefose® 1500); a mixture of PEG-6 palmitostearate, ethylene glycol palmitostearate, and PEG-32 palmitostearate (e.g. Tefose® 63); triglycerol diisostearate (for example products sold under the trade mark Plurol Diisostearique®); polyglyceryl-3 dioleate (for example products sold under the trade mark Plurol® Oleique).

Other Excipients

The formulation optionally contains one or more of the following additional substances or categories of substances. For example, the formulation may contain a protectant such as, for example, a proteolytic enzyme inhibitor or a protector against acid degradation or both (e.g. an alkali for example sodium hydroxide); an adhesive entity such as, for example, a muco- or bio-adhesive; excipients to maximize solubility of the active ingredient; excipients to maximize permeability of the active ingredient in the GIT. Typical excipients for enhancing the permeability of the epithelial barrier include but are not limited to sodium caprate, sodium dodecanoate, sodium palmitate, SNAC, chitosan and derivatives thereof, fatty acids, fatty acid esters, polyethers, bile salts, phospholipids, alkyl polyglucosides, hydroxylase inhibitors, antioxidants (e.g. ascorbic acid) and/or nitric oxide donors. The preceding list is of particular interest to enhance permeability in the ileum.

To enhance permeability in the colon, typical excipients include, but not limited to sodium caprate, sodium dodecanoate, sodium palmitate, SNAC, chitosan and derivatives thereof, fatty acids, fatty acid esters, polyethers, bile salts, phospholipids, alkyl polyglucosides, hydroxylase inhibitors, antioxidants and/or nitric oxide donors, including nitric oxide donor groups covalently attached to various pharmaceutically active ingredients.

The formulation may further comprise excipients to enhance the therapeutic potential of an active ingredient, for example cyclosporin A or another immunosuppressant, in the ileum and colon including, but not limited to absorption limiters, essential oils such as, for example, omega 3 oils, natural plant extracts such as, for example, neem, ion-exchange resins, bacteria degradable conjugation linkers such as, for example, azo bonds, polysaccharides such as, for example, amylose, guar gum, pectin, chitosan, inulin, cyclodextrins, chondroitin sulphate, dextrans, guar gum and locust bean gum, nuclear factor kappa B inhibitors, acids such as, for example, fumaric acid, citric acid and others, as well as modifications thereof.

The formulation may further comprise excipients to reduce systemic side effects associated with absorption of certain active, for example cyclosporin or other immunosuppressants, in the GIT, such as the small intestine, including, but not limited to, antioxidants, such as, for example, curcuminoids, flavanoids or more specifically including curcumin, beta-carotene, α-tocopherol, ascorbate or lazaroid.

The formulation may further or separately comprise antioxidants (such as, for example, ascorbic acid or BHT—butyl hydroxy toluene) taste-masking or photosensitive components or photoprotective components. Antioxidants may be incorporated in the aqueous phase (e.g. hydrophilic antioxidants) or in the disperse phase of the core (e.g. hydrophobic antioxidants such as, for example, vitamin E) for example up to 1% by weight, preferably between 0.01 and 0.50% by weight, more preferably between 0.10 to 0.20% by weight.

The formulation may further comprise immune-enhancing nutrients such as vitamins A/B/C/E; carotenoids/beta-carotene and iron, manganese, selenium, zinc, especially when the formulation contains an immunosuppressant, as in the case of an immunosuppressant targeted to the ileum and/or colon, e.g. the colon. Such nutrients may be present in formulation, or if the formulation has a coating, for example if it is the form of a bead, the nutrients may be included in the coating.

The formulation may also include other well know excipients used in pharmaceutical formulations including colorants, taste masking agents, diluents, fillers, binders etc. The presence of such optional additional components will of course depend upon the particular dosage form adopted.

Active Ingredients

The active ingredients suitable for use in the pharmaceutical compositions and methods of the present invention are not particularly limited, as the compositions are surprisingly capable of delivering active ingredients with widely differing physico-chemical properties whilst still achieving have a higher total release of active from the formulation and/or a greater rate of release of the active compared to a formulation which does not have the coating. The active ingredient may be hydrophilic, lipophilic, amphiphilic or hydrophobic. The active ingredient may be solubilised in the formulation. The active ingredient may be suspended in the formulation. Active ingredients can be any compound or mixture of compounds having therapeutic or other value when administered to an animal, particularly to a human or other mammal (the formulations of the invention are in particular for administration to humans or other mammals), for example drugs, nutrients, cosmeceuticals, diagnostic agents, nutritional agents. In particular, the active ingredient is pharmaceutically active. It should be appreciated that the categorisation of an active ingredient as hydrophilic or hydrophobic may change, depending upon the particular salts, isomers, analogues and derivatives used. The active ingredient may be one mentioned in the examples of this specification.

The active ingredient agent may be hydrophobic. Hydrophobic active ingredients are compounds with little or no water solubility. Intrinsic water solubilities (i.e., water solubility of the non-ionised form) for hydrophobic active ingredients may be less than about 1% by weight, and typically less than about 0.1% or 0.01% by weight. The active ingredient is in particular a hydrophobic drug.

Suitable hydrophobic active ingredients are not limited by therapeutic category, and can be, for example, analgesics, anti-inflammatory agents, antihelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-blockers, cardiac inotropic agents, corticosteroids, diuretics, anti-parkinsonian agents, gastro-intestinal agents, histamine receptor antagonists, hydroxylase inhibitors (e.g. asparaginyl hydroxylase inhibitors, prolyl hydroxylase inhibitors), keratolytics, lipid regulating agents, anti-anginal agents, COX-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

Specific, non-limiting examples of suitable hydrophobic active ingredients are: acetretin, albendazole, albuterol, aminoglutethimide, amiodarone, amlodipine, amphetamine, amphotericin B, atorvastatin, atovaquone, azithromycin, baclofen, beclomethasone, benazepril, benzonatate, betamethasone, bicalutanide, budesonide, bupropion, busulfan, butenafine, calcifediol, calcipotriene, calcitriol, camptothecin, candesartan, capsaicin, carbamazepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporins, danazol, dantrolene, dexchlorpheniramine, diclofenac, dicoumarol, digoxin, dehydroepiandrosterone, dihydroergotamine, dihydrotachysterol, dirithromycin, DMOG, donezepil, efavirenz, eposartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, steroids, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, and zopiclone. Of course, salts, isomers and derivatives of the above-listed hydrophobic active ingredients may also be used, as well as mixtures.

Among the above-listed hydrophobic active ingredients, there may in particular be mentioned: celecoxib, cyclosporins and especially cyclosporin A, sirolimus, steroids, tacrolimus, pharmaceutically acceptable salts, isomers and derivatives thereof, and mixtures thereof.

The active ingredient may be hydrophilic. Amphiphilic compounds are also included within the class of hydrophilic active ingredients. Apparent water solubilities for hydrophilic active ingredients are greater than about 0.1% by weight, and typically greater than about 1% by weight. The hydrophilic active ingredient is in particular a hydrophilic drug. The hydrophilic active ingredient may be a cosmeceutical, a diagnostic agent, or a nutritional agent.

Suitable hydrophilic active ingredients are not limited by therapeutic category, and can be, for example, analgesics, anti-inflammatory agents, antihelminthics, anti-arrhythmic agents, anti-bacterial agents, anti-viral agents, anti-coagulants, anti-depressants, anti-diabetics, anti-epileptics, antifungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-blockers, cardiac inotropic agents, corticosteroids, diuretics, anti-parkinsonian agents, gastro-intestinal agents, histamine receptor antagonists, hydroxylase inhibitors (e.g. asparaginyl hydroxylase inhibitors, prolyl hydroxylase inhibitors), keratolytics, lipid regulating agents, anti-anginal agents, COX-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

Likewise, the hydrophilic active ingredient can be a cytokine, a peptidomimetic, a peptide, a protein, a toxoid, a serum, an antibody, a vaccine, a nucleoside, a nucleotide, a portion of genetic material, a nucleic acid, or a mixture thereof.

Specific, non-limiting examples of suitable hydrophilic active ingredients include: acarbose; acyclovir; acetyl cysteine; acetylcholine chloride; alatrofloxacin; alendronate; aglucerase; amantadine hydrochloride; ambenomium; amifostine; amiloride hydrochloride; aminocaproic acid; amphotericin B; antihemophilic factor (human), antihemophilic factor (porcine); antihemophilic factor (recombinant), aprotinin; asparaginase; atenolol; atracurium besylate; atropine; azithromycin; aztreonam; BCG vaccine; bacitracin; becalermin; belladona; bepridil hydrochloride; bleomncin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotaxime; cefoxitin sodium; ceftizoxime; ceftriaxone; cefuroxime axetil; cephalexin; cephapirin sodium; cholera vaccine; chorionic gonadotropin; cidofovir; cisplatin; cladribine; clidinium bromide; clindamycin and clindamycin derivatives; ciprofloxacin; clodronate; colistimethate sodium; colistin sulfate; corticotropin; cosyntropin; cromolyn sodium; cytarabine; dalteparin sodium; danaparoid; desferrioxamine; denileukin diflitox; desmopressin; diatrizoate meglumine and diatrizoate sodium; dicyclomine; didanosine; dirithromycin; dopamine hydrochloride; dornase alpha; doxacurium chloride; doxorubicin; etidronate disodium; enalaprilat; enkephalin; enoxaparin; enoxaprin sodium; ephedrine; epinephrine; epoetin alpha; erythromycin; esmolol hydrochloride; factor IX; famciclovir; fludarabine; fluoxetine; foscarnet sodium; ganciclovir; granulocyte colony stimulating factor, granulocyte-macrophage stimulating factor; growth hormones—recombinant human; growth hormone—bovine; gentamycin; glucagon; glycopyrolate; gonadotropin releasing hormone and synthetic analogues thereof; GnRH; gonadorelin; grepafloxacin; haemophilus B conjugate vaccine; hepatitis A virus vaccine inactivated; hepatitis B virus vaccine inactivated; heparin sodium; hydralazine, indinavir sulfate; influenza virus vaccine; interleukin-2; interleukin-3; insulin-human, insulin lispro; insulin porcine; insulin NPH; insulin aspart; insulin glargine; insulin detemir; interferon alpha; interferon beta; ipratropium bromide; ifosfamide; Japanese encephalitis virus vaccine; lamivudine; leucovorin calcium; leuprolide acetate, levofloxacin; lincomycin and lincomycin derivatives; lobucavir; lomefloxacin; loracarbef; mannitol; measles virus vaccine; meningococcal vaccine; menotropins; mepenzolate bromide; mesalamine; methenamine; methotrexate; methscopolamine; metformin hydrochloride; metoprolol; mezocillin sodium; mivacurium chloride; mumps viral vaccine; nedocromil sodium; neostigmine bromide; neostigmine methyl sulfate; neurontin; norfloxacin; octreotide acetate; ofloxacin; olpadronate; oxytocin; pamidronate disodium; pancuronium bromide; paroxetine; perfloxacin; pentamidine isethionate; pentostatin; pentoxifylline; periciclovir; pentagastrin; pentholamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymyxin B sulfate; pralidoxime chloride; pramlintide, pregabalin; propafenone; propenthaline bromide; pyridostigmine bromide; rabies vaccine; residronate; ribavarin; rimantadine hydrochloride; rotavirus vaccine; salmeterol xinafoate; sinealide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valacyclovir; valsartan; varicella virus vaccine live; vasopressin and vasopressin derivatives; vecuronium bromide; vinblastine; vincristine; vinorelbine; vitamin B12; warfarin sodium; yellow fever vaccine; zalcitabine; zanamivir; zolendronate; zidovudine; pharmaceutically acceptable salts, isomers and derivatives thereof; and mixtures thereof.

Among the above-listed hydrophilic active ingredients, there may be mentioned in particular hydralazine and mesalamine.

Shape, Size and Geometry

The formulation of the invention can be formed into a limitless number of shapes and sizes. In the section below describing the process for making the formulation, various methods are given including pouring or introducing a fluid dispersion into a mould where it hardens or can be caused to harden. Thus the formulation can be created in whichever form is desired by creating an appropriate mould (e.g. in the shape of a disc, pill or tablet). However, it is not essential to use a mould. For example, the formulation may be formed into a sheet e.g. resulting from pouring a fluid dispersion onto a flat surface where it hardens or can be caused to harden.

Preferably, the formulation may be in the form of spheres or spherical-like shapes made as described below. Preferably, the formulation of the invention is in the form of substantially spherical, seamless minibeads. The absence of seams on the minibead surface is an advantage e.g. in further processing, for example coating, since it allows more consistent coating, flowability etc. The absence of seams on the minibeads also enhances consistency of dissolution of the beads.

The preferred size or diameter range of minibeads according to the invention can be chosen to avoid retention in the stomach upon oral administration of the minibeads. Larger dosage forms are retained for variable periods in the stomach and pass the pyloric sphincter only with food whereas smaller particles pass the pylorus independently of food. Selection of the appropriate size range (see below) thus makes the therapeutic effect post-dosing more consistent. Compared to a single large monolithic oral format such as, for example, a traditional compressed pill, a population of beads released into the GI tract (as foreseen by the dosage form of the present invention) permits greater intestinal lumen dispersion so enhancing absorption via exposure to greater epithelial area, and achieves greater topical coating in certain parts of the GI tract for example the colon). Reduction of residence time in the ileo-caecal junction is another potential advantage.

The formulation of the invention is preferably monolithic meaning internally (i.e. cross-sectionally) homogeneous, excluding a possible thin skin of matrix material and excluding any coating layers.

The minibeads provided for by the formulation of the present invention generally range in diameter from 0.5 mm to 10 mm with the upper limit preferably 5 mm, e.g. 2.5 mm A particularly convenient upper limit is 2 mm or 1.7 mm. The lower limit can preferably be 1 mm, e.g. 1.2 mm, more preferably from 1.3 mm, most preferably from 1.4 mm. In one embodiment the diameter is from 0.5 to 2.5 mm, for example from 1 mm to 3 mm, 1 mm to 2 mm, 1.2 mm to 3 mm or 1.2 mm to 2 mm. The minibeads may have a diameter of no more than 2.5 mm, irrespective of their minimum size. The beads may have a diameter of no more than 2 mm, irrespective of their minimum size.

A minibead as described herein may have an aspect ratio of no more than 1.5, e.g. of no more than 1.3, for example of no more than 1.2 and, in particular, of from 1.1 to 1.5, 1.1 to 1.3 or, 1.1 to 1.2. A population of minibeads as described herein, e.g. at least 10 beads, may have an average aspect ratio of no more than 1.5, e.g. of no more than 1.3, for example of no more than 1.2 and, in particular, of from 1 to 1.5, 1 to 1.3 or 1 to 1.2. The aspect ratios mentioned in this paragraph optionally apply to coated minibeads and optionally apply to uncoated minibeads. Average aspect ratio is suitably determined for a population of minibeads, e.g. at least 10 minibeads, using a particle size analyser, for example an Eyecon™ particle characteriser of Innopharma Labs, Dublin 18, Ireland.

The minibeads of the disclosure may, therefore, have a size as disclosed above and an aspect ratio of from 1 to 1.5. The beads of the disclosure may have a size as disclosed above and an aspect ratio of no more than 1.3, for example of no more than 1.2 and, in particular, of from 1.1 to 1.5, 1.1 to 1.3 or, 1.1 to 1.2.

Bead size (diameter) may be measured by any suitable technique, for example microscopy, sieving, sedimentation, optical sensing zone method, electrical sensing zone method or laser light scattering. For the purposes of this specification, bead size is measured by analytical sieving in accordance with USP General Test <786> Method I (USP 24-NF 18, (U.S. Pharmacopeial Convention, Rockville, Md., 2000), pp. 1965-1967).

In embodiments, minibeads of the invention are monodisperse. In other embodiments, minibeads of the invention are not monodisperse. By "monodisperse" is meant that for a population of beads (e. g. at least 100, more preferably at least 1000) the minibeads have a coefficient of variation (CV) of their diameters of 35% or less, optionally 25% or less, for example 15% or less, such as e.g. of 10% or less and optionally of 8% or less, e.g. 5% or less. A particular class of polymer beads has a CV of 25% or less. CV when referred to in this specification is defined as 100 times (standard deviation) divided by average where "average" is mean particle diameter and standard deviation is standard deviation in particle size. Such a determination of CV is performable using a sieve.

The invention includes minibeads having a CV of 35% and a mean diameter of 1 mm to 2 mm, e.g. 1.5 mm. The invention also includes minibeads having a CV of 20% and a mean diameter of 1 mm to 2 mm, e.g. 1.5 mm, as well as minibeads having a CV of 10% and a mean diameter of 1 mm to 2 mm, e.g. 1.5 mm. In one class of embodiments, 90% of minibeads have a diameter of from 0.5 mm to 2.5 mm, e g of from 1 mm to 2 mm.

Dosage Forms

The formulation of the invention is prepared as an orally administrable dosage form suitable for pharmaceutical use. In those embodiments where the formulation is in the form of a minibead, the present invention provides for a dosage form comprising a plurality of the minibeads for example as a capsule, a tablet, a sprinkle or a sachet.

In embodiments the dosage form comprising a population of beads may be presented in a single unit dosage form e.g. contained in a single hard gel capsule which releases the beads e.g. in the stomach. Alternatively the beads may be presented in a sachet or other container which permits the beads to be sprinkled onto food or into a drink or to be administered via a feeding tube for example a naso-gastric tube or a duodenal feeding tube. Alternatively, the beads may be administered as a tablet for example if a population of beads is compressed into a single tablet as described below. Alternatively, the beads may be filled e.g. compressed into a specialist bottle cap or otherwise fill a space in a specialised bottle cap or other element of a sealed container (or container to be sealed) such that e.g. on twisting the bottle cap, the beads are released into a fluid or other contents of the bottle or vial such that the beads are disperse (or dissolve) with or without agitation in such contents. An example is the Smart Delivery Cap manufactured by Humana Pharma International (HPI) S.p.A, Milan, Italy.

The dosage form may be formulated in such a way so that the beads of the invention can be further developed to create a larger mass of beads e.g. via compression (with appropriate oil or powder-based binder and/or filler known to persons skilled in the art. The larger (e.g. compressed) mass may itself take a variety of shapes including pill shapes, tablet shapes, capsule shapes etc. A particular problem which this version of the bead embodiment solves is the "dead space" (above the settled particulate contents) and/or "void space" (between the particulate content elements) typically found in hard gel capsules filled with powders or pellets. In such pellet- or powder-filled capsules with dead/void space, a patient is required to swallow a larger capsule than would be necessary if the capsules contained no such dead space. The beads of this embodiment of the invention may readily be compressed into a capsule to adopt the inner form of whichever capsule or shell may be desired leaving much reduced, e.g. essentially no, dead/void space. Alternatively the dead or void space can be used to advantage by suspending beads in a vehicle such as, for example, an oil which may be inert or may have functional properties such as, for example, permeability enhancement or enhanced dissolution or may comprise an active ingredient being the same or different from any active ingredients in the bead. For example, hard gelatin or HPMC capsules may be filled with a liquid medium combined with uncoated and/or coated beads. The liquid medium may be one or more of the surfactant phase constituents described herein or it may be one or more surfactants. Particularly preferred but non-limiting examples are corn oil, sorbitane trioleate (sold under the trade mark SPAN 85), propylene glycol dicaprylocaprate (sold under the trade mark Labrafac), 2-(2-ethoxy-ethoxy)ethanol (sold under the trade mark Transcutol P) and polysorbate 80 (sold under the trade mark Tween 80).

In a representative embodiment the bead of the dosage form is prepared as described herein for example by mixing together at least the following materials: a hydrogel-forming polymer; and cyclosporin A, suitably cyclosporin A dissolved in a hydrophobic material, such as an oil to form a dispersion of the cyclosporin A in the hydrogel-forming polymer. The dispersion is immobilized within the solidified bead by ejection from a single orifice nozzle into a suitable cooling liquid. Following removal of the drying liquid the bead is coated with a modified release coating (the second coating) (suitably with a sub-coat under the modified release coating), the coated bead is the filled into a gelatin or HPMC capsule suitable for pharmaceutical use.

Suitably the dosage form is prepared as a unit dosage form containing from for oral administration comprising from 0.1 mg to 1000 mg, optionally from 1 mg to 500 mg, for example 10 mg to 300 mg, or 25 to 250 mg suitably about 25 mg, about 35 mg, about 50 mg, about 75 mg, about 100 mg, about 150 mg, about 180 mg, about 200 mg, about 210 mg or about 250 mg cyclosporin A Determination of Contents and Distribution of Formulations The identity and/or distribution of one or more of the components of a formulation according to the invention can be determined by any method known to those skilled in the art. The distribution of one or more components of a formulation can, for example, be determined by near-infrared (NIR) chemical imaging technology. NIR chemical imaging technology can be used to generate images of the surface or cross section of a formulation, for example a minibead. The image produced by this technique shows the distribution of one or more components of the formulation. In addition to NIR chemical imaging technology, the distribution of one or more components of a formulation such as minibead, for example, be determined by time-of-flight secondary ion mass spectrometry (ToFSIMS). ToFSIMS imaging can reveal the distribution of one or more components within the formulation. The images produced by ToFSIMS analysis or NIR analysis can show the distribution of components across a surface of the formulation or a cross section of the formulation. The methods described in this paragraph are applicable, for example, to formulations comprising a polymer matrix, e.g. a dried, colloid, solution or dispersion.

Manufacturing Processes

Various methods may be used to prepare the formulations of the invention.

In those embodiments where the formulation comprises an active ingredient in a water-insoluble polymer matrix, a basic method for making the core is to mix a fluid form of the matrix material, for example a water-insoluble polymer matrix material (eg poly(amides), poly(amino-acids), hyaluronic acid; lipoproteins; poly(esters), poly(orthoesters), poly(urethanes) or poly(acrylamides), poly(glycolic acid), poly(lactic acid) and corresponding co-polymers (poly (lactide-co-glycolide acid; PLGA); siloxane, polysiloxane; dimethylsiloxane/methylvinylsiloxane copolymer; poly(dimethylsiloxane/methylvinyl-siloxane/methylhydrogensiloxane) dimethylvinyl or trimethyl copolymer; silicone polymers; alkyl silicone; silica, aluminium silicate, calcium silicate, aluminium magnesium silicate, magnesium silicate, diatomaceous silica etc as described more generally elsewhere herein), with an active ingredient to form a mixture that may take the form of a suspension, solution or a colloid. The mixture is processed to form a core. For example the formulation may be shaped into the desired form using a molding or hot-melt extrusion process to form beads.

Methods for preparing cores comprising an active ingredient and a water-soluble polymer matrix are described below. Generally these cores are coated to give the final formulation of the invention.

Generally, the manufacturing processes described herein comprise mixing of liquid(s). Such mixing processes must be performed at temperatures at which the substances to be mixed in the liquid state are in liquid form. For example, thermoreversible gelling agents must be mixed at a temperature where they are in the liquid state, for example at a temperature of 50 to 75° C., for example 50 to 70° C., or 55-75° C., e.g. 60-70° C. and in particular embodiments about 55° C. or 65° C. in the case of mixing formulations comprising aqueous gelatin. Similarly other components of the formulation may need to be heated to melt the component for example waxes or surfactants which may be used in the disperse phase.

Cores comprising a hydrogel-forming polymer and an active ingredient as disclosed herein may be made by mixing materials comprising for example water, a hydrogel-forming polymer and a surfactant to form an aqueous continuous phase, and mixing a disperse phase. At least one of the aqueous phase and the disperse phase comprises a pharmaceutically active ingredient, the active ingredient may be dissolved in the phase which contains it, for example both phases may be a clear liquid before they are mixed together. For example, the disperse phase may comprise an active ingredient, (for example a disperse phase comprising an oil, an optional solvent, cyclosporin A or another hydrophobic active and a surfactant) with the aqueous phase to form a colloid; the active ingredient may in particular be a hydrophobic active ingredient e.g. cyclosporin A or alternatively it may be a hydrophilic active ingredient, or a combination comprising e.g. a hydrophobic active ingredient and a hydrophilic active ingredient. The colloid may have the form of an emulsion or microemulsion wherein the disperse phase is dispersed in the aqueous continuous phase. The hydrogel-forming polymer is then caused or allowed to gel. Suitably, the process includes formulating or processing the core formulation into a desired form, e.g. a bead (also termed a minibead), which forming process may comprise moulding but preferably comprises ejecting the aqueous colloid through a single orifice nozzle to form droplets which are caused or allowed to pass into a cooling medium, e.g. a water-immiscible cooling liquid, in which the droplets cool to form for e.g. beads.

The mixing of the materials may comprise mixing an aqueous premix (or aqueous phase) and a disperse phase premix (e.g. oil phase premix), wherein the aqueous premix comprises water and water-soluble substances whilst the disperse phase premix may comprise a vehicle containing an active ingredient. The vehicle may be a hydrophobic liquid, for example a liquid lipid, or it may be or comprise a material, for example a surfactant, for forming self-assembly structures. In particular, a disperse phase premix may comprise an active ingredient, for example cyclosporin A, oil and other oil soluble components for example surfactant and an optional solvent. The premixes may contain one or more surfactants suitable for the phase they are to form, as previously mentioned.

The aqueous premix comprises, or usually consists of, a solution in water of water-soluble constituents, namely the hydrogel-forming polymer and water-soluble excipient(s), and any water-soluble active ingredient destined for the matrix phase. The aqueous premix may include a plasticiser for the hydrogel-forming polymer, as described elsewhere in this specification. The aqueous premix may include a surfactant, e.g. to increase polymer viscosity and improve emulsification and thereby help prevent precipitation of active agent during processing. SDS is an example of such a surfactant. In any event, the constituents of the aqueous premix may be agitated for a period sufficient to dissolve/melt the components, for example, from 1 hour to 12 hours to form the completed aqueous premix.

The disperse phase pre-mix may comprise a hydrophobic active ingredient as a dispersion or preferably a solution in a vehicle as described above, for example in a liquid comprising an oil or in a liquid comprising component(s) of self-assembly structures. For example an oil phase pre-mix may therefore be a liquid lipid, for example a medium chain triglyceride (MCT) formulation, the medium chain triglyceride(s) being one or more triglycerides of at least one fatty acid selected from $C_6$-$C_{12}$ fatty acids, and cyclosporin A or another hydrophobic active ingredient. Suitably an oil phase pre-mix is stirred at ambient temperature to form a solution of the active ingredient in the oil. In some embodiments, the components of the oil phase premix are mixed (or otherwise agitated) for a period of, for example, 10 minutes to 3 hours to form the premix. The disperse phase premix may comprise a hydrophilic active ingredient in particulate form, for example microparticles or nanoparticles; the particulate active ingredient may for example be suspended in a vehicle comprising or consisting of an oil, e.g. a liquid lipid.

The two premixes may be combined and agitated, for example for a period of a few seconds to an hour, for example from 30 seconds to 1 hour, suitably 5 mins to an hour, to form a dispersion of the disperse phase in an aqueous hydrogel-forming polymer, which dispersion may then be further processed to form the final formulation. The two premixes may be combined into the dispersion by agitation in a mixing vessel; they may additionally or alternatively be combined in a continuous flow mixer.

Where the disperse phase is particulate, the manufacturing process may not involve combining two liquid premixes but may instead comprise combining the particulate ingredient directly into the liquid which is to form the continuous phase (water, hydrogel-forming polymer and any other constituents), or into a precursor of the liquid. There is thereby formed a liquid comprising dispersed particulate active ingredient, and this dispersion is then formed into the core by a process which comprises causing or allowing the polymer to gel.

The basic method for making a core comprising an active ingredient and hydrogel-forming polymer matrix, therefore, is to mix a liquid form (preferably a solution) of the hydrogel-forming polymer (or mixture of polymers) with the active ingredient (and other disperse phase components) to form a dispersion in the polymer, which later in the process forms a hydrogel. The method normally comprises mixing together an aqueous polymer phase premix and a disperse phase premix. Taking account of the final formulation required (as described elsewhere herein), the disperse phase pre-mix and the liquid hydrogel-forming polymer (i.e. the solution or suspension of hydrogel-forming polymer) may be mixed in a weight ratio of from 1:1 to 1:10, particularly 1:4 to 1:9, e.g. 1:5 to 1:7. In general, only gentle stirring of the components is required using a magnetic or mechanical system, e.g. overhead stirrer, as would be familiar to a person skilled in the art to achieve a dispersion of the disperse phase in the aqueous phase to form a colloid (which may be in the form of for example an emulsion or micro emulsion in which the aqueous hydrogel is the continuous phase). Continuous stirring is preferred. Mixing may also be achieved using an in-line mixing system. Any appropriate laboratory stirring apparatus or industrial scale mixer may be utilized for this purpose for example the Magnetic Stirrer (manufactured by Stuart) or Overhead Stirrer (by KNF or Fisher). It is preferred to set up the equipment in such a way as to minimise evaporation of contents such as, for example, water. In one embodiment of the process of the invention, it is preferred to utilise a closed system for stirring in order to achieve this aim. In-line mixing may be particularly suitable for closed system processing. Suitably mixing of the two components takes place at a temperature of 50 to 70° C., or 55-75° C., e.g. 60-70° C.

The mixing of the two phases results in a colloid wherein the aqueous hydrogel-forming polymer is an aqueous continuous phase and the component(s) not soluble in the aqueous phase are a disperse phase. The colloid may have the form of an emulsion or microemulsion.

In embodiments where the disperse phase is or comprises a surfactant, the amount of the surfactant may be selected such that, upon combination of the disperse phase premix with the aqueous pre-mix, the surfactant concentration in the combined mixture exceeds the CMC for the surfactant used such that micelles are formed in the aqueous phase comprising the hydrogel-forming polymer. Depending on the concentration of surfactant used, self-assembly structures other than micelles may also form. The CMC for a particular surfactant may be determined using well known methods, for example as described in Surfactants and Polymers in Aqueous Solutions Second Edition, Chapter 2, Holmberg et al. In embodiments mixing of the aqueous phase and a disperse phase which is or comprises a surfactant may result in the formation of a clear liquid, for example a microemulsion, in which the aqueous phase comprising the hydrogel-forming polymer is the continuous phase. Microemulsions are a thermodynamically stable dispersion of self-assembly structures in the aqueous phase, the size of the self-assembly structures being sufficiently small to give a transparent appearance. The size of the self-assembly structures present as the disperse phase resulting from the mixing of the aqueous and surfactant phases may be from about 0.5 nm to 200 nm, for example about 1 nm to 50 nm, or about 5 nm to 25 nm. The size of the self-assembly structures formed and other characteristics such as the optical isotropicity of the formulation (for example a microemulsion) may be determined using well known techniques such as dynamic light scattering.

Where the polymer matrix substantially consists of gelatin with the addition of sorbitol, the aqueous phase of polymer matrix is prepared by adding the appropriate quantities of sorbitol (and surfactant if desired) to water, heating to approximately 50 to 75° C., for example 60-75° C. until in solution and then adding gelatin, although the precise order and timing of addition is not critical. A typical "gelatin solution" comprises 8 to 35%, (for example 15-25%, preferably 17-18%) gelatin; 65%-85% (preferably 77-82%) of water plus from 1-5% (preferably 1.5 to 3%) sorbitol. When present, surfactant (e.g. anionic surfactant) in the aqueous phase premix may be present in an amount of 0.1 to 5% (preferably 0.5 to 4%) wherein all parts are by weight of the aqueous phase.

Optionally the processing temperature required for a standard gelatin can be reduced to a desirable target temperature e.g. 37° C. by use of lower melting-point gelatin (or gelatin derivatives or mixtures of gelatins with melting point reducers) or other polymer matrix material such as, for example, sodium alginate. If gelatin droplets are being formed by machine extrusion and immediately cooled, e.g. in a cooling bath, additional appropriate inlet tubing can be used to introduce an oil phase containing cyclosporin A at ambient temperature into the hotter fluid gelatin solution (and the mixture can be immediately homogenized) very shortly before ejection from a beading nozzle or other droppleting process such that the duration of exposure of the cyclosporin A to the higher temperature gelatin is limited so reducing the degree of any heat-dependent degradation of the active ingredient. This process may use any appropriate device such as, for example, a homogenizer, e.g. a screw homogenizer, in conjunction with an extrusion-type apparatus as described for example in WO 2008/132707 (Sigmoid Pharma) the entirety of which is incorporated herein by reference.

The colloid is formed by combining of the disperse phase premix or particulate active ingredient with the liquid aqueous phase with stirring as described above. The resultant colloidal dispersion then has the formulation of a solidified core described above but with liquid water still present in the core formulation.

Optionally the active ingredient may be added after mixing the aqueous phase and other components of a disperse phase of the type comprising a vehicle in addition to the active ingredient, however, it is preferred that the active ingredient is added together with the other components of the disperse phase as a premix.

The resulting colloid is then poured or introduced into a mould or other vessel or poured onto sheets or between sheets or delivered dropwise (or extruded) into another fluid such that the polymer matrix-containing aqueous phase, on solidification, takes the form of the mould, vessel, sheet or droplet/bead intended. It is preferred to progress to mould-forming e.g. beading without delay.

Solidification (gelling) can occur in a variety of ways depending on the polymer of the matrix, for example by changing the temperature around the mould, vessel, sheet, droplet/bead etc or by applying a solidification fluid or hardening solution so that the moulded shape is gelled or solidified. In certain embodiments both temperature change and application of a solidifying fluid or hardening solution are employed together or simultaneously.

In the preferred embodiment in which the core comprising the active ingredient takes the form of beads, the beads may be formed for example by dropping the colloid dropwise into a fluid which effects solidification. Where the viscosity of the formulation to be beaded reaches a certain point, drop formation becomes more difficult and specialised apparatus is then preferred.

By use of the term "dry", it is not sought to imply that a drying step is necessary to produce the dry core (although this is not excluded) rather that the solid or solidified aqueous external phase is substantially free of water or free of available water. Solidification of the aqueous phase (external phase) may have arisen through various means including chemically (e.g. by cross-linking) or physically (e.g. by cooling or heating). In this respect, the term "aqueous phase" is nevertheless employed in this document to denote the external (continuous) phase of the core even though water, in certain embodiments, is largely absent from (or trapped within the cross-linked matrix of) the core. The external phase of the core is however water-soluble and dissolves in aqueous media.

In the case where solidification can be achieved by raising or reducing temperature, the temperature of the solidification fluid can be adapted to achieve solidification of the core at a desired rate. For example, when gelatin is used as the hydrogel-forming polymer, the solidification fluid is at a lower temperature than the temperature of the emulsion thus causing solidification, i.e. gelling, of the polymer matrix. In this case, the solidification fluid is termed a cooling fluid.

In the case where solidification can be achieved chemically, e.g. by induction of cross-linking on exposure to a component of the solidification fluid, the concentration of such component in the solidification fluid and/or its temperature (or other characteristic or content) can be adjusted to achieve the desired rate and degree of solidification. For example, if alginate is chosen as the polymer matrix, one component of the solidification fluid may be a calcium-containing entity (such as, for example, calcium chloride) able to induce cross-linking of the alginate and consequent solidification. Alternatively, the same or similar calcium-containing entity may be included (e.g. disperse) in the aqueous phase of the fluid emulsion prior to beading and triggered to induce cross-linking e.g. by applying a higher or lower pH to a solidification fluid into which droplets of emulsion fall dropwise or are introduced. Such electrostatic cross-linking can be varied as to the resulting characteristics of the bead by control of calcium ion availability (concentration) and other physical conditions (notably temperature). The solidification fluid may be a gas (for example air) or a liquid or both. For example, when gelatin is used as the hydrogel-forming polymer matrix, the solidification fluid can be initially gaseous (e.g. droplets passing through cooling air) and then subsequently liquid (e.g. droplets passing into a cooling liquid). The reverse sequence may also be applied while gaseous or liquid cooling fluids alone may also be used. Alternatively, the fluid may be spray-cooled in which the emulsion is sprayed into a cooling gas to effect solidification.

In the case of gelatin or other water-soluble polymer (or polymer mixture) destined to form an immobilization matrix, it is preferred that the solidification fluid be a non-aqueous liquid (such as, for example, medium chain triglycerides, mineral oil or similar preferably with low HLB to ensure minimal wetting) which can conveniently be placed in a bath (cooling bath) to receive the droplets of the colloid as they solidify to form the beads of the core. Use of a non-aqueous liquid allows greater flexibility in choice of the temperature at which cooling is conducted.

Where a liquid cooling bath is employed, it is generally maintained at less than 20° C., preferably maintained in the range 5-15° C., more preferably 8-12° C. when standard gelatin is used as the hydrogel-forming polymer. If a triglyceride is chosen as the cooling fluid in the cooling bath, a preferred example is Miglyol® 810 from Sasol.

If alginate is selected as the polymer matrix, a typical method of making beads involves dropwise addition of a 3% sodium alginate solution in which oil droplets are disperse as described above into a 4° C. crosslinking bath containing 0.1 M calcium chloride to produce calcium alginate (this method can be referred to as "diffusion setting" because the calcium is believed to diffuse into the beads to effect cross-linking or setting). Using a syringe pump, or Inotech machine, droplets can be generated or extruded (egg at 5 mL/h if a pump is used) through a sterile needle or other nozzle (described elsewhere herein) which can be vibrating as discussed elsewhere herein. Airflow of between 15 and 20 L/min through 4.5 mm tubing can be applied downwards over the needle to reduce droplet size if desired. Newly formed beads can then be stirred in the calcium chloride bath for up to an hour. If carrageenan is used as the polymer matrix both salt and reduction in temperature e.g. by dropping into cooling oil may be used to obtain solidification.

An alternative approach when using alginate is internal gelation in which the calcium ions are disperse in the aqueous phase prior to their activation in order to cause gelation of hydrocolloid particles. For example, this can be achieved by the addition of an inactive form of the ion that will cause crosslinking of the alginate, which is then activated by a change in e.g. pH after sufficient dispersion of the ion is complete (see Glicksman, 1983a; Hoefler, 2004 which are both incorporated herein by reference). This approach is particularly useful where rapid gelation is desired and/or where the diffusion approach may lead to loss of API by diffusion thereof into the crosslinking bath.

Where another ionotropic polymer is used than alginate, suitable analogous processes may be used to those described herein in relation to alginate.

Following shape-forming, moulding or beading, the resultant shapes or forms may be washed then dried if appropriate. In the case of beads solidified in a solidification fluid, an optional final step in the method of production described above therefore comprises removal of the solidified beads from the solidification fluid. This may be achieved e.g. by collection in a mesh basket through which the solidification fluid (e.g. medium chain triglycerides) is drained and the beads retained and is preferably conducted without delay e.g. as soon as the beads have formed or within 5, 10, 15, 20, 25 or 30 minutes of their formation. Excess solidification fluid may then be removed using a centrifuge (or other apparatus or machine adapted to remove excess fluid) followed by drying of the beads to remove water or free water and/or removal of some or all of any additional solvent e.g. ethanol or isopropyl alcohol used to dissolve or facilitate dissolution of the active principle in preceding steps optionally followed by washing (e.g. using ethyl acetate) and a subsequent "drying" step to remove excess solvent (e.g. ethyl acetate). Isopropyl alcohol is an example of a solvent which is preferably removed later in processing to reduce residues in the oil or aqueous phase. Drying can be achieved by any suitable process known in the art such as use of a drum drier (e.g. Freund Drum dryer which may be part of the Spherex equipment train if used) with warm air at between 15° C. and 25° C., preferably around 20° C. leading to evaporation or entrainment of the water by the air. Alternatively, drying may be carried out using of a fluid bed drier (e.g. Glatt GPCG 1.1) with warm air between 40° C. and 60° C. Use of gelatin as the polymer matrix (e.g. as principal constituent of the aqueous immobilisation phase) in most cases requires a drying step and for beads this is preferably achieved by drying in air as above described. The resultant formulation (the formulation of the invention) is essentially dry as described in more detail above.

In general, the beads may be generated by the application of surface tension between the liquid dispersion (the mixture of the aqueous and surfactant phases) and an appropriate solidification fluid such as, for example, gas or liquid in order to create the spherical or substantially spherical shape of the ultimate beads.

Alternatively, the beads may be produced through ejection or extrusion of the liquid dispersion through an orifice or nozzle with a certain diameter and optionally subject to vibration (using selected vibrational frequencies) and/or gravitational flow. Examples of machines which may be used are encapsulation prilling, drop pelletising, spray cooling or spray congealing machines for example the Freund Spherex, ITAS/Lambo, Globex, Inotech, GEA Niro, Droppo, Buchi, Gelpell processing equipment processing equipment. Operation of the Spherex machine manufactured by Freund as may be desired to manufacture beads according to the present invention is described in U.S. Pat. No. 5,882,680 (Freund), the entire contents of which are incorporated herein by reference. It is preferred to select a vibrational frequency in the region of 2-200 Hz, suitably 10-15 Hz, although the ultimate choice (and separately the amplitude of vibration selected) depends on the viscosity of the dispersion to be beaded. If the polymer matrix is chosen to solidify at lower temperature, it may be appropriate to maintain the lines to the orifice/nozzle at a certain temperature to maintain the fluidity of the solution. Suitably the colloid is ejected through a single-orifice nozzle, e.g. having a diameter of from 0.1 mm to 5 mm (for example 0.5-5 mm), to form drops which are then caused or allowed to fall into a cooling oil or other hardening medium and allowed to harden to form seeds, after which the seeds are recovered from the cooling oil and dried.

It will be appreciated, therefore, that the invention includes a process for manufacturing a core comprising a pharmaceutically active ingredient in a polymer matrix, which process comprises: forming an aqueous premix which comprises water and water soluble/dispersible materials (including therefore a hydrogel-forming polymer) and a disperse phase premix (e.g. an oil phase premix) which comprises the active ingredient and optionally a vehicle and other excipients (e.g. oil(s) and oil soluble/dispersible materials), and combining the two premixes to form a colloid (disperse phase) within an aqueous phase comprising the hydrogel-forming polymer. The colloid may then be formed into a shaped unit, for example a bead to provide the core comprising the active ingredient. More particularly the manufacture of a core comprising pharmaceutically active ingredient and a polymer matrix (suitably a hydrogel-forming polymer matrix may comprise:

(i) forming an aqueous phase pre-mix comprising a solution in water of water-soluble constituents (e.g. of a hydrogel-forming polymer, any water-soluble excipient(s), as described elsewhere herein);

(ii) forming a disperse phase pre-mix typically comprising a dispersion or preferably a solution of an active ingredient, e.g. cyclosporin A, in a liquid, optionally where the liquid is an oil (and optionally together with other disperse phase constituents (e.g. surfactant, solvents etc as described elsewhere herein));

(iii) mixing the aqueous phase pre-mix (i) and the disperse phase pre-mix (ii) to form a colloid;

(iv) ejecting the colloid through a nozzle to form droplets;

(v) causing or allowing the a hydrogel-forming polymer to gel or solidify to form a water soluble polymer matrix; and (vi) drying the solid.

Some manufacturing processes comprise steps (A) to (D) below or, alternatively, a manufacturing process may comprise a single one or any combination of steps (A) to (D).

(A) Exemplary Preparation of Aqueous Phase:

Aqueous phase components are added to water, e.g. purified water, under agitation e.g. sonication or stirring. The temperature is gradually increased, for example to 60-70° C. and in particular 65° C., to achieve complete dissolution of the solids. The aqueous phase components include a hydrogel-forming polymer, e.g. gelatin or agar and optionally one or more other excipients, for example D-sorbitol (a plasticiser) and surfactant (for example SDS). Possible aqueous phase components are described elsewhere herein.

The gelatin may be Type A gelatin. In some less preferred implementations, the gelatin is Type B. The gelatin may have a Bloom strength of 125-300, optionally of 200-300, for example of 250-300, and in particular 275. The components of the aqueous phase may be agitated for a period of, for example, from 1 hour to 12 hours to complete preparation of the aqueous phase (aqueous premix).

(B) Exemplary Preparation of Disperse Phase:

A hydrophobic active ingredient, e.g. cyclosporin A, is mixed with other disperse phase components (for example an oil, surfactant and co-solvent) under agitation e.g. sonication or stirring, suitably at ambient temperature to disperse or preferably dissolve the active ingredient.

(C) Exemplary Mixing of the Two Phases

The aqueous phase and the disperse phase are mixed. The two phases may be mixed in a desired weight; for example, the weight ratio of disperse phase to aqueous phase may be from 1:1 to 1:10, e.g. from 1:4 to 1:9 and optionally from 1:5 to 1:8 such as about 1:5 or about 1:7. The resulting colloid is agitated, e.g. sonicated or stirred, at a temperature of 60-70° C. and in particular 65° C., to achieve a homogeneous dispersion, then the homogenous dispersion is formed into beads. In particular, the homogenous dispersion is ejected through a single orifice nozzle to form droplets which fall into a cooling medium. The nozzle is suitably vibrated to facilitate droplet formation. The nozzle may be vibrated at a frequency of 2-200 Hz and optionally 15-50 Hz.

The cooling medium may for example be air or an oil; the oil is suitably physiologically acceptable as, for example, in the case of medium chain triglycerides e.g. Miglyol® 810N. The cooling medium may be at a cooling temperature often of less than 15° C., for example of less than 10° C. but above 0° C. In some embodiments the cooling temperature is 8-10° C. The nozzle size (diameter) is typically from 0.5 to 7.5 mm, e g from 0.5 to 5 mm and optionally from 0.5 to 4 mm. In some embodiments, the nozzle diameter is from 1 to 5 mm for example from 2 to 5 mm, and optionally from 3 to 4 mm, and in particular may be 3.4 mm.

The flow rate through a 3.4 mm nozzle is 5 to 35 g/min and optionally 10 to 20 g/min and for nozzles of different sizes may be adjusted suitably for the nozzle area.

(D) Exemplary Processing of Beads

Cooled beads are recovered, for example they may be recovered from cooling oil after a residence time of 15-60 minutes, for example after approximately 30 minutes. Beads recovered from a cooling liquid (e.g. oil) may be centrifuged to eliminate excess cooling liquid, and then dried. Suitably, drying is carried out at room temperature, for example from 15-25° C. and optionally from 20-25° C. The drying may be performed in a drum drier, for example for a period from 6 to 24 hours, e.g. of about 12 hours in the case of beads dried at room temperature. The dried beads may be washed, suitably with a volatile non-aqueous liquid at least partially miscible with water, e.g. they may be washed with ethyl acetate. The washed beads may be dried at room temperature, for example from 15-25° C. and optionally from 20-25°

C. The drying may be performed in a drum drier, for example for a period from 6 to 48 hours, e.g. of about 24 hours in the case of beads dried at room temperature. Drying may be achieved by any suitable means, for example using a drum dryer, suitably under vacuum; or by simply passing warm air through the batch of beads, or by fluidising the beads in a suitable equipment with warm air, for example if a fluid bed dryer. Following drying, the beads are passed through a 1 to 10 mm, optionally 2 to 5 mm to remove oversized beads and then through a sieve with a pore size of 0.5 to 9 mm optionally 1 to 4 mm to remove undersized beads.

It can be appreciated that it is possible to recycle the beads that are rejected by the sieving process.

As a further aspect of the invention there is provided a formulation obtainable by (having the characteristic of) any of the processes described herein. It is to be understood that the processes described herein may therefore be used to provide any of the specific cores described in embodiments herein by dispersing the appropriate components which form the disperse phase of the core in the appropriate components which form the aqueous continuous matrix phase of the core.

The preceding paragraphs describe the formation of uncoated cores comprising a pharmaceutically active ingredient in for example a hydrogel-forming polymer matrix. The cores are suitably coated to provide the formulation according to the invention. The cores may be first coated with a subcoat and and then further coated with a second coating (also referred to as a modified release coating). Suitable sub coats and modified release coatings are any of those described herein and any of the first coating (for the subcoat) or the second coating (for the modified release coating). The coating(s) may be applied using well known methods, for example spray coating as described below to give the desired sub coat and modified release coating weight gains.

With regard to one of the methods described above (ejection of emulsion through an optionally vibrating nozzle) with two concentric orifices (centre and outer), the outer fluid may form a coating (outside the bead) as described herein. The Spherex machine manufactured by Freund (see U.S. Pat. No. 5,882,680 to Freund) is preferably used (the entire contents of this patent is incorporated herein by reference). Other similar ejection or extrusion apparatus may also be used, for example the ejection apparatus described hereinbefore.

Use of the Spherex machine achieves very high monodispersity. For example, in a typical 100 g, batch 97 g of beads were between 1.4 to 2 mm diameter or between 1 and 2 mm. Desired size ranges can be achieved by methods known in the art for rejecting/screening different sized particles. For example, it is possible to reject/screen out the larger/smaller beads by passing a batch first through e.g. a 2 mm mesh and subsequently through a 1.4 mm mesh.

The 1.4 to 2 mm diameter range is a good size if it is desired to spray coat the beads (if smaller, the spray of the coating machine may bypass the bead; if too large, the beads may be harder to fluidise, which is necessary to achieve consistent coating).

Coating Process

The coating process can be carried out by any suitable means such as, for example, by use of a coating machine which applies a solution of a polymer coat (as described above in particular) to the formulation. Polymers for coating are either provided by the manufacturer in ready-made solutions for direct use or can be made up before use following manufacturers' instructions.

Coating is suitably carried out using a fluid bed coating system such as a Wurster column to apply the coating(s) to the cores. Appropriate coating machines are known to persons skilled in the art and include, for example, a perforated pan or fluidized-based system for example the GLATT, Vector (e.g. CF 360 EX), ACCELACOTA, Diosna, O'Hara and/or HICOATER processing equipment. To be mentioned is the MFL/01 Fluid Bed Coater (Freund) used in the "Bottom Spray" configuration.

Typical coating conditions are as follows:

| Process Parameter | Values |
| --- | --- |
| Fluidising airflow (m3/h) | 20-60 (preferably 30-60) |
| Inlet air temperature (° C.) | 20-65 |
| Exhaust air temperature (° C.) | 20-42 |
| Product temperature (° C.) | 20-45 (preferably 40 to 42) |
| Atomizing air pressure (bar) | Up to 1.4 e.g. 0.8-1.2 |
| Spray rate (g/min) | 2-10 and 3-25 RPM |

Suitably the coating is applied as a solution or dispersion of the polymers (and other components) of the coating. Generally the coatings are applied as an aqueous, solution of dispersion, although other solvent systems may be used if required. The coating dispersion is applied to the cored as a spray in the fluid bed coater to give the required coating weight gain. Generally the coating process is carried out at a temperature which maintains the cores at a temperature of from 35 to 45° C., preferably 40 to 42° C.

After applying the coating, the formulation may be dried, for example by drying at 40 to 45° C.

The invention further provides a product having the characteristics of a formulation obtained as described herein, a product defined in terms of its characteristics being defined by the characteristics of the formulation to the exclusion of the method by which it was made.

As mentioned herein the processes described may be used to provide any of the formulations described in the various embodiments herein. By way of example there is provided a formulation of the invention comprising a core and a coating comprising a water-soluble cellulose ether or a water soluble derivative of a cellulose ether wherein the core comprises a hydrogel-forming polymer matrix comprising gelatin, cyclosporin A or another hydrophobic active ingredient, medium chain mono-di- and/or tri-glycerides, a co-solvent and surfactant, the core having the characteristics of a core obtained by the process comprising steps (i) to (vi) described above for forming the core, wherein the aqueous phase pre-mix in step (i) of the process comprises gelatin and surfactant (suitably an anionic surfactant), and the oil phase pre-mix in step (ii) of the process comprises medium chain mono-di- or tri-glycerides, hydrophobic active ingredient, surfactant (suitably a non-ionic surfactant) and cosolvent; and the wherein the core is optionally coated with a coating comprising a water-soluble cellulose ether or a water soluble derivative of a cellulose ether and the thus-coated core is optionally coated with a second coating; wherein the coatings are any of those described herein. Accordingly, the process may produce a formulation as described above comprising a first coating. The process may additionally produce a formulation comprising a first coating and a second coating being outside the first coating.

In addition the process to form a formulation of the invention may comprise the steps of mixing a first population and a second population, wherein the first population has a coating that is or comprises a water-soluble cellulose ether but having no outer coating, e.g. as described herein; and the second population has a first coating that is or comprises a water-soluble cellulose ether and a second coating that is or comprises a delayed release coating, for example as described herein e.g. a coating that is or comprises a delayed release polymer.

In the cores described herein to which the following characteristics are applicable, e.g. in the immediately preceding paragraph, the following characteristics may be present:

gelatin may be present in an amount of in an amount of 300 to 700 mg/g;

the medium chain mono-, di- or tri-glycerides (for example caprylic/capric triglyceride) may be present in an amount of 20 to 200 mg/g;

co-solvent (for example 2-(ethoxyethoxy)ethanol) may be present in an amount of 150 to 250 mg/g;

non-ionic surfactant (for example sorbitan-based surfactants, PEG-fatty acids, or glyceryl fatty acids or poloxamers or particularly a polyethoxylated castor oil for example Kolliphor® EL) may be present in an amount of 80 to 200 mg/g;

anionic surfactant (for example, alkyl sulphates, carboxylates or phospholipids (particularly SDS)) may be present in an amount of 15 to 50 mg/g; and active ingredient, particularly cyclosporin A, may be present in an amount of from 60 to 180 mg/g, suitably 60 to 150 mg/g or 80 to 100 mg/g, for example 81 to 98 mg/g; wherein all weights are based upon the dry weight of the core before coating.

The core is coated with a first coating (sub-coating) which is or comprises a water-soluble compound selected from cellulose ethers and their derivatives, particularly hydroxypropylmethyl cellulose; the first coating being present in an amount corresponding to a weight gain due to the first coating in a range selected from: (i) from 8% to 12%, for example about 10%; or (ii) from 4% to 6%, for example about 5% by weight based upon the weight of the core prior to applying the first coating. The first coating may have a modified release coating (or second coating) applied to it.

Preferably, any modified release coating, especially in the embodiments of the immediately preceding paragraphs, is or comprises a pH independent modified release coating, more especially the second coating may be a modified release coating comprising ethyl cellulose (eg Surelease®) still more particularly a modified release coating comprising ethyl cellulose and a water-soluble polysaccharide, pectin (e.g. a Surelease®-pectin coating as described herein); and wherein the modified release coating is present in an amount corresponding to a weight gain of the formulation due to the second coating selected from (a) from 10% to 12%, for example about 11% or about 11.5%; or (b) from 16% to 18%, for example about 17% by weight based upon the weight of the formulation prior to applying the second coating.

Applications

The formulations of the invention may advantageously be used for oral delivery pharmaceutically active ingredients by virtue of the enhanced dissolution profiles achieved.

The formulations of the invention include modified release formulations which comprise cyclosporin A as an active ingredient and a modified release coating, for example comprising a pH independent polymer, to target cyclosporin release to the lower intestine. Such formulations result in low systemic exposure to cyclosporin A, whilst providing high levels of cyclosporin A in the lower GI tract, particularly in the colon. Such formulations release the cyclosporin A in an active form for example as a solution, which provides enhanced absorption of cyclosporin A in the local tissue of the lower GI tract. When the formulation is used in the form of minibeads, the minibeads are advantageously dispersed along large sections of the GI tract following oral administration and are therefore expected provide a more uniform exposure to cyclosporin to large sections of for example the colon. Needless to say, the invention includes such formulations in which the cyclosporin A is replaced by, or supplemented by, another active ingredient for local treatment of the lower GI tract, e.g. colon. The other active ingredient may be another immunosuppressant or a hydroxylase inhibitor, e.g. DMOG or hydralazine, or it may be a combination of active ingredients comprising at least one mentioned in this sentence. Tacrolimus and sirolimus are examples of other immunosuppressants.

Accordingly the modified release formulations according to the invention comprising an active ingredient for local treatment of the lower GI tract are expected to be useful in the treatment or prevention of a condition of the GIT. In particular the formulation of the invention may comprise cyclosporin A and/or another immunosuppressant and be useful in the prevention or treatment of inflammatory conditions affecting the lower GI tract, particularly conditions affecting the colon.

The formulation of the invention is administered orally. The dose required will vary depending upon the specific condition being treated and the stage of the condition. In the case of formulations containing cyclosporin A, the formulation will generally be administered to provide a dose of cyclosporin A of from 0.1 to 100 mg, for example a dose of 1 to 500 mg or particularly a dose of 25 to 250 mg cyclosporin A. The formulation is suitably administered as a single daily dose.

In one aspect of the invention there is provided a formulation of the invention that comprises an immunosuppressant as active ingredient and is for use in the treatment or prophylaxis of an inflammatory bowel disease, Crohn's disease, ulcerative colitis, graft-versus-host disease, gastrointestinal graft-versus-host disease, myasthenia gravis, irritable bowel syndrome (e.g. with constipation, diarrhea and/or pain symptoms), celiac disease, stomach ulcers, diverticulitis, pouchitis, proctitis, mucositis, radiation-associated enteritis, short bowel disease, or chronic diarrhea, gastroenteritis, duodenitis, jejunitis, peptic ulcer, Curling's ulcer, appendicitis, colitis, diverticulosis, endometriosis, colorectal carcinoma, adenocarcinoma, inflammatory disorders such as diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, interdeminate colitis, jejunoiletis, ileitis, ileocolitis or granulomatous colitis, the prevention of rejection following bone marrow transplantation, psoriasis, atopic dermatitis, rheumatoid arthritis or nephrotic syndrome.

In one embodiment the formulation of the invention that comprises an immunosuppressant as active ingredient is for use in the treatment of an inflammatory bowel disease. The main forms of inflammatory bowel disease are Crohn's disease and ulcerative colitis. Accordingly the formulation of the invention may be useful in the treatment of both of these conditions.

Crohn's disease may affect the entire GI tract including the colon. However, ulcerative colitis is a condition which affects only the colon and the rectum. Accordingly, the release profile provided by the colon-targeted, immunosuppressant-containing (e.g. cyclosporin A-containing), formulation according to the invention is expected to be especially beneficial in the treatment of ulcerative colitis.

The colon-targeted, immunosuppressant-containing formulation of the invention primarily releases immunosuppressant, e.g. cyclosporin A, in the colon. However, drug may also be released higher in the GI tract and accordingly the formulation may also provide therapeutic benefit in conditions which affect other parts of the lower GI tract.

Gastrointestinal Graft-Versus-Host-Disease (GI-GVHD) is a life-threatening condition and one of the most common causes for bone marrow and stem cell transplant failure. In patients with GI-GVHD it is the donor cells that begin to attack the patient's body—most frequently the gut, liver and skin. Patients with mild-to-moderate GI-GVHD typically develop symptoms of anorexia, nausea, vomiting and diarrhoea. If left untreated, GI-GVHD can progress to ulcerations in the lining of the GI tract, and in its most severe form, can be fatal. Accordingly, in one embodiment the immunosuppressant-containing formulation is for use in the treatment or prophylaxis of Gastrointestinal Graft-Versus-Host-Disease (GI-GVHD).

In a further embodiment there is provided an immunosuppressant-containing formulation of the invention for use in the treatment of celiac disease.

The coating containing the water-soluble cellulose ether of the present invention may be useful in reducing the variability between release profiles of different batches of minibeads. The first coating being beneath the second coating has been shown (see FIG. 10) to produce beads with similar (±5% release) % release of the active ingredient at time points in a release profile. This has the beneficial effect of improving consistency in in-vitro release profiles but also in in-vivo dissolution and consequently consistent release of the active along the gastrointestinal tract.

A "batch" is a specific quantity of a drug or other material that is intended to have uniform character and quality, within specified limits, and is produced according to a single manufacturing order during the same cycle of manufacture. A "lot" means a batch, or a specific identified portion of a batch, having uniform character and quality within specified limits; or, in the case of a drug product produced by continuous process, it is a specific identified amount produced in a unit of time or quantity in a manner that assures its having uniform character and quality within specified limits. "Lot number", "control number", or "batch number" means any distinctive combination of letters, numbers, or symbols, or any combination of them, from which the complete history of the manufacture, processing, packing, holding, and distribution of a batch or lot of drug product or other material can be determined."

EXAMPLES

Example 1: Preparation of a Minibead with a Hydroxypropyl Methylcellulose Coating The minibead was generally prepared by forming a core according to the following procedure and then coating the core with a dispersion of Opadry® White 20A28380 (supplied by Colorcon).
Core Manufacture
The cores in the form of seamless minibeads were prepared using Spherex process as follows.

An aqueous phase was prepared by mixing sodium dodecyl sulphate (SDS) and D-sorbitol with purified water under constant stirring. Gelatin was then added to this solution and gentle heat was applied to approximately 60-70° C. to achieve complete melting of gelatin.

An oil phase was prepared by mixing together 2-(2-ethoxyethoxy)ethanol (Transcutol HP), polyethoxylated castor oil (Kolliphor® EL) and capric/caprylic triglyceride (Miglyol® 810) with stirring at room temperature to form a solution. Ciclosporin A was added and mixed until a clear solution was obtained. The oil phase was mixed with the heated aqueous phase in a ratio of approximately 1:7 (oil phase:aqueous phase). The resulting mixture was stirred at 60-70° C. to achieve homogeneity.

The resulting mixture was then fed (via temperature controlled tubing) through a vibrating nozzle, with a single nozzle outlet with a diameter of 3 mm. Seamless minibeads were formed as the solution flowed through the vibrating nozzle into a cooling chamber of constantly flowing medium chain triglyceride (Miglyol® 810) cooling oil at a temperature of 10° C.

The minibeads were removed from the cooling oil and placed in a centrifuge to remove the excess oil. Following centrifugation, a first drying step was initiated with a set refrigerator temperature of 10° C. and the heater temperature of 20° C. The dryer was rotated at 15 RPM. When the beads were observed to be freely rotating in the drying drum, they were considered to be dry.

The minibeads were washed with ethyl acetate and then dried for a further 24 h under the same drying conditions as those mentioned above in the first drying step. The dried minibeads were then sieved to remove oversize and undersize beads resulting in cores 1 mm-2 mm in diameter. This procedure provided cores with the composition shown in Table 1, the values being the weight percent of the total weight for each component.

TABLE 1

| Component | w/w % |
| --- | --- |
| Cyclosporin A | 10.8 |
| Miglyol ® 810 N | 4.6 |
| Transcutol HP | 16.4 |
| Kolliphor ® EL | 9.2 |
| SDS | 4.0 |
| Sorbitol | 5.7 |
| Gelatin | 49.3 |

Coating the Core
The minibead cores were loaded into a fluid bed coater (Wurster column) and coated with Opadry® White 20A28380 (supplied by Colorcon Limited) as a dispersion. The processing parameters, such as inlet air temperature and inlet air volume, were adjusted to keep the minibead temperature between 40° C. and 42° C. until the required coating weight gain was reached. The resulting subcoated minibeads were dried for 5 minutes at 40° C. in the coater.
Composition of the Minibead
A minibead with the composition shown in Table 2 below was produced by the above procedure. The minibead has an Opadry® weight gain of 2.7% relative to the weight of the core.

TABLE 2

| Component | w/w % |
| --- | --- |
| Cyclosporin A | 10.5 |
| Miglyol ® 810 N | 4.5 |

TABLE 2-continued

| Component | w/w % |
| --- | --- |
| Transcutol HP | 16.0 |
| Kolliphor ® EL | 9.0 |
| SDS | 3.9 |
| Sorbitol | 5.5 |
| Gelatin | 48.0 |
| Opadry ® | 2.6 |

Example 2: Preparation of Minibeads with a Hydroxypropyl Methylcellulose Coating Following the procedure described in Example 1, minibeads coated with hydroxypropyl methylcellulose with the differing % weight gains of Opadry® were produced. The % weight gain of Opadry® are shown in Table 3 below.

TABLE 3

|  | % weight gain of Opadry ® |
| --- | --- |
| Example 2a | 6.3% |
| Example 2b | 10% |
| Example 2c | 15% |

The minibeads of Examples 2a-c had the composition shown in Table 4.

TABLE 4

| Component | Example 2a | Example 2b w/w % | Example 2c |
| --- | --- | --- | --- |
| Cyclosporin A | 10.2 | 9.8 | 9.4 |
| Miglyol ® 810 N | 4.3 | 4.2 | 4.0 |
| Transcutol HP | 15.5 | 14.9 | 14.3 |
| Kolliphor ® EL | 8.7 | 8.4 | 8.0 |
| SDS | 3.8 | 3.6 | 3.5 |
| Sorbitol | 5.3 | 5.2 | 5.0 |
| Gelatin | 46.3 | 44.8 | 42.8 |
| Opadry ® | 5.9 | 9.1 | 13.0 |

Example 3: In-Vitro Dissolution Profile of Minibeads of Examples 1, 2a, 2b and 2c Up to 4 Hours The in-vitro dissolution profiles of a sample of the minibeads produced in Examples 1, 2a, 2b and 2c were measured in water. As a reference example, the dissolution profile of the core with no Opadry® coating produced in Example 1 was tested. The dissolution testing was carried out in accordance with USP <711> Dissolution using Apparatus II (paddle apparatus) operated with a paddle speed of 75 rpm and with the dissolution medium at a temperature of 37° C.±5° C.

Aliquots of the medium were taken for analysis at 1 hour, 2 hours and 4 hours for all of the test media. In addition to these time points, aliquots were also taken at the following time points for the indicated minibeads:
 minibeads of Examples 1 and 2a—20 mins, 40 mins and 1.5 hours;
 minibeads of Examples 2b, 2c and the non-coated core of Example 1—30 mins.
The aliquots were analysed for cyclosporin A using Reverse Phase HPLC with UV detection at 210 nm.

The amount of dissolved cyclosporin A in the dissolution medium is expressed as a percentage based upon the original cyclosporin content in the test formulation (the % released). The % release values provide a release profile when plotted against time and the release profile for each of the samples of minibeads from Examples 1, 2a, 2b, 2c and the non-coated core of Example 1 is shown in FIG. 1.

The release profiles of the tested minibeads clearly show that an additional subcoat of hydroxypropyl methylcellulose (Opadry®) enhances the dissolution of the active ingredient within the first 2 hours of the dissolution test. All of the minibeads with a coating of hydroxypropyl methylcellulose (HPMC) released cyclosporine into solution much more rapidly than the non-coated core of Example 1. This is surprising and counterintuitive. Common sense suggests that adding additional material onto the core, which coating the core with HPMC does, should increase the time in which it takes to release the active into solution.

Example 4: In-Vitro Dissolution Profile of Minibeads of Examples 1, 2a, 2b and 2c Up to 24 Hours Following the same protocol as that described in Example 3 a dissolution profile of minibeads of Examples 1, 2a, 2b, 2c and the non-coated core of Example 1 over 24 hours was generated.

In addition to the aliquot samples taken at the time points mentioned in Example 3 each of the dissolution tests were also sampled at 6 hours, 12 hours, 18 hours and 24 hours. Every sample taken from the dissolution tests were analysed for cyclosporin A using Reverse Phase HPLC with UV detection at 210 nm.

Figure 2:
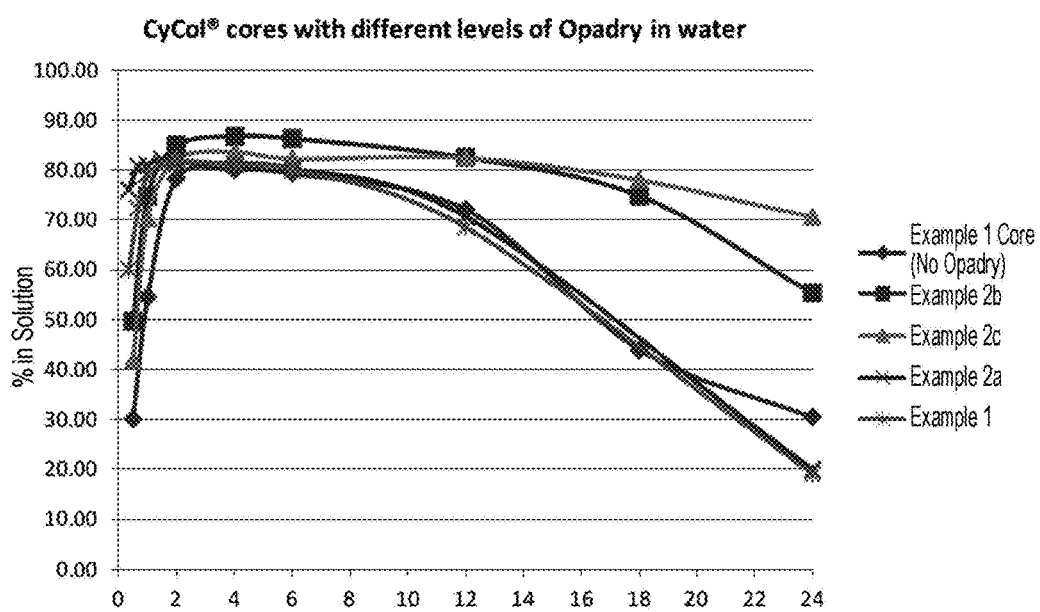
FIG. 2 is a graph plotting % of cyclosporin in solution against time over 24 hours and showing the release profiles of minibeads of Example 1 and Examples 2a-c with differing levels of a coating comprising hydroxypropyl methylcellulose compared to the release profile of a core of Example 1 which does not have a hydroxypropyl methylcellulose coating.

As in Example 3 a graph of the release profile of each dissolution test was generated and the release profiles are shown in FIG. 2.

It is evident from the release profiles of FIG. 2 that the presence of a HPMC coating significantly improves the cyclosporin release when compared to a non-coated core. Not only is there a more rapid release of the cyclosporin within the first 2 hours but the presence of a HPMC coating also maintains the cyclosporin in solution in the water dissolution medium.

Example 5: Preparation of a Minibead with a First Coating of Hydroxypropyl Methylcellulose and a Second Coating of Ethylcellulose/Pectin A core was produced and subsequently coated with Opadry®, the first coating (also referred to as a subcoat), following the procedure in Example 1. The minibead produced by the procedure of Example 1 was then further coated with a second coating (also referred to as an overcoat) of a mixture of Surelease® (an ethylcellulose dispersion) and Pectin.

The Surelease®/pectin overcoat was applied by the following procedure. Pectin was added to purified water in a stainless steel vessel and mixed to obtain a solution. Surelease® was slowly added to the vessel whilst maintaining mixing to provide the required Pectin concentration in the Surelease® for the overcoat. The resulting coating suspension was then applied onto the surface of the sub-coated minibeads using an analogous coating method to that described for the Opadry® coating in Example 1 until the desired weight gain of Surelease®/Pectin was reached. The over-coated minibeads were then dried in the coater for an hour at 40-45° C.

A number of minibeads with differing levels of Opadry® and differing levels of Surelease®/Pectin were produced.

Table 5 shows the % weight gain of Opadry® and the % weight gain of Surelease®/Pectin of the minibeads that were produced.

TABLE 5

|  | % weight gain of Opadry ® | % weight gain of Surelease ®/Pectin |
|---|---|---|
| Example 5a | N/A | 9% |
| Example 5b | 2.7% | 11% |
| Example 5c | 6.3% | 11% |
| Example 5d | 10% | 11% |
| Example 5e | N/A | 5% |
| Example 5f | 2.6% | 4.6% |
| Example 5g | 11.9% | 5.4% |
| Example 5h | N/A | 21.3% |
| Example 5i | 10.6% | 23.3% |
| Example 5j | 15.5% | 23.1% |

Examples 5a, 5e and 5h have no Opadry® coating. They are produced by coating a core described in Example 1 with Surelease®/Pectin as described above.

The minibeads of Examples 5a-j have the compositions shown in Table 6.

TABLE 6

| Component | Example 5a | Example 5d | Example 5c | Example 5b | Example 5h | Example 5i | Example 5j |
|---|---|---|---|---|---|---|---|
| | | | | w/w % | | | |
| Cyclosporin A | 9.9 | 8.8 | 9.2 | 9.5 | 8.9 | 7.9 | 7.6 |
| Miglyol ® 810 N | 4.2 | 3.8 | 3.9 | 4.0 | 3.8 | 3.4 | 3.2 |
| Transcutol HP | 15.1 | 13.4 | 13.9 | 14.4 | 13.5 | 12.0 | 11.5 |
| Kolliphor ® EL | 8.4 | 7.6 | 7.8 | 8.1 | 7.6 | 6.8 | 6.5 |
| SDS | 3.7 | 3.3 | 3.4 | 3.5 | 3.3 | 3.0 | 2.8 |
| Sorbitol | 5.2 | 4.7 | 4.8 | 5.0 | 4.7 | 4.2 | 4.0 |
| Gelatin | 45.2 | 40.3 | 41.8 | 43.2 | 40.6 | 36.1 | 34.6 |
| Opadry ® | N/A | 8.2 | 5.3 | 2.4 | N/A | 7.8 | 10.9 |
| Surelease ® (solid contents) | 8.1 | 9.7 | 9.7 | 9.7 | 17.2 | 18.4 | 18.5 |
| Pectin | 0.2 | 0.2 | 0.2 | 0.2 | 0.4 | 0.4 | 0.4 |

| Component | Example 5e | Example 5f | Example 5g |
|---|---|---|---|
| | | w/w % | |
| Cyclosporin A | 10.3 | 10.1 | 9.2 |
| Miglyol ® 810 N | 4.4 | 4.3 | 3.9 |
| Transcutol HP | 15.6 | 15.3 | 13.9 |
| Kolliphor ® EL | 8.8 | 8.6 | 7.8 |
| SDS | 3.8 | 3.7 | 3.4 |
| Sorbitol | 5.4 | 5.3 | 4.8 |
| Gelatin | 46.9 | 45.9 | 41.8 |
| Opadry ® | N/A | 2.4 | 10.1 |
| Surelease ® (solid contents) | 4.7 | 4.3 | 5.0 |
| Pectin | 0.1 | 0.1 | 0.1 |

Example 6: In-Vitro Dissolution Profile of Minibeads of Examples 5a-d

The in-vitro dissolution profiles of a sample of the minibeads produced in Examples 5a-d were measured using the following two stage dissolution test. The dissolution testing was carried out in accordance with USP <711> Dissolution using Apparatus II (paddle apparatus) operated with a paddle speed of 75 rpm and with the dissolution medium at a temperature of 37° C.±0.5° C. In the first stage of the test the dissolution medium was 750 ml of 0.1N HCl simulating the pH of the gastric environment. At the start of the test (t=0) the sample was placed in the dissolution medium. After 2 hours an aliquot of the medium is taken for subsequent analysis and immediately (suitably within 5 minutes) the second stage of the dissolution test is initiated. In the second stage 250 ml of 0.2M tribasic sodium phosphate containing 2% sodium dodecyl sulphate (SDS) is added to the dissolution medium and the pH adjusted to 6.8±0.05 using 2N NaOH or 2N HCl as required.

Samples of the dissolution medium were taken at the following time points during the second stage of the test: 4 hours; 6 hours; 12 hours; and 24 hours from the start of the test (i.e. from t=0 at the start of the first stage).

The sample taken at the end of the first stage (2 hours) and the samples from the second stage were analysed for cyclosporin A using Reverse Phase HPLC with UV detection at 210 nm.

The amount of dissolved cyclosporin A in the dissolution medium is expressed as a percentage based upon the original cyclosporin content in the test formulation (the % released). The % release values provide a release profile when plotted against time and the release profile for each of the samples of minibeads from Examples 5a-d are shown in FIG. 3.

Figure 3:
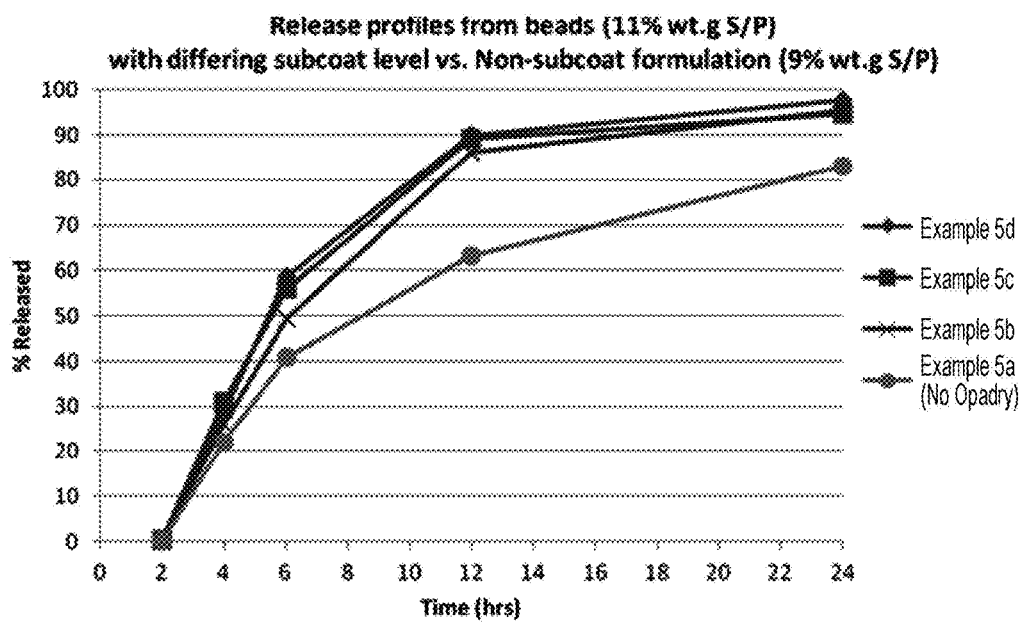
FIG. 3 is a graph plotting % of cyclosporin released against time over 24 hours and showing the release profiles of minibeads of Examples 5b-d with differing levels of a coating comprising hydroxypropyl methylcellulose compared to the release profile of a minibead of Example 5a which does not have a hydroxypropyl methylcellulose coating.

It is readily apparent from the release profiles in FIG. 3 that the presence of a HPMC subcoat enhances the release profile compared to the non-subcoated minibead of Example 5a. The minibeads comprising a HPMC subcoat give a higher % release of cyclosporin from the minibeads than the non-subcoated minibeads. The same relationship between the % release of cyclosporin from subcoated and non-subcoated minibeads can be seen in the release profiles of FIG. 4.

Example 7: In-Vitro Dissolution Profile of Minibeads of Examples 5e-g

Figure 4:
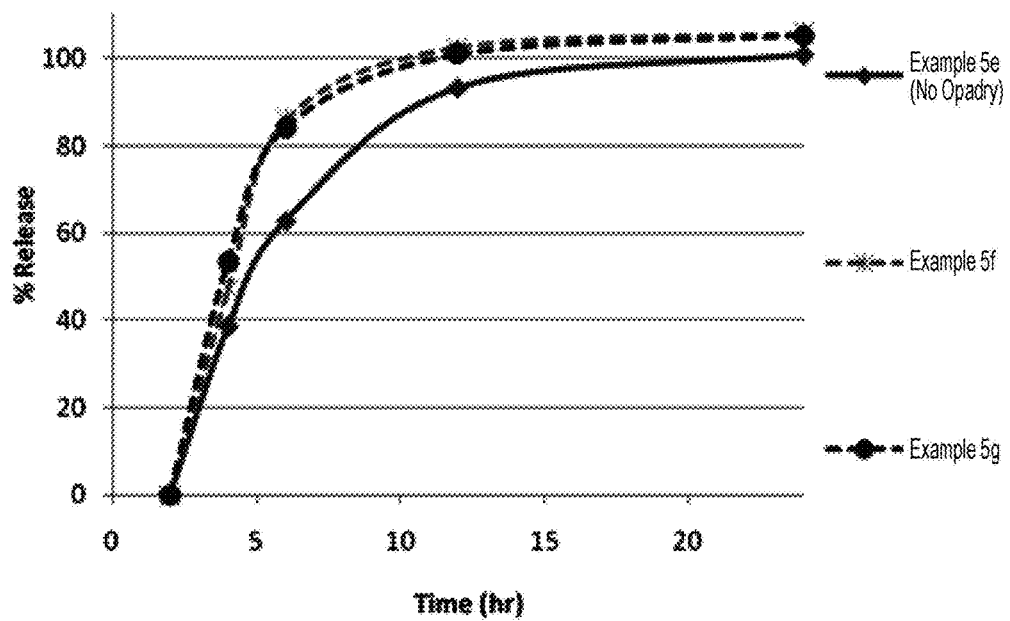
FIG. 4 is a graph plotting % of cyclosporin released against time over 24 hours and showing the release profiles of minibeads of Example 1 and Examples 5f and 5g with differing levels of a coating comprising hydroxypropyl methylcellulose compared to the release profile of a minibead of Example 5e which does not have a hydroxypropyl methylcellulose coating.

Following the procedure described in Example 6 a release profile for each of the minibeads of Examples 5e-g was generated. These release profiles are shown in FIG. 4. FIG. 4 shows that the effect observed in FIG. 3 also occurs when a subcoated bead with a lower level of Surelease®/Pectin is used.

Example 8: In-Vitro Dissolution Profile of Minibeads of Examples 5h-j

Figure 5:
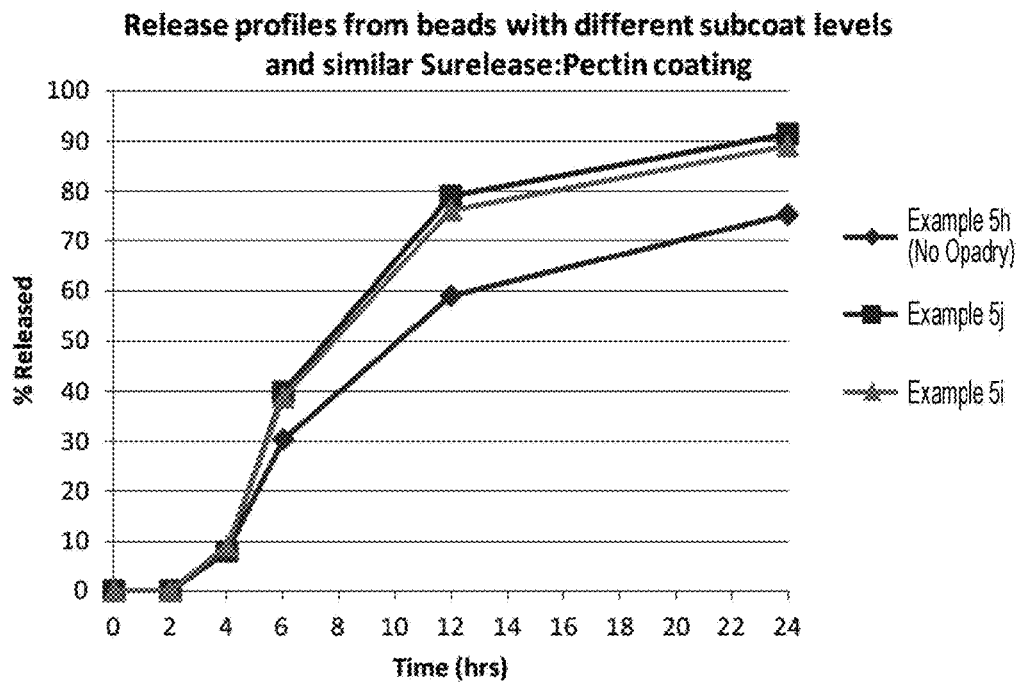
FIG. 5 is a graph plotting % of cyclosporin released against time over 24 hours and showing the release profiles of minibeads of Examples 5i and 5j with differing levels of a coating comprising hydroxypropyl methylcellulose compared to the release profile of a minibead of Example 5h which does not have a hydroxypropyl methylcellulose coating.

Following the procedure described in Example 6 a release profile for each of the minibeads of Examples 5h-j was generated. These release profiles are shown in FIG. 5. FIG. 5 shows that the effect observed in FIGS. 3 and 4 also occurs when a subcoated bead with a higher level of Surelease®/Pectin is used.

Example 9: Preparation of Further Minibeads with a First Coating of Hydroxypropyl Methylcellulose and a Second Coating of Ethylcellulose/Pectin Example 5 describes the use of Opadry® White to provide the hydroxylpropyl methylcellulose subcoat. We now describe the production of further minibeads with a first coating of hydroxypropyl methylcellulose and a second coating of ethylcellulose/pectin using Methocel E5 (supplied by Colorcon Limited) as the hydroxypropyl methylcellulose.

Minibeads were produced in the same way as in Example 5, except Methocel E5 was used instead of Opadry® White for the first coating (subcoat).

A number of minibeads with differing levels of Methocel E5 and differing levels of Surelease®/Pectin were produced. Table 7 shows the % weight gain of Methocel E5 and the % weight gain of Surelease®/Pectin of the minibeads that were produced.

TABLE 7

|  | % weight gain of Methocel E5 | % weight gain of Surelease ®/Pectin |
|---|---|---|
| Example 9a | N/A | 9% |
| Example 9b | 3% | 11% |
| Example 9c | 5.3% | 11% |

Example 9a has no Methocel E5 coating. It is produced by coating a core described in Example 1 with Surelease®/Pectin as described above.

The minibeads of Examples 9a-c have the compositions shown in Table 8.

TABLE 8

| Component | Example 9a | Example 9b w/w % | Example 9c |
|---|---|---|---|
| Cyclosporin A | 9.9 | 9.4 | 9.2 |
| Miglyol ® 810 N | 4.2 | 4.0 | 4.0 |
| Transcutol HP | 15.1 | 14.4 | 14.1 |
| Kolliphor ® EL | 8.4 | 8.1 | 7.9 |
| SDS | 3.7 | 3.5 | 3.4 |
| Sorbitol | 5.2 | 5.0 | 4.9 |
| Gelatin | 45.2 | 43.1 | 42.1 |
| Methocel E5 | N/A | 2.6 | 4.5 |
| Surelease ® (solid contents) | 8.1 | 9.7 | 9.7 |
| Pectin | 0.2 | 0.2 | 0.2 |

Example 10: In-Vitro Dissolution Profile of Minibeads of Examples 9a-c

The in-vitro dissolution profiles of a sample of the minibeads produced in Examples 9a-c were measured using the dissolution test method described in Example 6. The release profile for each of the minibeads of Examples 9a-c is shown in FIG. 6.

Figure 6:
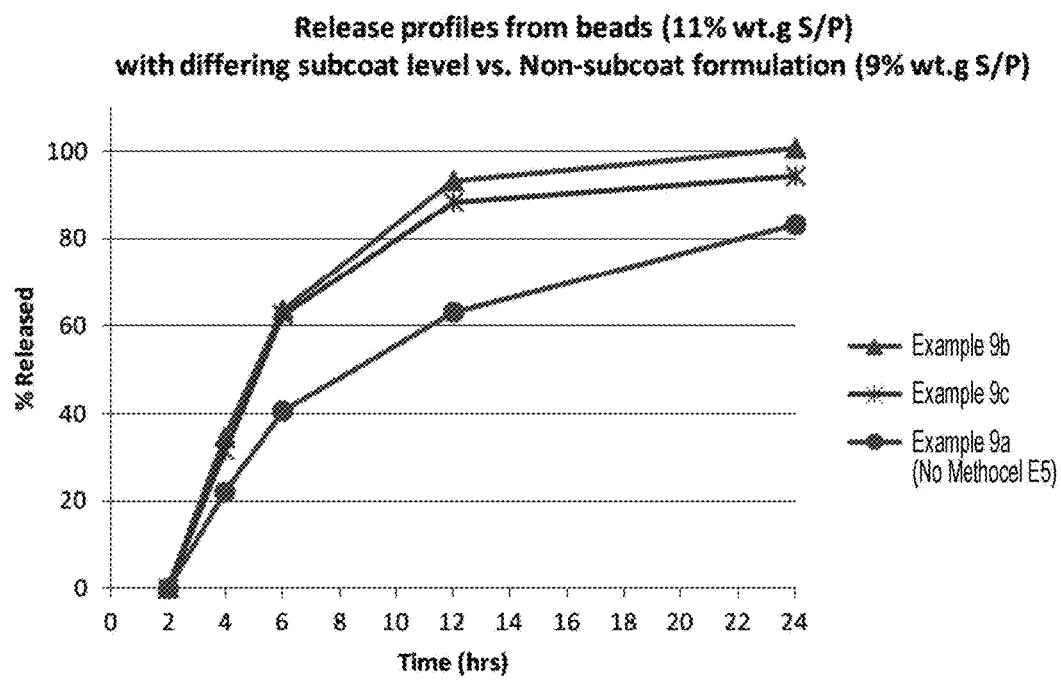
FIG. 6 is a graph plotting % of cyclosporin released against time over 24 hours and showing the release profiles of minibeads of Examples 9b and 9c with differing levels of a hydroxypropyl methylcellulose coating compared to the release profile of a minibead of Example 9a which does not have a hydroxypropyl methylcellulose coating.

FIG. 6 shows that the same result is obtained when Methocel is used as the subcoat as when Opadry® is used as the subcoat.

Figure 7:
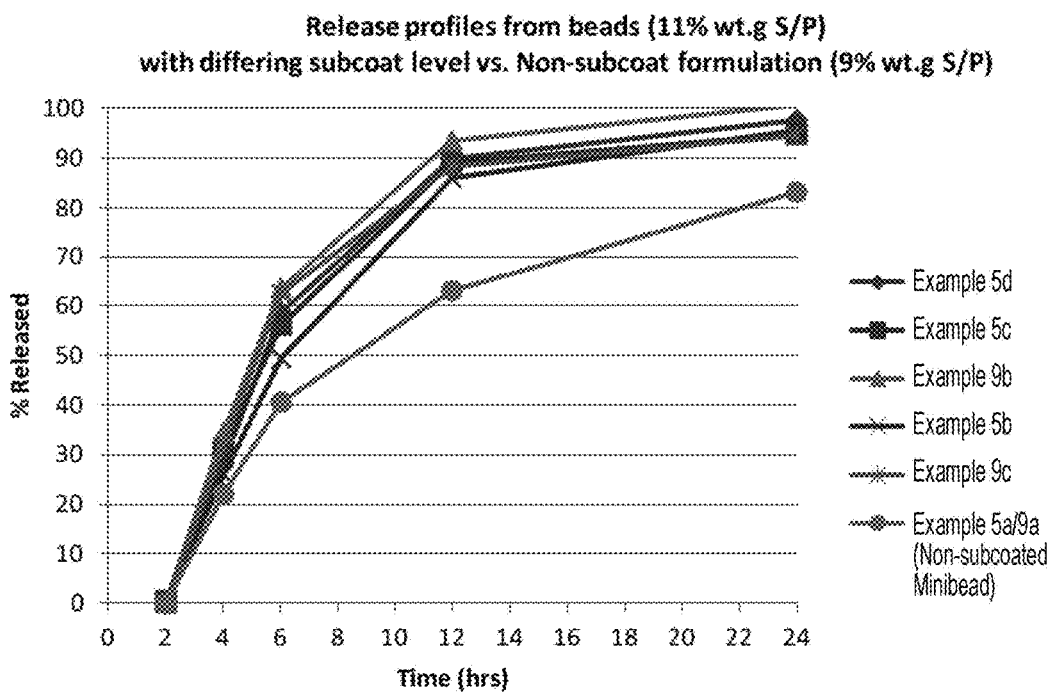
FIG. 7 is a graph containing the release profiles of FIG. 3 and FIG. 6 in a single graph.

Example 11: Comparison of In-Vitro Dissolution Profiles of Examples 5a-d and Examples 9b-c FIG. 7 shows the release profile of each of Examples 5a-d and 9b-c. As mentioned above, FIG. 6 shows the same effect is seen with Methocel subcoated minibeads as Opadry® subcoated minibeads. In addition, when the release profiles generated by the Methocel subcoated minibeads are plotted against the release profile of Opadry® subcoated beads, as in FIG. 7, it can be seen that the Methocel subcoated minibeads and the Opadry® subcoated minibeads give closely matching release profiles.

Example 12: Preparation of Mesalamine Containing Minibeads with a First Coating of Hydroxypropyl Methylcellulose and a Second Coating of Ethylcellulose/Pectin Minibeads containing mesalamine were prepared as described in Example 5 except that the cores were not produced by passing the mixture through a vibrating nozzle but they were produced by hand. In addition cyclosporin was replaced by mesalamine and the oil phase formed during the process to make the core (described in Example 1) did not form a solution; the mesalamine remained as a suspension.

By following this procedure a three populations of minibeads with differing levels of Opadry® and differing levels of Surelease®/Pectin were produced. Table 9 shows the % weight gain of Opadry® and the % weight gain of Surelease®/Pectin of the minibeads that were produced.

TABLE 9

|  | % weight gain of Opadry ® | % weight gain of Surelease ®/Pectin |
|---|---|---|
| Example 12a | N/A | 10.5% |
| Example 12b | 5% | 12% |
| Example 12c | 12% | 11.5% |

Example 12a has no Opadry® coating. It is produced by coating a core described in Example 1 with Surelease®/Pectin as described above.

The minibeads of Examples 12a-c have the compositions shown in Table 10.

TABLE 10

| Component | Example 12a | Example 12b w/w % | Example 12c |
|---|---|---|---|
| Mesalamine | 9.0 | 8.4 | 7.9 |
| Miglyol ® 810 N | 4.7 | 4.4 | 4.2 |
| Transcutol HP | 13.7 | 12.9 | 12.1 |
| Kolliphor ® EL | 7.5 | 7.0 | 6.6 |
| SDS | 3.5 | 3.3 | 3.1 |
| Sorbitol | 5.0 | 4.7 | 4.4 |
| Gelatin | 47.2 | 44.4 | 41.8 |
| Opadry ® | N/A | 4.3 | 9.6 |
| Surelease ® (solid contents) | 9.2 | 10.4 | 10.1 |
| Pectin | 0.2 | 0.2 | 0.2 |

Example 13: In-Vitro Dissolution Profile of Minibeads of Examples 12a-c

Figure 8:
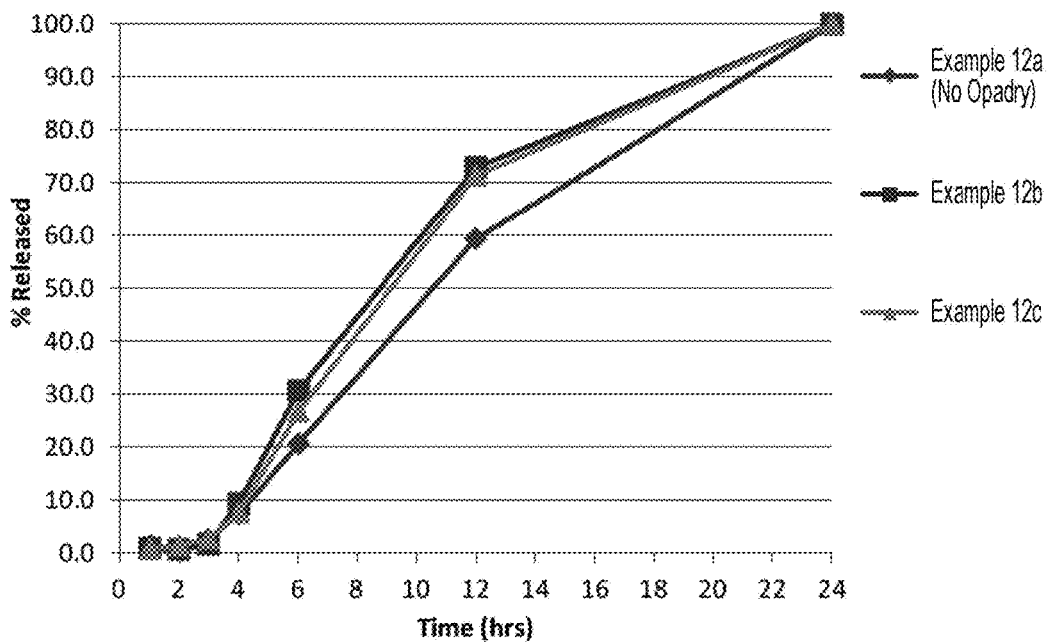
FIG. 8 is a graph plotting % of mesalazine released against time over 24 hours and showing the release profiles of minibeads of Examples 12b and 12c with differing levels of a coating comprising hydroxypropyl methylcellulose compared to the release profile of a minibead of Example 12a which does not have a hydroxypropyl methylcellulose coating.

The in-vitro dissolution profiles of a sample of the minibeads produced in Examples 12a-c were measured using the dissolution test described below: 0.05M pH 7.5 phosphate buffer prepared by dissolving 6.8 g of monobasic potassium phosphate and 1 g of sodium hydroxide in water to make 1000 mL of solution, and adjusting with 10N sodium hydroxide to a pH of 7.5±0.05; 900 mL are used.
USP Apparatus 2 with a paddle speed of 75 RPM.
Dissolution medium temperature: 37° C.±0.5° C.
The release profile for each of the minibeads of Examples 12a-c is shown in FIG. 8.

Example 14: Preparation of Hydralazine HCl Containing Minibeads with a First Coating of Hydroxypropyl Methylcellulose and a Second Coating of Ethylcellulose/Pectin The coated minibeads containing hydralazine HCl were produced by coating a core comprising the hydralazine HCl. Hydralazine HCl is a hydrophilic API, its solubility in water is approximately 8 g/L (i.e. 0.8%); however, it has been found that the API was fully soluble in the aqueous phase of the formulation when heated at 60-70° C.

Core Manufacture

The cores in the form of seamless minibeads were prepared manually as follows.

The aqueous phase was prepared by adding sodium dodecyl sulphate (SDS) and D-sorbitol to purified water under constant stirring until a solution was obtained. Hydralazine HCl and Gelatin were then added to this solution and gentle heat was applied to approximately 60-70° C. to achieve complete melting of gelatin. Stirring was continued until a clear solution was obtained.

The composition of the aqueous phase is shown in Table 11.

TABLE 11

| Component | % w/w |
| --- | --- |
| Hydralazine HCl | 3.5 |
| Gelatin | 18.4 |
| Sorbitol | 2.0 |
| SDS | 1.3 |
| Purified Water | 74.7 |

An oil phase was prepared by mixing together 2-(2-ethoxyethoxy)ethanol (Transcutol HP), polyethoxylated castor oil (Kolliphor® EL) and capric/caprylic triglyceride (Miglyol® 810) with stirring at room temperature to form a solution. The composition of the oil phase is given in Table 12.

TABLE 12

| Component | % w/w |
| --- | --- |
| Transcutol HP | 55.0 |
| Kolliphor® EL | 30.0 |
| Miglyol® 810 | 15.0 |

The oil phase was mixed to form an emulsion with the heated aqueous phase in a ratio of approximately 1:12 (oil phase:aqueous phase). The resulting mixture was stirred at 60-70° C. to achieve homogeneity. The composition of the emulsion is shown in Table 13

TABLE 13

| Component | % w/w |
| --- | --- |
| Hydralazine HCl | 3.2 |
| Transcutol HP | 4.2 |
| Miglyol® 810 | 1.2 |
| Kolliphor® EL | 2.3 |
| Gelatin | 17.0 |
| Sorbitol | 1.8 |
| SDS | 1.3 |
| Purified water | 69.0 |

The resulting mixture was then manually ejected through an orifice into a cooling chamber of medium chain triglyceride (Miglyol® 810) cooling oil at a temperature of 4-10° C. The minibeads were removed from the cooling oil and dried at room temperature for 24 hours.

The composition of the cores is shown in Table 14.

TABLE 14

| Components | % w/w |
| --- | --- |
| Hydralazine HCl | 10.4 |
| Transcutol HP | 13.7 |
| Miglyol® 810 N | 3.7 |

TABLE 14-continued

| Components | % w/w |
| --- | --- |
| Kolliphor® EL | 7.4 |
| Gelatin | 54.8 |
| D-Sorbitol | 6.0 |
| SDS | 4.0 |

The cores produced by the procedure described in this example were coated with Opadry® White 20A28380 (supplied by Colorcon) in the same way as described in Example 1, where appropriate. The cores were directly coated or the Opadry® coated cores, as appropriate, were coated with Surelease®/Pectin as described in Example 5. Six populations of minibeads with differing levels of Opadry® and differing levels of Surelease®/Pectin were produced by following this procedure. Table 15 shows the % weight gain of Opadry® and the % weight gain of Surelease®/Pectin of the minibeads that were produced.

TABLE 15

| | % weight gain of Opadry® | % weight gain of Surelease®/Pectin |
| --- | --- | --- |
| Example 14a | N/A | 11% |
| Example 14b | 6.4% | 10.8% |
| Example 14c | 11.5% | 11.1% |
| Example 14d | N/A | 17.7% |
| Example 14e | 6.4% | 17.9% |
| Example 14f | 11.5% | 16.6% |

Examples 14a and 14d have no Opadry® coating. These Examples are produced by coating a core described in Example 1 with Surelease®/Pectin as described above.

The minibeads of Examples 14a-f have the compositions shown in Table 16.

TABLE 16

| Component | Example 14a | Example 14b | Example 14c | Example 14d | Example 14e | Example 14f |
| --- | --- | --- | --- | --- | --- | --- |
| | w/w % | | | | | |
| Hydralazine | 9.4 | 8.8 | 8.4 | 8.8 | 8.3 | 8.0 |
| Miglyol® 810 N | 3.4 | 11.6 | 11.1 | 11.7 | 10.9 | 10.5 |
| Transcutol HP | 12.3 | 3.1 | 3.0 | 3.1 | 3.0 | 2.9 |
| Kolliphor® EL | 6.7 | 6.3 | 6.0 | 6.3 | 5.9 | 5.7 |
| SDS | 3.6 | 46.5 | 44.2 | 46.6 | 43.7 | 42.1 |
| Sorbitol | 5.4 | 5.1 | 4.8 | 5.1 | 4.8 | 4.6 |
| Gelatin | 49.4 | 3.4 | 3.2 | 3.4 | 3.2 | 3.1 |
| Opadry® | N/A | 5.4 | 9.3 | N/A | 5.1 | 8.9 |
| Surelease® (solid contents) | 9.9 | 9.8 | 10.0 | 15.0 | 15.1 | 14.2 |

Example 15: In-Vitro Dissolution Profile of Minibeads of Examples 14a-f

The in-vitro dissolution profiles of a sample of the minibeads produced in Examples 14a-f were measured using the dissolution test method described in Example 13. The release profile for each of the minibeads of Examples 14a-f is shown in FIG. 9.

Figure 9:
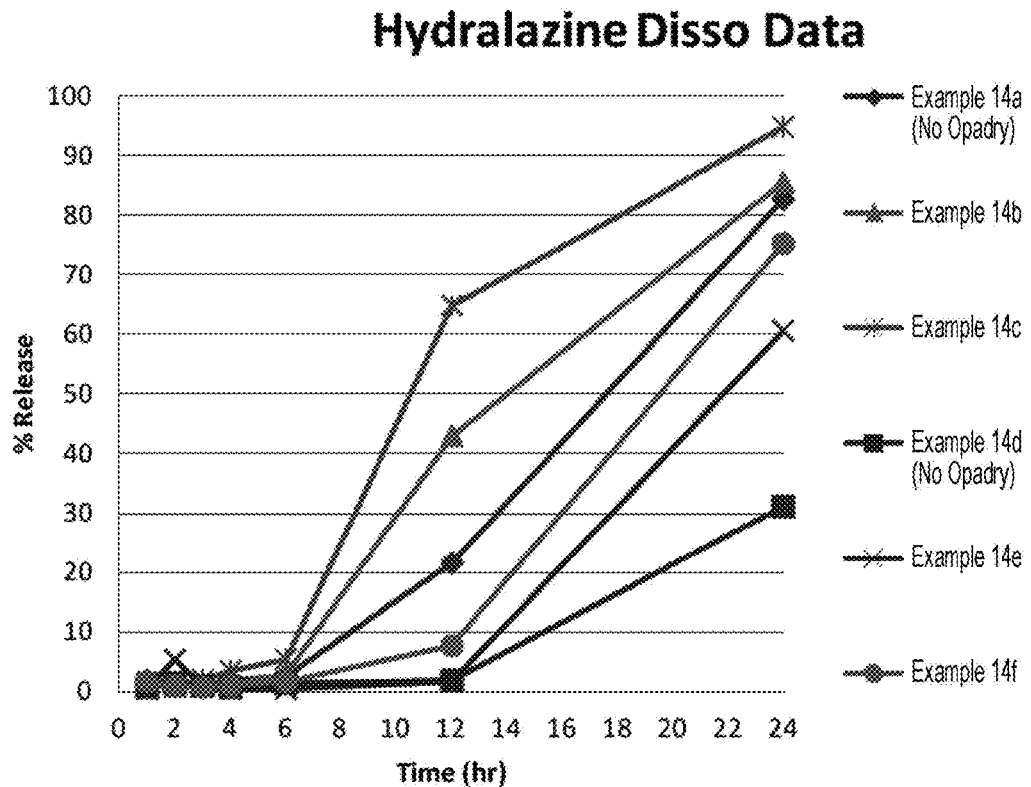
FIG. 9 is a graph plotting % of hydralazine released against time over 24 hours and showing the release profiles of minibeads of Examples 14b-c and 14e-f with differing levels of a coating comprising hydroxypropyl methylcellulose and differing levels of a Sureleas/Pectin coating compared to the release profiles of a minibeads of Example 14a and 14d which do not have a hydroxypropyl methylcellulose coating.

The release profile of FIG. 9 shows the same effect as that observed in the previous examples—an increased % release of the active ingredient, hydralazine, from the minibeads with a HPMC subcoat versus non-subcoated minibeads with comparable levels of Surelease®/Pectin. For example, a comparison between non-subcoated Example 14a and sub-coated Example 14c shows the higher % release effect of the HPMC subcoat. The same is true of a comparison between Example 14d and Example 14f.

Example 16: In-Vitro Dissolution Profile of Minibeads from Different Batches

Minibead cores were prepared according to the procedure described in Example 1. From these cores, 3 populations of minibeads coated with both an Opadry® subcoat and a Surelease®/pectin overcoat were produced and 3 populations of minibeads with only a Surelease®/Pectin coating were produced. The 3 populations with both an Opadry® subcoat and a Surelease®/pectin overcoat had an amount of coating corresponding to a 5% weight gain of Opadry® and an 11.5% weight gain of Surelease®/Pectin. The 3 populations with only a Surelease®/pectin coating had an amount of coating corresponding to a 9% weight gain of Surelease®/Pectin. The compositions of the minibeads with an Opadry® subcoat and without an Opadry® subcoat are shown in Table 17.

TABLE 17

| Component | With subcoat (%) | W/o subcoat (%) |
|---|---|---|
| Cyclosporin A | 9.2 | 9.9 |
| Miglyol® 810 N | 3.9 | 4.2 |
| Transcutol HP | 14.0 | 15.1 |
| Kolliphor® EL | 7.9 | 8.4 |
| SDS | 3.4 | 3.7 |
| Sorbitol | 4.9 | 5.2 |
| Gelatin | 42.1 | 45.2 |
| Opadry® | 4.3 | N/A |
| Surelease® (solid contents) | 10.1 | 8.1 |
| Pectin | 0.2 | 0.2 |

Figure 10:
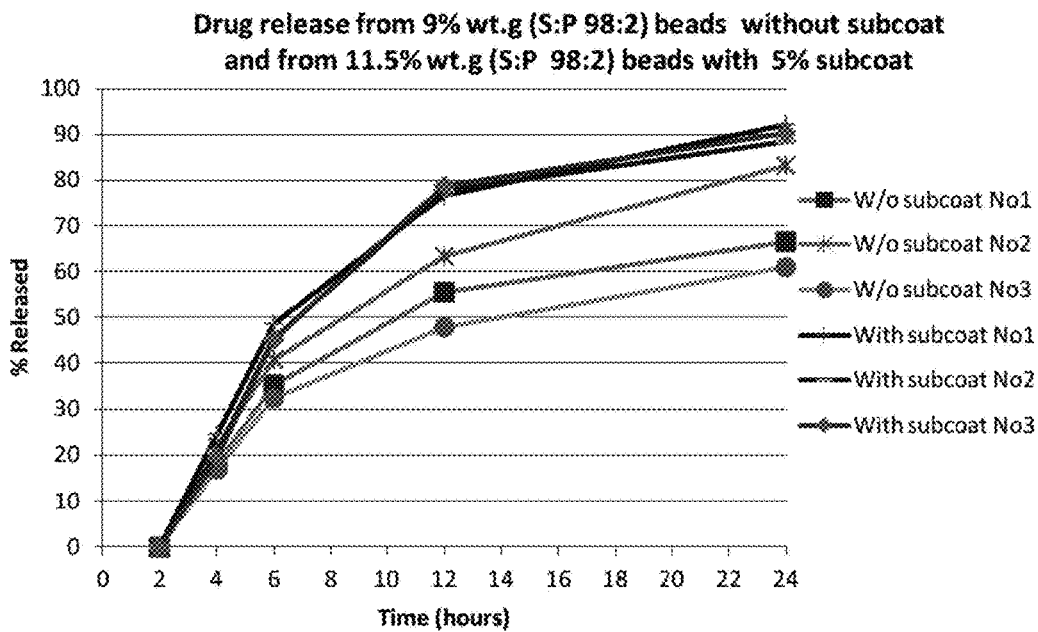
FIG. 10 is a graph plotting % of cyclosporin released against time over 24 hours and showing the reduction in the variability of the release profiles of different batches of minibeads with a coating comprising hydroxypropyl methylcellulose and a Surelease/Pectin second coating.

The dissolution profile of these 6 populations of minibeads was tested using the dissolution test protocol of Example 6 to give the dissolution profile shown in FIG. 10.

FIG. 10 shows a wide variation in the release profiles for the populations of minibeads lacking a HPMC subcoat; % release values at 12 hours range from 48% to 63% and at 24 hours they range from 61% to 83%. In stark contrast to the results obtained for the minibeads lacking a HPMC subcoat, the minibeads having a HPMC subcoat have very little variation in the % release of the different batches.

Example 16: Measurement of Coating Thickness

Figure 11:
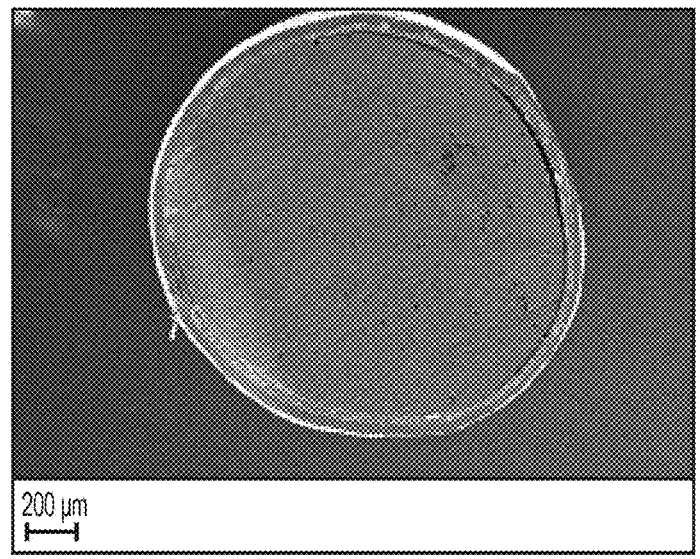
FIG. 11 is a scanning electron microscope image of a cross section of a minibead of the invention.
Figure 12:
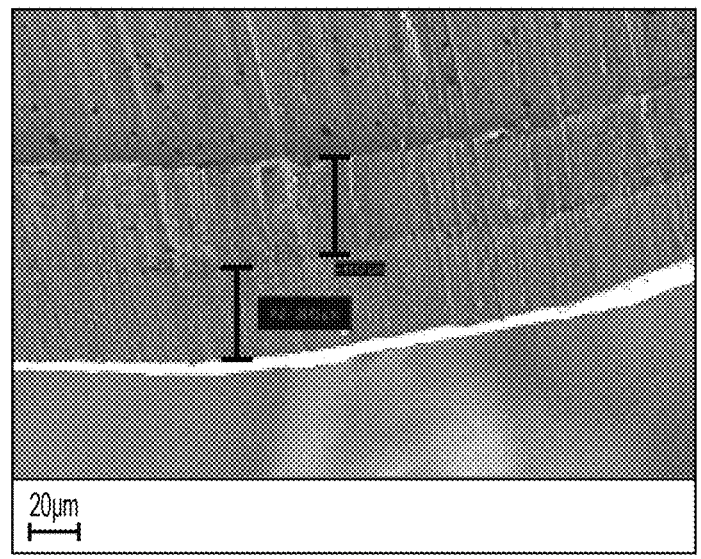
FIG. 12 is an enlarged image of a portion of the image in FIG. 11 showing two distinct layers of coatings.

A minibead produced according to the procedure disclosed herein was studied under a scanning electron microscope (SEM). The minibead had a first coating of Opadry® with a weight gain of 10% and a second coating of Surelease®/Pectin (98:2 ratio) with a weight gain of 11%. The minibead was cut in half at the widest point of the minibead. The cross sectional surface of the bead was then studied under the SEM. FIG. 11 shows a SEM image of the cross section of the minibead and FIG. 12 provides a magnified version of the image of FIG. 11. FIG. 12 clearly shows the distinct first coating and second coating. From the SEM image it was possible to determine that the thickness of the first coating was 41 µm and the thickness of the second coating was 40 µm.

The invention is further illustrated by the following numbered clauses.

1. A pharmaceutical formulation comprising a core and a coating, wherein the core comprises a hydrogel forming polymer matrix and a pharmaceutically active ingredient and the coating comprises or is a water soluble cellulose ether, and the coating is present in an amount corresponding to a weight gain due to the coating of from 0.5% to 20% by weight of the core.

2. The pharmaceutical formulation of clause 1, wherein the coating has a thickness of from 1 µm to 1 mm.

3. A pharmaceutical formulation comprising a core and a coating, wherein the core comprises a hydrogel forming polymer matrix and a pharmaceutically active ingredient, wherein the coating comprises or is a water-soluble cellulose ether and the coating has a thickness of from 1 µm to 1 mm.

4. The pharmaceutical formulation of clause 3, wherein the coating has a thickness of from 1 µm to 500 µm.

5. A pharmaceutical formulation comprising a core and a coating, wherein the core comprises a pharmaceutically active ingredient and the coating comprises or is a water-soluble cellulose ether and the coating is present in an amount to provide a % in solution of more than 60% of the pharmaceutically active ingredient at 1 hour from the start of a dissolution test to measure the % in solution of the pharmaceutically active ingredient in a dissolution medium consisting of water, the dissolution test being carried out in accordance with USP <711> Dissolution using Apparatus II (paddle apparatus) operated with a paddle speed of 75 rpm and with the dissolution medium at a temperature of 37° C.

6. The pharmaceutical formulation of clause 5, wherein the % in solution may also be selected from a range from: 60% to 90%, 65% to 85%, 68% to 83%, 68% to 73%, 72% to 78%, or 77% to 83%.

7. A pharmaceutical formulation comprising a core and a coating, wherein the core comprises a pharmaceutically active ingredient and the coating comprises or is a water-soluble cellulose ether, further wherein the coating is present in an amount to provide a higher % in solution of the pharmaceutically active ingredient from the formulation than a formulation without the coating at 0.5 hours from the start of a dissolution test to measure the % in solution of the pharmaceutically active ingredient in a dissolution medium consisting of water, the dissolution test being carried out in accordance with USP <711> Dissolution using Apparatus II (paddle apparatus) operated with a paddle speed of 75 rpm and with the dissolution medium at a temperature of 37° C.

8. The pharmaceutical formulation of clause 7, wherein the higher % in solution of the pharmaceutically active ingredient is at 0.5 hours and a time point selected from: 20 mins, 40 mins, 1 hour 1.5 hours, and any combination thereof.

9. The pharmaceutical formulation of clause 7 or clause 8, wherein the higher % in solution of the pharmaceutically active ingredient is for the period up to 1.5 hours from the start of the dissolution test.

10. The pharmaceutical formulation of any of clauses 5 to 9, wherein the coating is present in an amount corresponding to a weight gain due to the coating of from 1% to 9% by weight of the core.

11. A pharmaceutical formulation comprising a core and a coating, wherein the core comprises a pharmaceutically active ingredient and the coating comprises or is a water-soluble cellulose ether, further wherein the coating is present in an amount to provide a % in solution of the pharmaceutically active ingredient of more than 75% at 12 hours from the start of a dissolution test in a dissolution medium consisting of water, the dissolution test being carried out in accordance with USP <711> Dissolution using Apparatus II (paddle apparatus) operated with a paddle speed of 75 rpm and with the dissolution medium at a temperature of 37° C.

12. The pharmaceutical formulation of clause 11, wherein the % in solution of the pharmaceutically active ingredient at 24 hours from the start of the dissolution test is more than 50%.

13. A pharmaceutical formulation comprising a core and a coating, wherein the core comprises a pharmaceutically active ingredient, optionally a hydrophobic active ingredient, and the coating comprises or is a water-soluble cellulose ether, further wherein the coating is present in an amount to provide a higher % in solution of the pharmaceutically active ingredient from the formulation than a formulation without the coating at 12 hours from the start of a dissolution test in a dissolution medium consisting of water, the dissolution test being carried out in accordance with USP <711> Dissolution using Apparatus II (paddle apparatus) operated with a paddle speed of 75 rpm and with the dissolution medium at a temperature of 37° C.

14. The pharmaceutical formulation of clause 13, wherein the coating is present in an amount to provide a higher % in solution of the pharmaceutically active ingredient for a period selected from one of those spanning from: 10 to 16 hours; 10 to 18 hours; 10 to 24 hours; 12 to 18 hours; 12 to 22 hours; 12 to 24 hours; and 4 to 24 hours.

15. A pharmaceutical formulation of any of clauses 11 to 14, wherein the pharmaceutically active ingredient is a hydrophobic active ingredient.

16. A pharmaceutical formulation comprising a core and a coating, wherein the core comprises a pharmaceutically active ingredient and the coating comprises or is a water-soluble cellulose ether, further wherein the coating is present in an amount to provide a decrease in % in solution of the pharmaceutically active ingredient of 15 or less, optionally 10 or less, in a period from 8 hours to 16 hours from the start of a dissolution test in a dissolution medium consisting of water, the dissolution test being carried out in accordance with USP <711> Dissolution using Apparatus II (paddle apparatus) operated with a paddle speed of 75 rpm and with the dissolution medium at a temperature of 37° C.

17. The pharmaceutical formulation of any of clauses 13 to 15, wherein the coating is present in an amount corresponding to a weight gain due to the coating of from 8% to 20%.

18. The pharmaceutical formulation of any of clauses 1 to 4, wherein the pharmaceutical formulation comprises a second coating comprising or being a delayed release polymer.

19. A pharmaceutical formulation comprising a core, a first coating and a second coating outside the first coating, wherein the core comprises a pharmaceutically active ingredient, the first coating comprises or is a water-soluble cellulose ether, further wherein the second coating comprises or is a delayed release polymer, wherein the first coating is present in an amount to provide a higher % release of the pharmaceutically active ingredient from the pharmaceutical formulation than a corresponding pharmaceutical formulation without the first coating at 12 hours from the start of a dissolution test, wherein the dissolution test is carried out in accordance with USP <711> Dissolution using Apparatus II (paddle apparatus) operated with a paddle speed of 75 rpm and with the dissolution medium at a temperature of 37° C.

20. The pharmaceutical formulation of clause 19, wherein the first coating is present in an amount to provide a higher % release of the pharmaceutically active ingredient in the period from 6 hours to 22 hours.

21. A pharmaceutical formulation comprising a core, a first coating and a second coating outside of the first coating, wherein the core comprises a pharmaceutically active ingredient, the first coating comprises or is a water-soluble cellulose ether, further wherein the second coating comprises or is a delayed release polymer, wherein the first coating is present in an amount to provide a % release of the pharmaceutically active ingredient of more than 70% at 12 hours from the start of a two stage dissolution test, wherein the dissolution test is carried out in accordance with USP <711> Dissolution using Apparatus II (paddle apparatus) operated with a paddle speed of 75 rpm and with the dissolution medium at a temperature of 37° C.

22. The pharmaceutical formulation of clause 21, wherein the first coating is present in an amount to allow release of 80% or more of the pharmaceutically active ingredient at 12 hours.

23. The pharmaceutical formulation of clause 21 or clause 22, wherein the first coating is present in an amount to provide a % release of from 80% to 95% or from 85% to 95% of the pharmaceutically active ingredient at 12 hours.

24. The pharmaceutical formulation of any of clauses 21 to 23, wherein the first coating is present in an amount to provide a % release of the pharmaceutically active ingredient in an amount of more than 45%, optionally from 45% to 65% at 6 hours from the start of the two stage dissolution test.

25. The pharmaceutical formulation of any of clauses 21 to 24, wherein the first coating is present in an amount to provide a % release of the pharmaceutically active ingredient in an amount of more than 25%, optionally from 25% to 40%, at 4 hours from the start of the dissolution test.

26. The pharmaceutical formulation of any of clauses 21 to 23, wherein the first coating is present in an amount to provide a % release of the pharmaceutically active ingredient in an amount of more than 25%, optionally from 25% to 35%, at 6 hours.

27. A pharmaceutical formulation comprising a core, a first coating and a second coating outside of the first coating, wherein the core comprises a pharmaceutically active ingredient, the first coating comprises or is a water-soluble cellulose ether, further wherein the second coating comprises or is a delayed release polymer, wherein the first coating is present in an amount to provide a % release of the pharmaceutically active ingredient of more than 70% at 6 hours from the start of a dissolution test, wherein the dissolution test is carried out in accordance with USP <711> Dissolution using Apparatus II (paddle apparatus) operated with a paddle speed of 75 rpm and with the dissolution medium at a temperature of 37° C.

28. The minibead of clause 27, wherein the first coating is present in an amount to provide a % release of from 75% to 95% or from 80% to 90% of the pharmaceutically active ingredient at 6 hours.

29. A pharmaceutical formulation comprising a core, a first coating and a second coating outside of the first coating, wherein the core comprises a pharmaceutically active ingredient, the first coating comprises or is a water-soluble cellulose ether, further wherein the second coating comprises or is a delayed release polymer, wherein the first coating is present in an amount to provide a % release of the pharmaceutically active ingredient of more than 40% at 12 hours from the start of a dissolution test, wherein the two stage dissolution test is carried out in accordance with USP <711> Dissolution using Apparatus II (paddle apparatus) operated with a paddle speed of 75 rpm and with the dissolution medium at a temperature of 37° C.

30. A pharmaceutical formulation of clause 29, wherein the pharmaceutically active ingredient is a hydrophilic active ingredient.

31. The pharmaceutical formulation of clause 30, wherein the first coating is present in an amount to allow release of from 40% to 80% of the active ingredient at 12 hours.

32. The pharmaceutical formulation of any of clauses 18 to 31 wherein the first coating is in contact with the core.

33. The pharmaceutical formulation of any of clauses 18 to 32, wherein the second coating is on the first coating.

34. The pharmaceutical formulation of any of clauses 18 to 33, wherein the second coating is present in an amount corresponding to a weight gain due to the second coating of from 2% to 40%, optionally the weight gain due to the second coating is selected from a range of from: 4% to 30%, 4% to 7%, 7% to 40%, 7% to 30%, 8% to 25%, 8% to 20%, 2% to 25%, 2% to 20%, 4% to 25%, 4% to 20%, 4% to 15%, 4% to 13%, 7% to 15%, 7% to 13%, 8% to 12%, 9% to 12% and 20% to 25%.

35. The pharmaceutical formulation of any of clauses 18 to 34, wherein the delayed release polymer is selected from an enteric polymer, a pH independent polymer, a pH dependent polymer and a polymer specifically susceptible to degradation by bacterial enzymes in the gastrointestinal tract, or a combination of two or more such polymers.

36. The pharmaceutical formulation of any of clauses 18 to 35, wherein the delayed release polymer is water-soluble or water-permeable in an aqueous medium with a pH greater than 6.5.

37. The pharmaceutical formulation of clause 18 to 36, wherein the delayed release polymer is or comprises a pH-independent polymer, for example ethyl cellulose.

38. The pharmaceutical formulation of any preceding clause, wherein the water-soluble cellulose ether is selected from any one or a combination of: methyl cellulose, hydroxyethyl cellulose, hydroxypropyl cellulose, hydroxyethyl methylcellulose and hydroxypropylmethyl cellulose.

39. The pharmaceutical formulation of clause 38, wherein the water-soluble cellulose ether is hydroxypropylmethyl cellulose.

40. The pharmaceutical formulation of any of clauses 3 to 9, 11 to 16 or 18 to 39, wherein the first coating is present in an amount corresponding to a weight gain due to the coating of from 0.5% to 20% by weight of the core.

41. The pharmaceutical formulation of any of clauses 1 to 9, 11 to 16 or 18 to 40, wherein the weight gain due to the coating is in a range selected from: 0.5% to 15%; 1% to 15%; 1% to 12%; 1% to 10%; 1% to 8%; 1% to 6%; 1% to 4%, 2% to 10%; 2% to 8%; 2% to 6%; 2% to 4%; 4% to 8%; 4% to 7%, 5% to 7%; 7% to 20%; 7% to 16%; 9% to 20%; 9% to 16%; 10% to 15%; and 12% to 16%.

42. The pharmaceutical formulation of clauses 1 to 14, 16 to 29, 31 to 41, wherein the pharmaceutically active ingredient is a hydrophobic pharmaceutically active ingredient or a hydrophilic pharmaceutically active ingredient.

43. The pharmaceutical formulation of any of clauses 5 to 42, wherein the core comprises a hydrogel forming polymer matrix.

44. The pharmaceutical formulation of any of clauses 1 to 4 or 43, optionally wherein the hydrogel forming polymer matrix is or comprises a hydrocolloid, a non-hydrocolloid gum or chitosan.

45. The pharmaceutical formulation of any of clauses 44, wherein the hydrogel forming polymer matrix is or comprises a reversible hydrocolloid, optionally a thermoreversible hydrogel forming polymer.

46. The pharmaceutical formulation of clause 44, wherein the hydrogel forming polymer matrix comprises or is an irreversible hydrocolloid.

47. The pharmaceutical formulation of any of clauses 1 to 4, 43 or 44 wherein the hydrogel forming polymer matrix is or comprises gelatin, agar, a polyethylene glycol, starch, casein, chitosan, soya bean protein, safflower protein, alginates, gellan gum, carrageenan, xanthan gum, phthalated gelatin, succinated gelatin, cellulosephthalate-acetate, oleoresin, polyvinylacetate, polymerisates of acrylic or methacrylic esters and polyvinylacetate-phthalate and any derivative of any of the foregoing; or a mixture of one or more such a hydrogel forming polymers.

48. The pharmaceutical formulation of any of clauses 1 to 4 or 43 to 47 wherein the hydrogel forming polymer matrix is or comprises a hydrocolloid selected from carrageenan, gelatin, agar and pectin, or a combination thereof optionally selected from gelatin and agar or a combination thereof, more optionally the polymer of the a hydrogel forming polymer matrix is or comprises gelatin.

49. The pharmaceutical formulation of clause 47 or clause 48, wherein the hydrogel forming polymer further comprising a plasticiser, optionally a plasticiser selected from glycerin, a polyol for example sorbitol, polyethylene glycol and triethyl citrate or a mixture thereof, particularly sorbitol.

50. The pharmaceutical formulation of any of clauses 44 wherein the hydrogel forming polymer matrix is or comprises a non-hydrocolloid gum optionally selected from a cross-linked salt of alginic acid.

51. The pharmaceutical formulation of clause 44 wherein the hydrogel forming polymer matrix is or comprises chitosan.

52. The pharmaceutical formulation of any of clauses 1 to 4, 43 or 51, wherein the hydrogel forming polymer matrix encapsulates the active ingredient.

53. The pharmaceutical formulation of any of clauses 1 to 4, or 43 to 52, wherein the core is in the form of a solid colloid the colloid comprising a continuous phase and a disperse phase, wherein the continuous phase comprises the hydrogel forming polymer matrix.

54. The pharmaceutical formulation of clause 53, wherein the disperse phase is or comprises a hydrophobic phase.

55. The pharmaceutical formulation of clause 53, wherein the disperse phase is or comprises a liquid lipid and optionally a solvent miscible therewith.

56. The pharmaceutical formulation of clause 54 wherein the disperse phase is or comprises a glyceride composition, optionally wherein the disperse phase is or comprises a fatty acid monoglyceride, diglyceride or triglyceride or a combination thereof, or the disperse phase is or comprises a caprylic/capric triglyceride composition.

57. The pharmaceutical formulation of any of clauses 53 to 55 wherein the disperse phase is or comprises an oil selected from a vegetable oil and a petrochemical oil.

58. The pharmaceutical formulation of any of clauses 53 to 55 wherein the disperse phase is or comprises a polyunsaturated fatty acid, for example selected from omega-3 oils for example eicosapentaenoic acid, docosohexaenoic acid, alpha-linoleic acid and conjugated linoleic acid.

59. The pharmaceutical formulation of any of clauses 53 to 55 wherein the disperse phase is or comprises an oil selected from olive oil, sesame oil, coconut oil, palm kernel oil and neem oil.

60. The pharmaceutical formulation of any of clauses 53 to 55 wherein the disperse phase is or comprises an oil phase selected from caprylic/capric triglyceride; caprylic/capric/linoleic triglyceride; caprylic/capric/succinic triglyceride; and propylene glycol dicaprylate/dicaprate.

61. The pharmaceutical formulation of any of clauses 53 to 55 wherein the disperse phase is or comprises an oil phase selected from linoleoyl macrogolglycerides (polyoxylglycerides) and caprylocaproyl macrogolglycerides.

62. The pharmaceutical formulation of any of clauses 53 to 61 wherein the disperse phase is or comprises an oil phase with an HLB of from 0 to 10.

63. The pharmaceutical formulation of any of clauses 53 to 61, wherein the disperse phase further is or comprises a solvent, wherein the solvent is miscible with the disperse phase and water, optionally wherein the solvent is selected from 2-(2-ethoxyethoxy)ethanol and a poly(ethylene glycol), particularly wherein the solvent is 2-(2-ethoxyethoxy)ethanol.

64. The pharmaceutical formulation of clause 63 wherein the solvent is or comprises a poly(ethylene glycol) selected from a PEG with an average molecular weight of from about 200 to about 400, for example PEG 200 or PEG 400.

65. The pharmaceutical formulation of any of clauses 53 to 64 wherein the disperse phase is or comprises an oil phase which represents 10-85%, for example 20-30%, by dry weight of the core.

66. The pharmaceutical formulation of clause 53 wherein the disperse phase is or comprises an oil phase comprising a medium chain triglyceride, a polyethoxylated castor oil and 2-(ethoxyethoxy)ethanol.

67. The pharmaceutical formulation of any of clauses 53 to 66 wherein the active ingredient is in solution or suspended in the continuous phase or the disperse phase.

68. The pharmaceutical formulation of any of clauses 67, wherein the active ingredient is:
   a. in solution in the disperse phase;
   b. in solution in the continuous phase;
   c. suspended in the disperse phase; or
   d. suspended in the continuous phase.

69. The pharmaceutical formulation of clause 67, wherein the active ingredient is: a hydrophobic active ingredient and is in solution in the disperse phase or suspended in the continuous phase; or a hydrophilic active ingredient and is suspended in the disperse phase or in solution in the continuous phase.

70. The pharmaceutical formulation according to any preceding clause, wherein the core further comprises a surfactant, optionally wherein the surfactant is an anionic surfactant, optionally selected from alkyl sulphates, carboxylates or phospholipids, or a non-ionic surfactant, optionally selected from sorbitan-based surfactants, PEG-fatty acids, or glyceryl fatty acids, or poloxamers, or a combination thereof.

71. The pharmaceutical formulation according to any of clauses 53 to 70, wherein the core further comprises a surfactant present in at least the continuous phase, the surfactant having an HLB value of at least 10, for example greater than 20.

72. The pharmaceutical formulation according to clause 71, wherein the surfactant in the continuous phase is an anionic surfactant, for example at least one surfactant selected from fatty acid salts and bile salts, particularly an alkyl sulphate, for example sodium dodecyl sulphate.

73. The pharmaceutical formulation according to any one of clauses 53 to 72 wherein the disperse phase is or comprises a non-ionic surfactant.

74. The pharmaceutical formulation according to any of clauses 53 to 73 wherein the disperse phase further comprises a surfactant with an HLB value in the range of from 1 to 20, for example from 1 to 15, 1 to 10, 10 to 20, 10 to 15, 1 to 5.

75. The pharmaceutical formulation according to clause 53 wherein the disperse phase comprises an oil phase selected from caprylic/capric triglyceride; caprylic/capric/linoleic triglyceride; caprylic/capric/succinic triglyceride; and propylene glycol dicaprylate/dicaprate; and a polyethoxylated castor oil.

76. The pharmaceutical formulation of any of clauses 53 to 75 wherein the disperse phase further comprises a solvent, for example 2-(2-ethoxyethoxy)ethanol.

77. The pharmaceutical formulation of any preceding clause wherein the pharmaceutical formulation further comprises an excipient selected from: a surfactant, a solubiliser, a permeability enhancer, a disintegrant, a crystallisation inhibitor, a pH modifier, a stabiliser, or a combination thereof.

78. The pharmaceutical formulation of any of clauses 18 to 77, wherein the second coating further comprises a pore former.

79. The pharmaceutical formulation of the clause 78, wherein the second coating comprises a delayed release polymer and a pore former, optionally present in a polymer: pore former ratio of from: 80:20 to 99.5:0.5, 90:10 to 99.5 to 0.5; 95:5 to 99.5:0.5; 97:3 to 99:1, optionally the ratio is 98:2.

80. The pharmaceutical formulation of clause 78 or clause 79, wherein the pore former is a bacterially degradable polymer, optionally a bacterially degradable polysaccharide.

81. The pharmaceutical formulation according to clause 53, wherein the disperse phase is or comprises:
   a pharmaceutically active ingredient, for example cyclosporin, hydralazine and mesalamine;
   a medium chain mono- di- or tri-glyceride, for example caprylic/capric triglyceride;
   a non-ionic surfactant, for example a polyethoxylated castor oil; and
   a solvent, for example 2-(ethoxyethoxy)ethanol
and wherein the continuous phase is or comprises:
   an anionic surfactant, for example at least one surfactant selected from fatty acid salts, alkyl sulphates and bile salts, particularly an alkyl sulphate, for example sodium dodecyl sulphate
   a hydrogel forming polymer matrix which is or comprises a hydrocolloid selected from carrageenan, gelatin, agar and pectin, or a combination thereof optionally selected from gelatin and agar or a combination thereof, more optionally the polymer of the a hydrogel forming polymer matrix is or comprises gelatin; and
   optionally a plasticiser, for example a plasticiser selected from glycerin, a polyol for example sorbitol, polyethylene glycol and triethyl citrate or a mixture thereof, particularly sorbitol.

82. The pharmaceutical formulation of any of clauses 1 to 80, wherein the core comprises a hydrogel forming polymer comprising gelatin in an amount of 300 to 700 mg/g, the core further comprising medium chain mono, di or tri-glycerides in an amount of 20 to 200 mg/g, and the pharmaceutical formulation further comprises the following components:
   co-solvent in an amount of 150 to 250 mg/g;
   non-ionic surfactant in an amount of 80 to 200 mg/g;
   anionic surfactant in an amount of 15 to 50 mg/g.

83. The pharmaceutical formulation of any preceding clause, wherein the formulation is in the form of a minibead.

84. The pharmaceutical formulation of any preceding clause, wherein the largest cross sectional dimension of a core is from about 0.01 mm to about 5 mm, optionally wherein the formulation is in the form of a minibead.

85. A pharmaceutical formulation of any one of clauses 83 or 84 wherein the minibead is spheroidal and has an aspect ratio of no more than 1.5, for example from 1.1 to 1.5.

86. A pharmaceutical formulation comprising a multiplicity of minibeads of any one of clauses 83 to 85.

87. The pharmaceutical formulation of any preceding clause, wherein the formulation is for oral administration.

88. The pharmaceutical formulation of any preceding clause, the core having the characteristics of a core formed by mixing a disperse phase with a continuous phase to form a colloid, wherein the continuous phase is an aqueous phase comprising hydrogel forming polymer and the disperse phase is a hydrophobic phase, wherein the pharmaceutically active ingredient is in the continuous phase or the disperse phase, wherein the colloid is gelled to form the core.

89. A pharmaceutical formulation according to clause 88, wherein the disperse phase is as defined in any of clauses 54 to 66 or 73 to 76.

90. A pharmaceutical formulation according to clause 88 or clause 89, wherein the a hydrogel forming polymer is or comprises one or more a hydrogel forming polymer selected from gelatin, agar, a polyethylene glycol, starch, casein, chitosan, soya bean protein, safflower protein, alginates, gellan gum, carrageenan, xanthan gum, phthalated gelatin, succinated gelatin, cellulosephthalate-acetate, cellulosephthalate-acetate, oleoresin, polyvinylacetate, polymerisates of acrylic or methacrylic esters and polyvinylacetate-phthalate and any derivative of any of the foregoing.

91. The pharmaceutical formulation according to any of clauses 88 to 90, wherein the continuous phase further comprises an anionic surfactant, for example sodium dodecyl sulphate (SDS).

92. The pharmaceutical formulation of any of clauses 88 to 91, wherein the pharmaceutical formulation has the characteristics of a pharmaceutical formulation formed by coating a core with the first coating.

93. A pharmaceutical formulation according to clause 88 wherein the core comprises a hydrogel forming polymer matrix and a hydrophobic phase dispersed in the a hydrogel forming polymer matrix, wherein the core is or comprises gelatin, SDS, sorbitol, polyethoxylated castor oil, caprylic/capric triglyceride, 2-(ethoxyethoxy)ethanol; wherein the aqueous phase (i) is or comprises gelatin, sorbitol and SDS; and the disperse phase (ii) is or comprises polyethoxylated castor oil, caprylic/capric triglyceride, 2-(ethoxyethoxy) ethanol and cyclosporin A.

94. A pharmaceutical formulation according to any of the preceding clauses formulated into a unit dosage form for oral administration comprising from 0.1 mg to 1000 mg, optionally from 1 mg to 500 mg, for example 10 mg to 300 mg, or 25 to 250 mg, suitably about 25 mg, 35 mg, about 75 mg, about 180 mg, about 210 mg or about 250 mg of the active ingredient.

95. The pharmaceutical formulation of any preceding clause, wherein the active ingredient is an immunosuppressant, a hydroxylase inhibitor, or an anti-inflammatory, optionally the active ingredient is cyclosporin A, hydralazine or mesalazine.

96. The pharmaceutical formulation of any of clause 19 to 95, wherein the dissolution test is a two stage dissolution test and the two stage dissolution test consists of a first stage having a dissolution medium of 750 ml 0.1N HCl into which the formulation is placed and a second stage commencing at 2 hours, wherein 250 ml 0.2M tribasic sodium phosphate containing 2% sodium dodecyl sulphate (SDS) is added to the dissolution medium and the pH adjusted to 6.8.

97. The pharmaceutical formulation of any of clauses 19 to 95 wherein the dissolution test consists of a dissolution medium consisting of 1000 ml of a 0.05M pH 7.5 phosphate buffer prepared by dissolving monobasic potassium phosphate and sodium hydroxide in water.

98. The pharmaceutical formulation of any preceding clause for use in treating a condition of the GIT.

99. The pharmaceutical formulation of clause 98, wherein the condition of the GIT is selected from inflammatory bowel disease, irritable bowel disease, Crohn's disease, ulcerative colitis, celiac disease, graft vs host disease, gastrointestinal graft-versus-host disease, gastroenteritis, duodenitis, jejunitis, ileitis, peptic ulcer, Curling's ulcer, appendicitis, colitis, pseudomembranous colitis, diverticulosis, diverticulitis, endometriosis, colorectal carcinoma and adenocarcinoma.

100. The pharmaceutical formulation of any of clauses 5 to 9 for use in the treatment of conditions of the small intestine, for example celiac disease, GVHD or Crohn's disease.

101. A method of treating a condition selected from inflammatory bowel disease, irritable bowel disease, Crohn's disease, ulcerative colitis, celiac disease, graft vs host disease, gastrointestinal graft-versus-host disease, gastroenteritis, duodenitis, jejunitis, ileitis, peptic ulcer, Curling's ulcer, appendicitis, colitis, pseudomembranous colitis, diverticulosis, diverticulitis, endometriosis, colorectal carcinoma and adenocarcinoma, wherein the method comprises administering a pharmaceutical formulation of clauses 1-97.

102. A method of treating conditions of the small intestine, for example celiac disease, GVHD or Crohn's disease, comprising administering a pharmaceutical formulation of any of clauses 5 to 9.

103. A process for making a pharmaceutical formulation, the process comprising the step of:
    coating a core with a coating comprising HPMC wherein the weight gain due to the coating is from 0.5% to 20% of the weight of the pharmaceutical formulation.

104. The process of clause 103, further comprising producing the core, wherein producing the core comprises the steps of:
    mixing a non-aqueous phase with an aqueous phase to form a solid colloid, wherein at least one of the aqueous phase or the non-aqueous phase comprise a pharmaceutically active ingredient, wherein
    (a) the non-aqueous phase comprises a surfactant; and
    (b) the aqueous phase comprises a hydrogel forming polymer; and then causing the emulsion to solidify.

105. The process of clause 103 or clause 104 for making a pharmaceutical formulation of clauses 1-97.

106. A method of producing more than one batch of a multiplicity of solid unit dosage forms comprising a core, a first coating and a second coating outside the first coating, wherein the core comprises an active ingredient and a hydrogel forming polymer matrix, the first coating comprises or is a water-soluble cellulose ether, and the second coating comprises or is a delayed release polymer, further wherein the first coating is present in an amount to provide each of the more than one batches with a plot of % release of the active ingredient against time with a difference of less than 5 units of % release at any time point in the plot, wherein the method comprises, forming a batch of cores, coating the cores with the first coating in an amount to provide a weight gain due to the coating of from 0.5% and 20% and coating the core with the second coating to provide the one or more batches.

What is claimed is:

1. A pharmaceutical formulation comprising a population of minibeads presented in a unit dosage form for oral administration, said minibeads each comprising a core and a single coating, wherein:

the population comprises minibeads having a largest cross sectional dimension of from about 0.5 mm to about 2.5 mm;

the core is in the form of a solid colloid, the colloid comprising a continuous phase and a disperse phase;

the continuous phase comprises a gelatin matrix, the matrix comprising an anionic surfactant and optionally a plasticiser selected from glycerin, a polyol, polyethylene glycol, triethyl citrate or a mixture thereof;

the disperse phase is a hydrophobic phase that comprises cyclosporin A in solution and a non-ionic surfactant;

the coating comprises at least 50% by weight of the coating of one or more film-forming polymers and optionally, in addition to film-forming polymer(s), one or more other components other than film-forming polymers;

the one or more film-forming polymers present in the coating are one or more water soluble cellulose ethers selected from the group consisting of hydroxyethyl cellulose, hydroxypropyl cellulose, hydroxyethyl methylcellulose and hydroxypropylmethyl cellulose and combinations thereof, provided that hydroxypropylmethyl cellulose is at least one of the film-forming polymers;

the coating is present in an amount corresponding to a weight gain due to the coating of from 9% to 15% by weight of the core; and said minibeads do not comprise a second coating.

2. A pharmaceutical formulation of claim 1, wherein the coating is present in an amount corresponding to a weight gain due to the coating of from 10% to 15% by weight of the core.

3. A pharmaceutical formulation of claim 1, wherein the anionic surfactant is at least one surfactant selected from fatty acid salts and bile salts.

4. A pharmaceutical formulation of claim 1, wherein the anionic surfactant is an alkyl sulphate salt.

5. A pharmaceutical formulation of claim 1, wherein the anionic surfactant is sodium dodecyl sulphate.

6. A pharmaceutical formulation of claim 1, wherein the disperse phase comprises a medium chain mono- di- or triglyceride, a polyethoxylated castor oil and 2-(ethoxyethoxy)ethanol.

7. A pharmaceutical formulation of claim 6, wherein the medium chain mono- di- or triglyceride is a medium chain triglyceride.

8. A pharmaceutical formulation of claim 1, wherein the non-ionic surfactant is selected from sorbitan-based surfactants, PEG-fatty acids, glyceryl fatty acids and poloxamers.

9. A pharmaceutical formulation of claim 1, wherein the non-ionic surfactant is polyethoxylated castor oil.

10. A pharmaceutical formulation of claim 1, wherein the disperse phase comprises a solvent.

11. A pharmaceutical formulation of claim 10, wherein the solvent is 2-(ethoxyethoxy)ethanol.

12. A minibead for oral administration, said minibead comprising a core and a single coating, wherein:

the minibead has a largest cross sectional dimension of from about 0.5 mm to about 2.5 mm;

the core is in the form of a solid colloid, the colloid comprising a continuous phase and a disperse phase;

the continuous phase comprises a gelatin matrix, the matrix comprising an anionic surfactant and optionally a plasticiser selected from glycerin, a polyol, polyethylene glycol, triethyl citrate or a mixture thereof;

the disperse phase is a hydrophobic phase that comprises cyclosporin A in solution and a non-ionic surfactant;

the coating comprises at least 50% by weight of the coating of one or more film-forming polymers and optionally, in addition to film-forming polymer(s), one or more other components other than film-forming polymers;

the one or more film-forming polymers present in the coating are one or more water soluble cellulose ethers selected from the group consisting of hydroxyethyl cellulose, hydroxypropyl cellulose, hydroxyethyl methylcellulose and hydroxypropylmethyl cellulose and combinations thereof, provided that hydroxypropylmethyl cellulose is at least one of the film-forming polymers;

the coating is present in an amount corresponding to a weight gain due to the coating of from 9% to 15% by weight of the core; and said minibead does not comprise a second coating.

13. The minibead of claim 12, wherein the coating is present in an amount corresponding to a weight gain due to the coating of from 10% to 15% by weight of the core.

14. The minibead of claim 12, wherein the anionic surfactant is at least one surfactant selected from fatty acid salts and bile salts.

15. The minibead of claim 12, wherein the anionic surfactant is an alkyl sulphate salt.

16. The minibead of claim 12, wherein the anionic surfactant is sodium dodecyl sulphate.

17. The minibead of claim 12, wherein the disperse phase comprises a medium chain mono- di- or triglyceride, a polyethoxylated castor oil and 2-(ethoxyethoxy)ethanol.

18. The minibead of claim 17, wherein the medium chain mono- di- or triglyceride is a medium chain triglyceride.

19. The minibead of claim 12, wherein the non-ionic surfactant is selected from sorbitan-based surfactants, PEG-fatty acids, glyceryl fatty acids and poloxamers.

20. The minibead of claim 12, wherein the non-ionic surfactant is polyethoxylated castor oil.

21. The minibead of claim 12, wherein the disperse phase comprises a solvent.

22. The minibead of claim 21, wherein the solvent is 2-(ethoxyethoxy)ethanol.

23. The pharmaceutical formulation of claim 1, wherein the coating comprises at least 60% by weight of the coating of one or more film-forming polymers.

24. The pharmaceutical formulation of claim 1, wherein the coating comprises from 50% to 90% by weight of the coating of one or more film-forming polymers.

25. The pharmaceutical formulation of claim 1, wherein the coating comprises from 60% to 80% by weight of the coating of one or more film-forming polymers.

26. The minibead of claim 12, wherein the coating comprises at least 60% by weight of the coating of one or more film-forming polymers.

27. The minibead of claim 12, wherein the coating comprises from 50% to 90% by weight of the coating of one or more film-forming polymers.

28. The minibead of claim 12, wherein the coating comprises from 60% to 80% by weight of the coating of one or more film-forming polymers.

* * * * *